US012807942B2

(12) United States Patent
Lisowski et al.

(10) Patent No.: US 12,807,942 B2
(45) Date of Patent: Nov. 24, 2026

(54) NUCLEIC ACID MOLECULES AND METHODS FOR AAV VECTOR SELECTION

(71) Applicant: Children's Medical Research Institute, Westmead (AU)

(72) Inventors: Leszek Lisowski, Westmead (AU); Marti Cabanes-Creus, Westmead (AU); Adrian Westhaus, Westmead (AU)

(73) Assignee: Children's Medical Research Institute, Westmead (AU)

(*) Notice: Subject to any disclaimer, the term of this patent is extended or adjusted under 35 U.S.C. 154(b) by 1590 days.

(21) Appl. No.: 17/286,420

(22) PCT Filed: Oct. 17, 2019

(86) PCT No.: PCT/AU2019/051133

§ 371 (c)(1),
(2) Date: Apr. 16, 2021

(87) PCT Pub. No.: WO2020/077411

PCT Pub. Date: Apr. 23, 2020

(65) Prior Publication Data

US 2021/0388343 A1 Dec. 16, 2021

(30) Foreign Application Priority Data

Oct. 17, 2018 (AU) ................................ 2018903925

(51) Int. Cl.
*C12N 15/10* (2006.01)
*C12N 15/86* (2006.01)

(52) U.S. Cl.
CPC ......... *C12N 15/1086* (2013.01); *C12N 15/86* (2013.01); *C12N 2750/14121* (2013.01); *C12N 2750/14122* (2013.01); *C12N 2750/14143* (2013.01); *C12N 2840/203* (2013.01)

(58) Field of Classification Search
None
See application file for complete search history.

(56) References Cited

U.S. PATENT DOCUMENTS 7,927,585 B2 4/2011 Snyder
2017/0183647 A1* 6/2017 Chavez et al. ..... C12N 15/1086

FOREIGN PATENT DOCUMENTS

WO WO-2018/1199330 6/2018
WO WO 2018/156654 8/2018
WO WO-2018156654 A1 * 8/2018 ............. A61P 27/02

OTHER PUBLICATIONS

Waterkamp et al., "Isolation of targeted AAV2 vectors from novel virus display libraries," J Gene Med (2006) 8:1307-1319.
Ojala et al., 'In vivo selection of a computationally designed SCHEMA AAV library yields a novel variant for infection of adult neural stem cells in the SVZ', Molecular Therapy (2018) vol. 26, pp. 304-319.

* cited by examiner

*Primary Examiner* — Kaijiang Zhang
(74) *Attorney, Agent, or Firm* — MORRISON & FOERSTER LLP

(57) ABSTRACT

The present disclosure relates generally to nucleic acid molecules and methods for identifying AAV vectors with desirable properties, including nucleic acid molecules and methods useful for identifying novel cap genes for vectorization, production of AAV vectors and AAV libraries.

20 Claims, 16 Drawing Sheets

Specification includes a Sequence Listing.

A.

B.

NUCLEIC ACID MOLECULES AND METHODS FOR AAV VECTOR SELECTION

FIELD OF THE DISCLOSURE

The present disclosure relates generally to nucleic acid molecules and methods for identifying AAV vectors with desirable properties, including nucleic acid molecules and methods useful for identifying novel cap genes suitable for vectorization, production of AAV vectors and AAV libraries.

CROSS REFERENCE TO RELATED APPLICATIONS

This application is a National Stage application under 35 U.S.C. § 371 of International Application No. PCT/AU2019/051133, filed internationally on Oct. 17, 2019, which claims priority to Australian Provisional Application No. 2018903925 entitled "Nucleic acid molecules and methods for AAV vector selection" filed 17 Oct. 2018, the contents of which are incorporated herein by reference in their entirety.

BACKGROUND OF THE DISCLOSURE

Gene therapy has most commonly been investigated and achieved using viral vectors, with notable recent advances being based on adeno-associated viral vectors. Adeno-associated virus (AAV) is a replication-deficient parvovirus, the single-stranded DNA genome of which is about 4.7 kb in length. The AAV genome includes inverted terminal repeat (ITRs) at both ends of the molecule, flanking two open reading frames: rep and cap. The cap gene encodes three capsid proteins: VP1, VP2 and VP3. The three capsid proteins typically assemble in a ratio of 1:1:8-10 to form the AAV capsid, although AAV capsids containing only VP3, or VP1 and VP3, or VP2 and VP3, have been produced. The cap gene also encodes the assembly activating protein (AAP) from an alternative open reading frame. AAP promotes capsid assembly, acting to target the capsid proteins to the nucleolus and promote capsid formation. The rep gene encodes four regulatory proteins: Rep78, Rep68, Rep52 and Rep40. These Rep proteins are involved in AAV genome replication.

The ITRs are involved in several functions, in particular integration of the AAV DNA into the host cell genome, as well as genome replication and packaging. When AAV infects a host cell, the viral genome can integrate into the host's chromosomal DNA resulting in latent infection of the cell. Thus, AAV can be exploited to introduce heterologous sequences into cells. In nature, a helper virus (for example, adenovirus or herpesvirus) provides protein factors that allow for replication of AAV in the infected cell and packaging of new virions. In the case of adenovirus, genes E1A, E16, E2A, E4 and VA provide helper functions. Upon infection with a helper virus, the AAV provirus is rescued and amplified, and both AAV and the helper virus are produced.

AAV vectors (also referred to as recombinant AAV, rAAV) that contain a genome that lacks some, most or all of the native AAV genome and instead contains one or more heterologous sequences flanked by the ITRs have been successfully used in gene therapy settings. These AAV vectors are widely used to deliver heterologous nucleic acid to cells of a subject for therapeutic purposes, and in many instances, it is the expression of the heterologous nucleic acid that imparts the therapeutic effect. Although several AAV vectors have now been used in the clinic, there are ongoing efforts to identify and produce new AAV vectors with altered properties, such as altered tropism, reduced recognition by the immune system, reduced immunogenicity, and/or increased transduction efficiency. These efforts typically involve directed evolution of AAV, whereby AAV capsid libraries used to generate AAV libraries which are then subjected to selection, sometime requiring multiple rounds of selection, on host cells to identify AAV particles of interest, which are then vectorised.

Typically, directed evolution of AAV is performed using replication-competent AAV libraries. These provide the engineered viral genomes with the opportunity to naturally increase their frequency upon replication in targeted cells in the presence of helper virus. Human Adenovirus (e.g. Ad5) has been commonly utilised as a helper virus in order to selectively amplify AAV that have successfully reached the nucleus of target cells. In addition to selecting for functional virus that is able to complete the intracellular journey into the nucleus, this approach reduces the time in between selection rounds due to the fact that fully packaged AAV particles are released from the cells into the media at the end of each round and can be directly used for subsequent rounds of selection. However, despite those desirable characteristics, replication-competent AAV libraries have several major drawbacks: 1) they require co-infection with an Adenovirus, which restricts selection to cells that can be infected with an adenovirus, 2) they cannot differentiate which cells selection takes place in when using complex tissues or cell populations, and 3) the platform inherently selects for the best virus rather than the best vector, such that those variants selected may simply be the most efficient at entering the cells (i.e. transduction) and/or at replication. Transgene expression, which is the most important attribute for vectorology applications, is not an attribute that is selected for.

PCR-recovery of AAV cap genes following selection rounds is also widely used for recovering AAVs that are successful at transducing target cells or tissues during the directed evolution methods. This strategy has also been used successfully to isolate improved AAV variants in a number of studies, and it is particularly well-suited for selection procedures where the cell type of interest is either not accessible or permissive to adenoviral infection. However, since this method relies on the purification of total DNA from the target cell, there is a risk of amplifying AAV genomes that have transduced the cells (physical transduction) but have not completed the journey into the nucleus and thus are unable to functionally transduce the cells, i.e. facilitate expression of the transgene in the cell.

There is therefore a need to develop alternative methods for selecting and identifying AAV vectors that facilitate robust transgene expression in host cells of interest.

SUMMARY OF THE DISCLOSURE

The present disclosure describes methods useful for AAV-directed evolution where the selection pressure is based on transgene expression, which is a critical component of many AAV vectors developed for therapeutic purposes. The selection platforms described herein therefore enable selection and identification of AAV vectors that facilitate robust expression of a transgene in a host cell or tissue of choice. The disclosure also provides the necessary components for carrying out the methods, including replication-incompetent AAV particles and AAV libraries for use in the methods, and nucleic acid molecules to generate the replication-incompetent AAV particles and AAV libraries.

In one aspect, therefore, provided is a method for identifying an AAV cap gene suitable for vectorization, comprising: a) transducing host cells with a library of replication-incompetent AAV, wherein the replication-incompetent AAV comprise a genome comprising two AAV ITRs flanking a reporter gene and a cap gene; b) selecting one or more host cells in which expression of the reporter gene is detected; c) isolating RNA and optionally DNA from the one or more host cells from b); d) detecting reporter gene or cap gene mRNA; and e) recovering the one or more cap genes from the RNA or the DNA, or from cDNA produced from the mRNA, thereby identifying one or more AAV cap genes suitable for vectorization.

In some embodiments, the reporter gene and the cap gene are operably linked to a single promoter, and the reporter gene and the cap gene are separated by an internal ribosome binding site (IRES). In other embodiments, the reporter gene is operably linked to a first promoter and the cap gene is operably linked to a second promoter. In some examples, the single promoter or the first promoter is a ubiquitous and/or constitutive promoter, e.g. spleen focus forming virus (SFFV) promoter, Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, the elongation factor-1 alpha promoter (EF-1α), or the short elongation factor-1 alpha promoter (EFS). In further examples, the second promoter is an AAV promoter.

In particular embodiments, the cap gene comprises a 3' UTR and/or a 5' UTR.

In one embodiment, the reporter gene comprises a barcode, e.g. at the 3' end of the reporter gene. In such embodiments, the methods may further comprise, in step d) converting the RNA to cDNA; amplifying and sequencing the barcode in the cDNA to identify one or more enriched barcodes; and identifying DNA that contains one of the enriched barcodes; and in step e) recovering the one or more cap genes from the DNA identified as containing one of enriched barcodes.

In particular examples, the reporter gene comprises a first barcode at the 3' end of the reporter gene, and the genome further comprises, between the two ITRs, a bacterial origin of replication, an antibiotic resistance gene, and a second barcode, wherein the first and second barcodes are at opposite ends of the genome and flank the reporter gene, the cap gene, the origin of replication and the antibiotic resistance gene. The cap gene may also comprises a 3' UTR. In such embodiments, step d) further comprises: 1) converting the RNA to cDNA; 2) amplifying and sequencing the first barcode in the cDNA to identify one or more enriched first barcodes; amplifying one or more genomes from the DNA using primers specific for the first and second barcodes then circularizing the one or more resulting amplicons to produce one or more plasmids, wherein the first and second barcodes are adjacent each other in the one or more plasmids, and transforming the one or more plasmids into bacteria; and amplifying and sequencing the first and second barcodes from the one or more plasmids; and 3) identifying DNA that contains an enriched first barcode identified in 2); and step e) comprises recovering the one or more cap genes from DNA identified as containing an enriched first barcode.

In one embodiment of the above methods, the genome comprises an intron between the first promoter and the reporter gene; between the second promoter and the cap gene; between the single promoter and the reporter gene; and/or between the single promoter and the cap gene. In further embodiments, the genome comprises a poly adenylation sequence.

In some of the methods, recovering the one or more cap genes comprises amplification of the one or more cap genes. In particular examples, recovering the one or more cap genes comprises amplification of the cap gene using primers specific for the second promoter and the 3'UTR. In further examples, recovering the one or more cap genes from the DNA comprises amplification of the genome, e.g. using primers specific for the barcode and the 3' UTR. In some examples, recovering the one or more cap genes from the DNA can comprise amplification of the genome, e.g. using primers specific for the first barcode and the second barcode.

In particular embodiments, a plurality of cap genes are recovered in f), and the method further comprises f) producing a plurality of replication-incompetent AAV as defined in a) with the plurality of cap genes. In some examples, steps a)-f) are repeated one or more times.

The reporter gene may encode, for example, a fluorescent protein (e.g. blue, cyan, green, yellow, orange, red, or far-red fluorescent protein) or a cell surface molecule.

In some embodiments of the above methods, step b) comprises selecting a subpopulation of host cells in which expression of the detectable marker is detected, such that the one or more host cells selected in b) are a subpopulation of the host cells in a).

In further embodiments, the one or more host cells or subpopulation of host cells are selected by fluorescence activated cell sorting (FACS), magnetic-activated cell sorting (MACS) or sorting based on biotin labelling.

The methods described above may further comprise producing one or more AAV vectors using the one or more cap genes identified for vectorization. Thus, also provided is an AAV vector produced by such methods.

In a further aspect, provided is a method for producing replication-incompetent AAV, comprising:

introducing into a host cell:

a first nucleic acid molecule comprising an AAV genome comprising two AAV ITRs flanking a reporter gene and a cap gene;

a second nucleic acid molecule comprising a rep gene; and a third nucleic acid molecule comprising Adenovirus helper functions, or an Adenovirus; and culturing the host cell under conditions suitable for packaging the genome, thereby producing replication-incompetent AAV.

In some examples, the reporter gene and the cap gene are operably linked to a single promoter, and the reporter gene and the cap gene are separated by an internal ribosome binding site (IRES). In other examples, the reporter gene is operably linked to a first promoter and the cap gene is operably linked to a second promoter. The single promoter or the first promoter may be, in some instances, a ubiquitous and/or constitutive promoter, e.g. spleen focus forming virus (SFFV) promoter, Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, the elongation factor-1 alpha promoter (EF-1α), or the short elongation factor-1 alpha promoter (EFS). In further examples, the second promoter is an AAV promoter. The cap gene may also comprise a 3' UTR and/or a 5' UTR, and reporter gene may encode a fluorescent protein (e.g. blue, cyan, green, yellow, orange, red, or far-red fluorescent protein) or a cell surface molecule.

In some embodiments, the reporter gene comprises a barcode, such as at the 3' end of the reporter gene. In some examples of this embodiment, in the first nucleic acid molecule, the reporter gene comprises a first barcode at the 3' end, and the genome further comprises, between the two ITRs, a bacterial origin of replication, an antibiotic resistance gene, and a second barcode, wherein the first and second barcodes are at opposite ends of the genome and flank the reporter gene, the cap gene, the origin of replication and the antibiotic resistance gene.

In some embodiments of the method for producing replication-incompetent AAV, a plurality of the first, second and third nucleic acid molecules is introduced into a plurality of host cells to thereby produce a library of replication-incompetent AAV, wherein the plurality of first nucleic acid molecules comprises a plurality of cap genes having two or more different nucleic acid sequences. In some examples, when the reporter gene comprises a barcode, at least two of the first nucleic acid molecules in the plurality comprise a barcode with a unique nucleic acid sequence relative to one another. Typically, at least 80%, 81%, 82%, 83%, 84%, 85%, 86%, 87%, 88%, 89%, 90%, 91%, 92%, 93%, 94%, 95%, 96%, 97%, 98% or 99% of the first nucleic acid molecules in the plurality comprise a barcode with a unique nucleic acid sequence relative to other barcodes in the plurality.

In embodiments where the first nucleic acid molecule comprises a first barcode and a second barcode, typically at least two of the first nucleic acid molecules in the plurality comprises a first barcode with a unique nucleic acid sequence relative to one another, and a second barcode with a unique nucleic acid sequence relative to one another. in some examples, at least 80%, 81%, 82%, 83%, 84%, 85%, 86%, 87%, 88%, 89%, 90%, 91%, 92%, 93%, 94%, 95%, 96%, 97%, 98% or 99% of the first nucleic acid molecules in the plurality comprise a first barcode with a unique nucleic acid sequence relative to the other first barcodes in the plurality, and a second barcode with a unique nucleic acid sequence relative to the other second barcodes in the plurality.

Also provided is replication-incompetent AAV and/or a library of replication-incompetent AAV produced by the methods described above.

In further aspects, provided is a nucleic acid molecule, comprising an AAV genome comprising two AAV ITRs flanking a reporter gene and a cap gene operably linked to a single promoter, wherein the reporter gene and a cap gene are separated by an IRES and wherein nucleic acid molecule does not comprise a rep gene. in some examples, the cap gene comprises a 3' UTR and/or a 5' UTR.

In another aspect, provided is nucleic acid molecule, comprising an AAV genome comprising two AAV ITRs flanking a reporter gene operably linked to a first promoter, and a cap gene operably linked to a second promoter, wherein the nucleic acid molecule does not comprise a rep gene and wherein the reporter gene comprises a barcode. In some examples, the barcode is at the 3' end of the reporter gene. In particular embodiments, the reporter gene comprises a first barcode at the 3' end of the gene, and the genome further comprises, between the two ITRs, a bacterial origin of replication, an antibiotic resistance gene, and a second barcode, wherein the first and second barcodes are at opposite ends of the genome and flank the reporter gene, the cap gene, the origin of replication and the antibiotic resistance gene.

The reporter gene in the nucleic acids of the present disclosure may be, for example, a fluorescent protein (e.g. a blue, cyan, green, yellow, orange, red, or far-red fluorescent protein) or a cell surface molecule.

In another aspect, provided is a plurality of nucleic acid molecules, wherein each nucleic acid molecule in the plurality comprises an AAV genome comprising two AAV ITRs flanking a reporter gene operably linked to a first promoter, wherein the reporter gene comprises a first barcode and wherein the nucleic acid molecule does not comprise a rep gene; and at least two of the nucleic acid molecules in the plurality comprises a first barcode with a unique nucleic acid sequence relative to other first barcodes in the plurality. In some embodiments, at least 80%, 81%, 82%, 83%, 84%, 85%, 86%, 87%, 88%, 89%, 90%, 91%, 92%, 93%, 94%, 95%, 96%, 97%, 98% or 99% of the nucleic acid molecules in the plurality comprise a first barcode with a unique nucleic acid sequence relative to other first barcodes in the plurality. In particular embodiments, the barcode is at the 3' end of the reporter gene.

In a further aspect, provided is a plurality of nucleic acid molecules, wherein:

each nucleic acid molecule in the plurality comprises an AAV genome comprising two AAV ITRs flanking a reporter gene operably linked to a first promoter, wherein the reporter gene comprises a barcode at the 3' end; a bacterial origin of replication; an antibiotic resistance gene; and a second barcode, wherein the first and second barcodes are at opposite ends of the genome and flank the reporter gene, the origin of replication and the antibiotic resistance gene, and wherein the nucleic acid molecule does not comprise a rep gene; and at least two of the nucleic acid molecules in the plurality comprises a first barcode with a unique nucleic acid sequence relative other first barcodes in the plurality and a second barcode with a unique nucleic acid sequence other second barcodes in the plurality.

In some examples of this aspect, at least 80%, 81%, 82%, 83%, 84%, 85%, 86%, 87%, 88%, 89%, 90%, 91%, 92%, 93%, 94%, 95%, 96%, 97%, 98% or 99% of the nucleic acid molecules in the plurality comprise a first barcode with a unique nucleic acid sequence relative to other first barcodes in the plurality and a second barcode with a unique nucleic acid sequence relative to other first barcodes in the plurality.

In particular embodiments of the plurality of nucleic acids, the genome further comprises, between the ITRs, a second promoter and a 3'UTR configured to facilitate insertion of a transgene between the second promoter and the 3'UTR sites such that the transgene is operably linked to the second promoter and 3'UTR. The genome may also further comprises a cap gene between the second promoter and the 3'UTR, wherein at least 80%, 81%, 82%, 83%, 84%, 85%, 86%, 87%, 88%, 89%, 90%, 91%, 92%, 93%, 94%, 95%, 96%, 97%, 98% or 99% the nucleic acid molecules in the plurality comprise a cap gene with a unique nucleic acid sequence relative to other cap genes in the plurality.

The nucleic acid molecule or the plurality of nucleic acid molecules may be a plasmid or plurality of plasmids.

Also provided is a composition comprising a nucleic acid molecule or plurality of nucleic acid molecules as described herein. A combination comprising a nucleic acid molecule or plurality of nucleic acid molecules as described herein, and a further nucleic acid molecule comprising a rep gene operably linked to a promoter, is also provided. The combination may also comprise a nucleic acid molecule comprising Adenovirus helper functions, or an Adenovirus.

In another aspect, provided is a host cell or a plurality of host cells, comprising a nucleic acid molecule or plurality of nucleic acid molecules described herein; and optionally a nucleic acid molecule comprising Adenovirus helper functions, or an Adenovirus.

In a further aspect, provided is a kit, comprising a nucleic acid molecule or a plurality of nucleic acid molecules as described herein; and a nucleic acid molecule comprising a rep gene operably linked to a promoter. In some embodiments, the kit further comprises a nucleic acid molecule comprising Adenovirus helper functions, or an Adenovirus, and optionally further comprises instructions for use. As would be appreciated, the kit can be used in the methods described herein for producing replication-incompetent AAV.

BRIEF DESCRIPTION OF THE DRAWINGS

Embodiments of the disclosure are described herein, by way of non-limiting example only, with reference to the following drawings.

DETAILED DESCRIPTION

Figure 1:
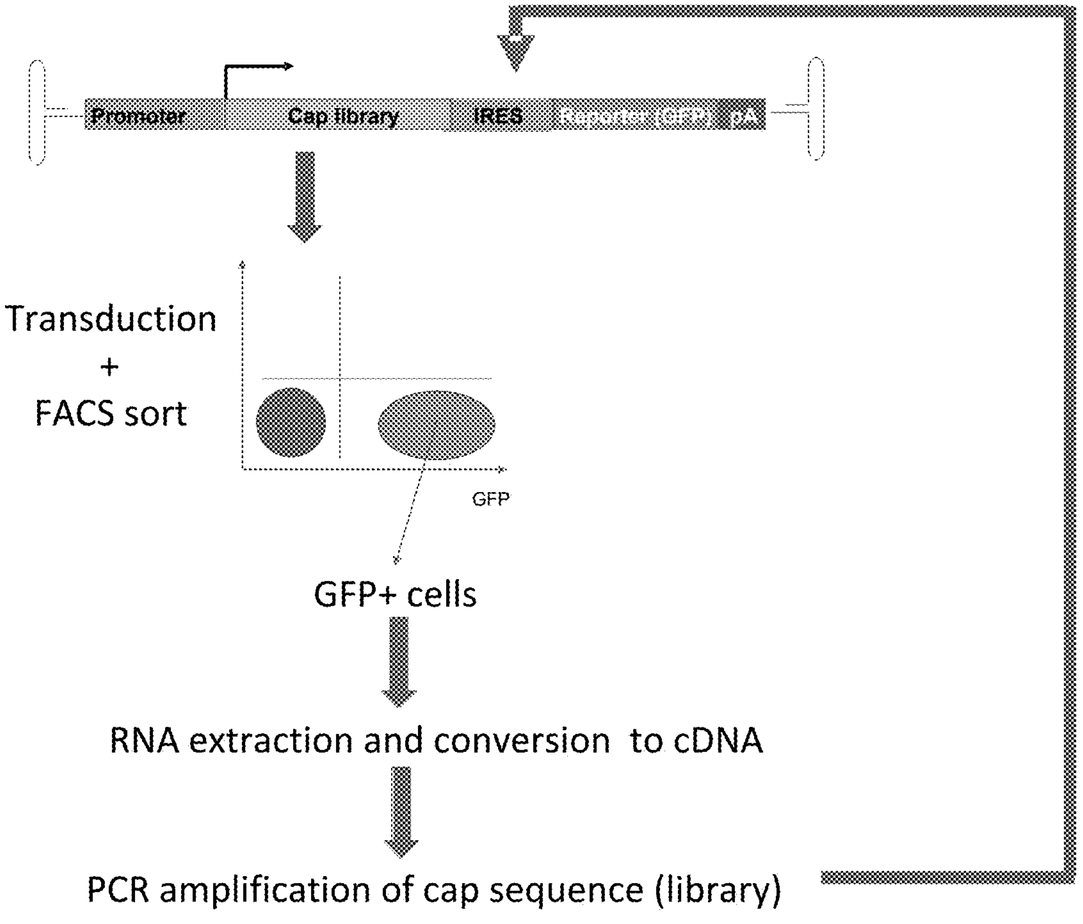
FIG. 1 is a schematic representation of a selection platform based on functional transduction. A library of replication-incompetent AAV is transduced into cells. The replication-incompetent AAV contain a genome comprising ITRs flanking a reporter gene (e.g. GFP) operably linked to a first promoter, and a cap gene from a capsid library operably linked to a second promoter. Following transduction and culture of the cells, the cells are sorted to isolate those expressing the reporter gene (e.g. GFP) and RNA is extracted from these cells. The RNA is converted to cDNA and the cap genes are detected and amplified by PCR and can then be used to generate more replication-incompetent AAV for a further round(s) of screening or can be used for vectorization.

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it is understood that such identifiers can change and particular information on the internet can come and go, but equivalent information can be found by searching the internet. Reference to the identifier evidences the availability and public dissemination of such information.

As used herein, the singular forms "a", "an" and "the" also include plural aspects (i.e. at least one or more than one) unless the context clearly dictates otherwise. Thus, for example, reference to "a polypeptide" includes a single polypeptide, as well as two or more polypeptides.

In the context of this specification, the term "about," is understood to refer to a range of numbers that a person of skill in the art would consider equivalent to the recited value in the context of achieving the same function or result.

Throughout this specification and the claims that follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, a "barcode" refers to a sequence of a nucleic acid that, when combined with the sequence of another nucleic acid (e.g. reporter gene, an AAV genome or a cap gene) serves to identify the other nucleic acid molecule. Barcodes for use in accordance with the present disclosure typically have a sequence of the formula (N)n, where N is a nucleotide that is independently selected from A, G, T and C, and n is at least 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 or more. For the purposes herein, a barcode has a sequence that that is unique, or at least partially unique, to a particular AAV vector or nucleic acid molecule, such that in any AAV library or plurality of nucleic acid molecules, at least two of the barcodes in the library or plurality have a different sequence. Ideally, all of the barcodes have a different sequence, i.e. each is unique. Generally, at least 80%, 81%, 82%, 83%, 84%, 85%, 86%, 87%, 88%, 89%, 90%, 91%, 92%, 93%, 94%, 95%, 96%, 97%, 98% or 99% are unique, i.e. at least 80%, 81%, 82%, 83%, 84%, 85%, 86%, 87%, 88%, 89%, 90%, 91%, 92%, 93%, 94%, 95%, 96%, 97%, 98% or 99% of the AAV in the library, or the nucleic acid molecules in the plurality, comprise a barcode with a unique (i.e. different) nucleic acid sequence relative to other barcodes in the library or plurality. Barcodes can therefore be used to "track" each of the AAV or nucleic acid molecules through a selection process. In some embodiments of the present disclosure, the barcode is comprised within, or is fused, to a reporter gene, such that the transcript produced upon transcription of the reporter gene contains a transcript of the barcode sequence. Thus, reference herein to a reporter gene "comprising" a barcode encompasses a reporter gene fused to a barcode such that the transcript contains both the reporter gene and barcode sequences.

The term "host cell" refers to a cell, such as a mammalian cell, that has exogenous DNA introduced into it, such as a vector or other polynucleotide. The term includes the progeny of the original cell into which the exogenous DNA has been introduced. Thus, a "host cell" as used herein generally refers to a cell that has been transfected or transduced with exogenous DNA.

As used herein, a "vector" includes reference to both polynucleotide vectors and viral vectors, each of which are capable of delivering a transgene contained within the vector into a host cell. Vectors can be episomal, i.e., do not integrate into the genome of a host cell, or can integrate into the host cell genome. The vectors may also be replication competent or replication-deficient. Exemplary polynucleotide vectors include, but are not limited to, plasmids, cosmids and transposons. Exemplary viral vectors include, for example, AAV, lentiviral, retroviral, adenoviral, herpes viral and hepatitis viral vectors.

As used herein, "adeno-associated viral vector" or AAV vector refers to a vector in which the capsid is derived from an adeno-associated virus, including without limitation, AAV1, AAV2, AAV3, AAV4, AAV5, AAV6, AAV7, AAV8, AAV9, AAV10, AAV11, AAV12 or AAV13, or using synthetic or modified AAV capsid proteins, including chimeric capsid proteins. When referring to AAV vectors, both the source of the genome and the source of the capsid can be identified, where the source of the genome is the first number designated and the source of the capsid is the second number designated. Thus, for example, a vector in which both the capsid and genome are derived from AAV2 is more accurately referred to as AAV2/2. A vector with an AAV6-derived capsid and an AAV2-derived genome is most accurately referred to as AAV2/6. A vector with the synthetic DJ capsid and an AAV2-derived genome is most accurately referred to as AAV2/DJ. For simplicity, and because most vectors use an AAV2-derived genome, it is understood that reference to an AAV6 vector generally refers to an AAV2/6 vector, reference to an AAV2 vector generally refers to an AAV2/2 vector, etc. An AAV vector may also be referred to herein as "recombinant AAV", "rAAV", "recombinant AAV virion", and "rAAV virion," terms which are used interchangeably and refer to a replication-defective virus that includes an AAV capsid shell encapsidating an AAV genome. The AAV vector genome (also referred to as vector genome, recombinant AAV genome or rAAV genome) comprises a transgene flanked on both sides by functional AAV ITRs. Typically, one or more of the wild-type AAV genes have been deleted from the genome in whole or part, preferably the rep and/or cap genes. Functional ITR sequences are necessary for the rescue, replication and packaging of the vector genome into the rAAV virion.

The term "ITR" refers to an inverted terminal repeat at either end of the AAV genome. This sequence can form hairpin structures and is involved in AAV DNA replication and rescue, or excision, from prokaryotic plasmids. ITRs for use in the present disclosure need not be the wild-type nucleotide sequences, and may be altered, e.g., by the insertion, deletion or substitution of nucleotides, as long as the sequences provide for functional rescue, replication and packaging of rAAV.

As used herein, the term "operably-linked" with reference to a promoter and a coding sequence means that the transcription of the coding sequence is under the control of, or driven by, the promoter.

The term "reporter gene" as used herein refers to a gene which encodes a gene product suitable for screening or sorting cells transduced with an AAV described herein that contains a genome comprising the reporter gene. The gene product can be any polypeptide or protein suitable for the intended use for screening technologies and can be cytoplasmic or membrane-bound. To facilitate sorting, the gene product can be directly detectable (e.g. may be a fluorescent protein), or may be indirectly-detectable, such as by using a labelled antibody that binds to the gene product. For the purposes of the present disclosure, the reporter gene does not encode an AAV capsid.

It will be appreciated that the above described terms and associated definitions are used for the purpose of explanation only and are not intended to be limiting.

TABLE 1

Brief Description of the Sequences

| SEQ ID NO. | Description |
|---|---|
| 1 | FT LSP AAV2 plasmid |
| 2 | AAV ITR left |
| 3 | AAV ITR right |
| 4 | eGFP gene |
| 5 | SV40 polyA |
| 6 | LSP promoter |
| 7 | EF1a short promoter |
| 8 | SFFV promoter |
| 9 | Fraqment of rep containing the p40 promoter |
| 10 | SV40 intron |
| 11 | rep 2 gene |
| 12 | p5 promoter |
| 13 | Cap rescue F primer |
| 14 | Cap rescue R primer |
| 15 | CMV promoter |
| 16 | encephalomyocarditis virus IRES |
| 17 | eukaryotic initiation factor 4G1 IRES |
| 18 | mCherry |
| 19 | SC010 primer |
| 20 | SC011 primer |
| 21 | VG619 primer |
| 22 | VG620 primer |
| 23 | VG660 primer |
| 24 | VG661 primer |
| 25 | VG688 primer |
| 26 | VG689 primer |
| 27 | VG732 primer |
| 28 | VG690 primer |
| 29 | VG691 primer |
| 30 | VG693 primer |
| 31 | VG694 primer |
| 32 | VG760 primer |
| 33 | VG761 primer |
| 34 | cap gene lco6 |
| 35 | CMV enhancer |
| 36 | 5' UTR |
| 37 | VG0896__crosspack__f primer |
| 38 | VG0897__crosspack__r primer |

Functional Transduction Platforms

The present disclosure is directed, in part, to methods for AAV directed evolution where the selection pressure is based on transgene expression. Previously-described methods, which generally use replication-competent AAV, are typically designed such that they potentially select for AAV that are most efficient at entering cells (physical transduction) and/or replicating: there is no assessment of transgene expression, which is a critical aspect of many AAV vectors designed for therapeutic purposes. When the AAV selected using the replication-competent platform are vectorised and replication is disabled, it is not uncommon for the resulting vector to perform poorly with respect to transgene expression following transduction into host cells. In contrast, the methods of the present invention are based on selection of AAV that are able to facilitate strong transgene expression following entry into the desired host cells, i.e. "functional transduction".

The only essential AAV elements required for any directed evolution process are the cis acting ITRs and the cap library, which undergoes the selection process. Replication-competent platforms generally utilize AAV with genomes in which both the rep and cap genes are flanked by ITRs. To reduce the bias towards selection of AAV vectors that are efficient at replicating but not necessarily efficient at functional transduction, the inventors eliminated the ability of the AAV to self-replicate in the presence of a helper virus. Specifically, the rep gene was removed from the genome and substituted with a reporter gene that can be used to detect and/or assess functional transduction. The resulting AAV therefore contain two ITRs flanking a reporter gene driven by a promoter (which may be ubiquitous or tissue-specific) and cap gene from a library, and are replication-incompetent. Upon transduction into host cells of choice, cells expressing the reporter gene are identified and selected, DNA and/or RNA from those cells is extracted and the cap genes are recovered. These cap genes can either be used to produce more replication-incompetent AAV for further selection rounds, or can be used for vectorization. Thus, the functional transduction platforms described herein can be used to identify cap genes from a library for vectorization.

The reporter gene encodes a protein that facilitates selection of cells expressing the reporter gene by any means for sorting cells, including for example, fluorescence-activated cell sorting (FACS), magnetic-activated cell sorting (MACS) and sorting based on biotin labelling. Sorting of the cells can be achieved by direct detection of the protein encoded by the reporter gene, such as when the reporter gene encodes a fluorescent protein, or indirect, such as when the reporter gene encodes a protein to which an antibody (which could be fluorescently-labelled, biotin-labelled or labelled in any other way that allows sorting) specific for the protein binds, or magnetic beads coated with an antibody specific for the protein binds. Methods for sorting cells on the basis of expression of an intracellular protein or cell-surface protein are well known in the art and can be used herein, and it is well within the ability of a skilled person to select the appropriate sorting technique based on the nature of the reporter gene. In addition to simply sorting cells that are positive for reporter gene expression, the degree of reporter gene expression can also be used to sort cells. For example, cells can be sorted into low-, medium- and high-expressers, and cap genes recovered from one or more of those populations.

In another advantageous embodiment, the transduced cells can be further sorted on the basis of one or more other characteristics or phenotypes, such as the expression of one or more cell surface markers as is well known in the art. In this way, functional transduction of particular subpopulations of cells can be assessed. For example, cells can be stained with one or more antibodies to select for a cell population of interest and cap genes recovered from that cell subpopulation, or tissues can be separated into various cell types and cap genes recovered from each type, allowing for library selection to be performed in multiple cell types simultaneously. This is something that cannot be achieved using previously-described replication-competent selection methods, where AAV particles produced by any cell in the population are harvested without knowing which cell they were produced in.

Selection based on transgene expression can be performed by simply detecting the protein expressed by the reporter gene, selecting cells in which that protein has been detected, and recovering cap genes from DNA extracted from those cells. In other embodiments described herein, selection is performed predominantly on the basis of gene expression (cap gene or reporter gene or both) at the RNA level.

Selection Based on Protein Expression

In one embodiment of the present methods, selection is made on the basis of protein expression of the reporter gene alone. Replication-incompetent AAV containing a genome with ITRs flanking a reporter gene and a cap gene (e.g. from a library) are transduced into host cells. The reporter gene and a cap gene can be under the control of the same promoter (e.g. a ubiquitous or tissue-specific promoter selected on the basis that it is functional in the host cells used for transduction and under the conditions of the selection process) or different promoters. Thus, in some examples, the reporter gene is operably linked to a first promoter, and the cap gene is operably linked to a second promoter. In these examples, the first promoter may be ubiquitous or may be tissue-specific and selected on the basis that it is functional in the host cells used for transduction and under the conditions of the selection. The second promoter can be any promoter suitable for driving expression of the cap gene, although conveniently may be a natural AAV promoter, such as the p40 promoter. Typically, the reporter gene and cap gene are oriented in different directions so that transcription proceeds in different directions along the genome. Generally, the cap gene also contains a 3'UTR directly downstream, and the reporter gene may contain a polyadenylation sequence. The genome does not contain a functional rep gene, thus rendering the AAV replication-incompetent.

Following transduction of the cells with the AAV and subsequent culture under conditions to facilitate reporter gene expression, cells in which protein expression from the reporter gene is detected are selected by sorting. DNA is then extracted from these selected cells and the cap gene is recovered. Recovery of the cap gene can be performed in any manner known to those skilled in the art. Typically PCR amplification of the cap gene is performed to recover the gene, such as by using primers specific for the 5' and 3' ends of the cap gene, or primers specific for regions upstream and downstream of the cap gene, such as primers specific for the second promoter and the 3' UTR that flank the cap gene. The amplified cap genes can then be cloned into the appropriate recipient construct for the functional transduction platform (described in further detail below) and packaged to produce replication-incompetent AAV for a further round of selection. The selection process can be repeated a further 1, 2, 3, 4, 5, 6, 7, 8, 9, 10, 15, 20, 25 or more times before any one or more cap genes recovered in the process are vectorised.

Selection Based on RNA Expression

Selection of cap genes for vectorization can also be performed on the basis of gene expression (either reporter gene or cap gene) at the RNA level. In the embodiment described above in which cap genes are directly amplified from DNA of reporter protein-positive cells, there is a possibility that the recovered cap gene is from a virion that attached to the cell but did not enter, or from a virion that entered but did not lead to transgene expression (in instances where a cell is transduced by several vectors). Selecting or amplifying all cap genes present in functionally transduced cells may therefore be biased because inefficient capsids can be selected through this "bystander effect". To address this, selection platforms based on transgene expression at the RNA level are provided.

In this embodiment, cells positive for the protein product of the reporter gene are first selected (e.g. by FACS, MACS or biotin labelling and sorting), and then RNA transcripts from the capsid and/or reporter gene are detected and assessed (e.g. by conversion to cDNA and the amplification and/or sequencing to detect and/or identify capsid and/or reporter gene sequences) so as to identify capsids that have been enriched in the selection process. Several vector designs can be utilised for these platforms, including those in which the cap and reporter genes are under the control of the same or different promoters, and optionally comprise one or more barcodes.

Single Promoter Genomes

In one embodiment, the replication-incompetent AAV contains a genome with ITRs flanking a cap gene (e.g. from a library) and a reporter gene, where the cap gene and reporter gene are under the control of the same promoter but are separated by an internal ribosome entry site (IRES). The cap gene may be upstream or downstream of the reporter gene. This single promoter embodiment is sometimes referred to in the Examples below as the FT3 or High Targeted Expression (HTE) selection platform. In this embodiment, the target cells are transduced and cells are sorted (or selected) on the basis of reporter protein expression. RNA and optionally DNA are then extracted from the cells. The RNA is converted to cDNA and the capsid sequences are detected and recovered from the cDNA and then used to produce replication-incompetent AAV for a further round of selection (FIG. 1).

In this embodiment, the promoter used to drive the expression of the cap and reporter genes is functional in the host cells used for selection and under the conditions used for selection. Typically, the promoter is constitutive in the host cells used for selection and potentially also for the downstream therapeutic applications. In particular examples, the promoter is a ubiquitous promoter (i.e. functional in multiple tissue types or multiple host cells) and a constitutive promoter. In other examples, the promoter is tissue-specific. Suitable promoters are well known to those skilled in the art and non-limiting examples are provided below.

Recovery of the cap gene can be performed by any manner known to those skilled in the art. Typically PCR amplification of the cap sequence is performed, such as by using primers specific for 5' and 3' regions of the cap gene, and/or primers specific for the upstream and downstream regions flanking the cap gene, e.g. the promoter (e.g. downstream of the transcriptional start site), 5' UTR, 3' UTR or IRES, depending on the configuration of the vector genome. The amplified cap genes can then be cloned into the appropriate construct and packaged to produce replication-incompetent AAV for a further round of selection. The selection process can be repeated a further 1, 2, 3, 4, 5, 6, 7, 8, 9, 10, 15, 20, 25 or more times before any one or more cap genes recovered in the process are vectorised.

Dual Promoter Genomes

Figure 2:
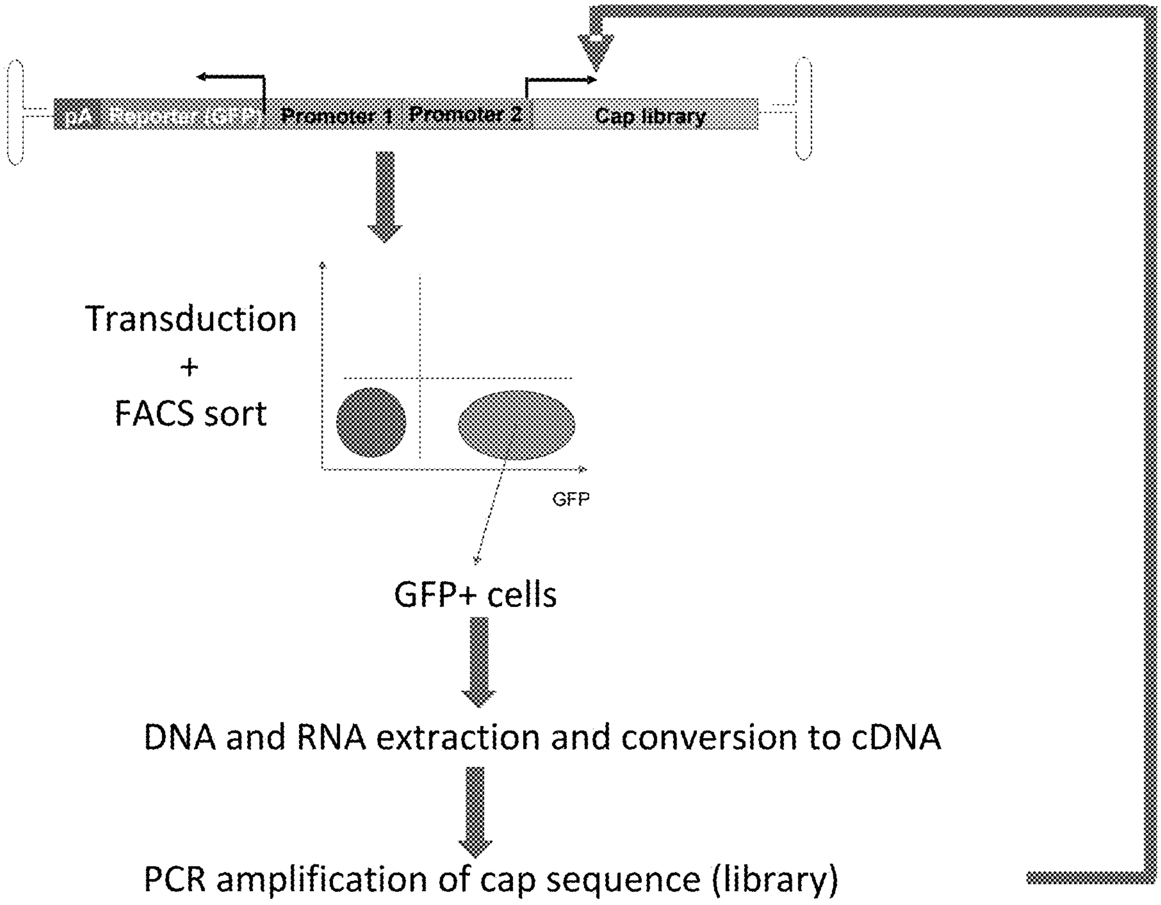
FIG. 2 is a schematic representation of a selection platform based on functional transduction. A library of replication-incompetent AAV is transduced into cells. The replication-incompetent AAV contain a genome comprising ITRs flanking a cap gene from a capsid library operably linked to one promoter and a reporter gene (e.g. GFP) operably linked to another promoter. Following transduction and culture of the cells, the cells are sorted to isolate those expressing the reporter gene (e.g. GFP) and RNA and optionally DNA is extracted from these cells and the RNA is converted to cDNA. The cap genes may be detected and amplified from the cDNA directly when the promoter driving expression of the cap gene is functional in the selection process. When the promoter driving expression of the cap gene is not functional in the selection process, reporter gene mRNA is detected and cap genes are then by amplified from the DNA isolated from the cells. Amplified cap genes can be used to generate more replication-incompetent AAV for a further round(s) of screening or can be used for vectorization.

In other embodiments, the replication-incompetent AAV contains a genome with ITRs flanking a reporter gene operably linked to a first promoter, and a cap gene (e.g. from a capsid library) operably linked to a second promoter. In this embodiment, the target cells are transduced and cells are sorted (or selected) on the basis of reporter protein expression. RNA and optionally DNA are then extracted from the cells. The RNA is converted to cDNA and the capsid sequences are detected and recovered from the cDNA or DNA and then used to produce replication-incompetent AAV for a further round of selection (see e.g. FIG. 2). The plasmids and vectors containing this dual-promoter configuration are referred to in the Examples below as FT or FT2 plasmids or vectors, where FT and FT2 are the same except that the FT2 plasmids and vectors additionally utilise barcodes, as described further below.

For this dual-promoter embodiment to be effective without the need for barcodes, the promoters used to drive the expression of the cap and reporter genes must be functional in the host cells used for selection and under the conditions used for selection. For example, while AAV p40 promoters are generally used to drive expression of cap genes in AAV vector technologies and methods, such promoters have been described as being non-functional or inefficient in the absence of the Rep protein. Consequently, given that the functional transduction platforms described herein do not utilise Rep proteins in the selection process, in some instances the p40 promoter may not drive expression of the cap gene in transduced cells under selection conditions, resulting in no or little cap mRNA being produced and the inability to recover capsids from cDNA produced from the mRNA of transduced cells. However, in other instances, and as shown in the Examples below, the p40 promoter is functional even in the absence of Rep, and capsid sequences can therefore be recovered from cDNA produced from mRNA from transduced cells when the second promoter driving the cap gene is a p40 promoter. In other examples, the promoter used to drive the cap and/or reporter gene is a ubiquitous (i.e. functional in multiple tissue types or multiple host cells) and/or constitutive promoter.

Recovery of the cap gene can be performed by any manner known to those skilled in the art. Typically PCR amplification of the cap sequence is performed, such as by using primers specific for 5' and 3' regions of the cap gene, and/or primers specific for the regions flanking the cap gene, e.g. the promoter upstream of the cap gene and a 3' UTR downstream of the cap gene. The amplified cap genes can then be cloned into the appropriate construct and packaged to produce replication-incompetent AAV for a further round of selection. The selection process can be repeated a further 1, 2, 3, 4, 5, 6, 7, 8, 9, 10, 15, 20, 25 or more times before any one or more cap genes recovered in the process are vectorised.

Barcoded Genomes

In particular embodiments, the replication-incompetent AAV contains a barcode region downstream of the reporter gene, wherein the transcript expressed from the reporter gene contains the barcode region. Following transduction of target cells and cell sorting on the basis of reporter protein expression, DNA and RNA are extracted from the cells. The RNA is converted to cDNA and the barcode region in the reporter gene cDNA is detected and sequenced. By comparing the sequencing results to those obtained from the library before selection, barcode regions that have been enriched during the selection process can be identified and the cap genes contained in the same genome as those barcodes can be recovered. Advantageously, this embodiment enables RNA-based selection of cap genes where those cap genes are under the control of a promoter that does not function in the host cells used for selection, e.g. a p40 promoter, which is not functional in some host cells without the Rep protein present, or in any circumstances where any other promoter that can drive cap expression is silenced in the host cells. In this embodiment, rather than detecting expression of cap mRNA directly, functional transduction is assessed by detecting expression of reporter mRNA via barcode(s) downstream of the reporter gene.

The replication-incompetent AAV used in this process are similar to those described above. In one example, the AAV contain a genome with ITRs flanking a reporter gene operably linked to a first promoter, and a cap gene from a library operably linked to a second promoter. In another example, the single promoter embodiment can be used, where the AAV contains a genome with ITRs flanking a cap gene from a library and a reporter gene, where the cap gene and reporter gene are under the control of the same promoter but are separated by an IRES. Most typically, the vectors also contain a 3'UTR downstream of the cap gene and or a 5' UTR upstream of the cap gene. The reporter gene contains a barcode region, most typically at the 3' end, such that the RNA transcript generated by expression of the reporter gene includes the barcode region. This is shown schematically in FIG. 3. The barcode region contains at least one predetermined conserved sequence at the 3' end to which primers can be designed before the selection process takes place. Generally, within a library, the barcode region in each of the genomes has the same conserved sequence so that the same primer can be used to amplify each of the barcode regions. The barcode regions also contain at least one barcode that is unique, or at least partially unique, such that in any library (or plurality) of replication-incompetent AAV, at least two of the barcodes have a different sequence. Ideally, all of the barcodes have a different sequence, i.e. each is unique. Generally, at least 80%, 81%, 82%, 83%, 84%, 85%, 86%, 87%, 88%, 89%, 90%, 91%, 92%, 93%, 94%, 95%, 96%, 97%, 98% or 99% are unique, i.e. at least 80%, 81%, 82%, 83%, 84%, 85%, 86%, 87%, 88%, 89%, 90%, 91%, 92%, 93%, 94%, 95%, 96%, 97%, 98% or 99% of the AAVs in the library comprise a barcode with a unique (i.e. different) nucleic acid sequence relative to other barcodes in the library. The barcodes can therefore be used to "track" each of the AAV (and thus each of the cap genes in the library) through the selection process.

Following transduction and cell sorting on the basis of expression of the reporter protein, both the DNA and RNA are extracted and cDNA is produced from the RNA. The barcode region is amplified from the cDNA, such as using a primer specific for the conserved sequence in the barcode region and a primer specific for the reporter gene, and then sequenced to identify the barcode present in each of the genomes of the AAV that were able to functionally transduce cells. In preferred embodiments, next generation sequencing (NGS) is used to sequence the barcodes. Non-limiting examples of NGS include Illumina (Solexa) sequencing, Roche 454 sequencing, Ion torrent: Proton/PGM sequencing, and SOLID sequencing. Moreover, by comparing this sequencing data to sequencing data obtained before the selection process, those barcodes that have been enriched in the selection process can also be identified. Thus, in some embodiments, the methods also comprise sequencing the barcode regions prior to initiating the selection process. The frequency of each individual barcode in the library prior to the selection process is determined by sequencing the genomes (at the DNA level) of the AAV in the library. Following transduction, RNA and DNA extraction, RNA conversion to cDNA and sequencing of the barcode regions in the DNA and/or cDNA, as described above, barcodes that have increased in frequency compared to the frequency prior to selection, i.e. barcodes that have been enriched by the selection process, can be identified.

Figure 3:
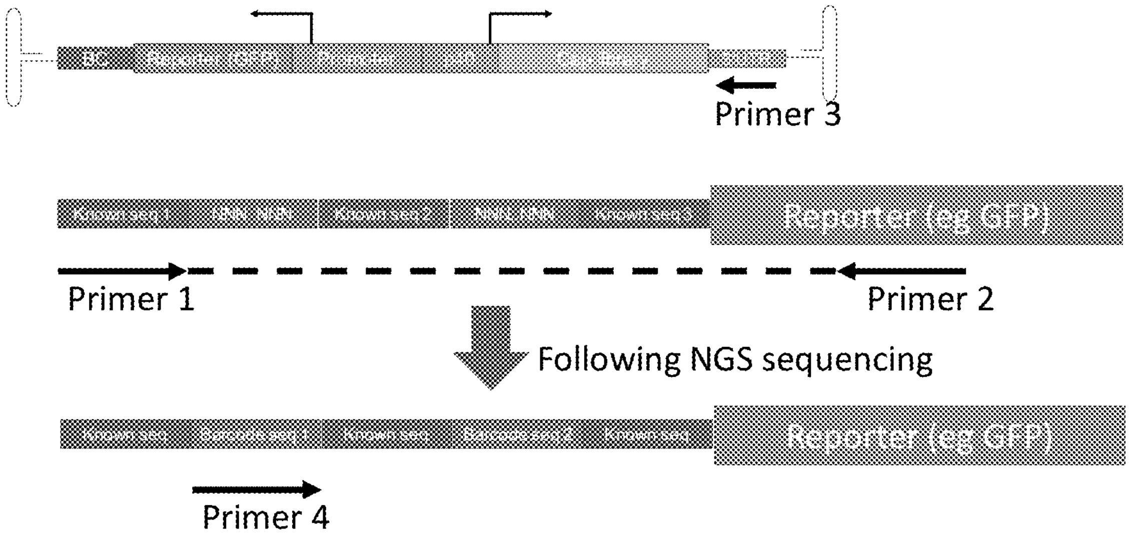
FIG. 3 is a schematic representation of the functional transduction platform using at least one barcode in the genome. In this embodiment, the reporter gene contains a barcode region (BC) containing at least one barcode at the 3' end of the reporter gene, such that it is expressed in the same transcript. Following transduction and sorting for cells expressing the reporter gene (e.g. GFP), both the DNA and RNA are extracted and cDNA is produced from the RNA. Using a primer specific for a conserved sequence in the barcode region (primer 1) and a primer specific for the reporter gene (primer 2), the barcode region is amplified and then deep-(Illumina)-sequenced to identify the barcode (Barcode seq 1) present in each of the genomes of the AAV that were able to functionally transduce cells. Primers specific for each of the identified barcodes are then designed (Primer 4) and used in combination with a primer specific for the 3'UTR (Primer 3) to amplify the genome of AAV that were able functionally transduce cells. The barcode region may also contain a further unique barcode (Barcode seq2), which can be used as an internal control. The cap genes are then recovered from the amplicons and can be used to generate a secondary replication-incompetent AAV library for a further round of screening or can be used for vectorization and evaluation of vector functions.

The genomes of the AAV that contain the identified barcodes are then amplified, such as by using primers specific for the identified barcodes and a primer specific for the 3'UTR. Recovery of the cap gene can be performed in any manner known to those skilled in the art. Typically PCR amplification of the cap gene is performed to recover the gene, such as by using primers specific for the second promoter and the 3'UTR which flank the cap gene. The amplified cap genes can then be cloned into the appropriate construct and packaged to produce replication-incompetent AAV for a further round of selection. FIG. 3 shows an exemplary embodiment of this functional transduction process. The selection process can be repeated a further 1, 2, 3, 4, 5, 6, 7, 8, 9, 10, 15, 20, 25 or more times before any one or more cap genes recovered in the process are vectorised.

The barcode region may also contain an additional barcode, which can be used as an internal control. As would be appreciated, it is possible that in any AAV library, one or more barcodes may have the same sequence. Accordingly, a second barcode may be included in the barcode region as an internal control so as to more accurately track and verify the identity of the AAV in the library.

An alternative functional transduction platform using two barcodes is also provided. The replication-incompetent AAV in the library used in this process contain a genome with ITRs flanking a reporter gene under the control of a first promoter and also having a barcode region at the 3' end, a cap gene from a library operably linked to a second promoter, a bacterial origin of replication, an antibiotic resistance gene and a second barcode region. The first and second barcode regions are at opposite ends of the genome and flank the reporter gene, the cap gene, the origin of replication and the antibiotic resistance gene. The first and second barcode regions contain at least one first and second barcode, respectively, and at least one known conserved sequence. Generally, at least 80%, 81%, 82%, 83%, 84%, 85%, 86%, 87%, 88%, 89%, 90%, 91%, 92%, 93%, 94%, 95%, 96%, 97%, 98% or 99% of the AAV in the library comprise a first barcode with a unique nucleic acid sequence relative to other first barcodes in the library, and at least 80%, 81%, 82%, 83%, 84%, 85%, 86%, 87%, 88%, 89%, 90%, 91%, 92%, 93%, 94%, 95%, 96%, 97%, 98% or 99% of the AAV in the library comprise a second barcode with a unique nucleic acid sequence relative to other second barcodes in the library.

Figure 4:
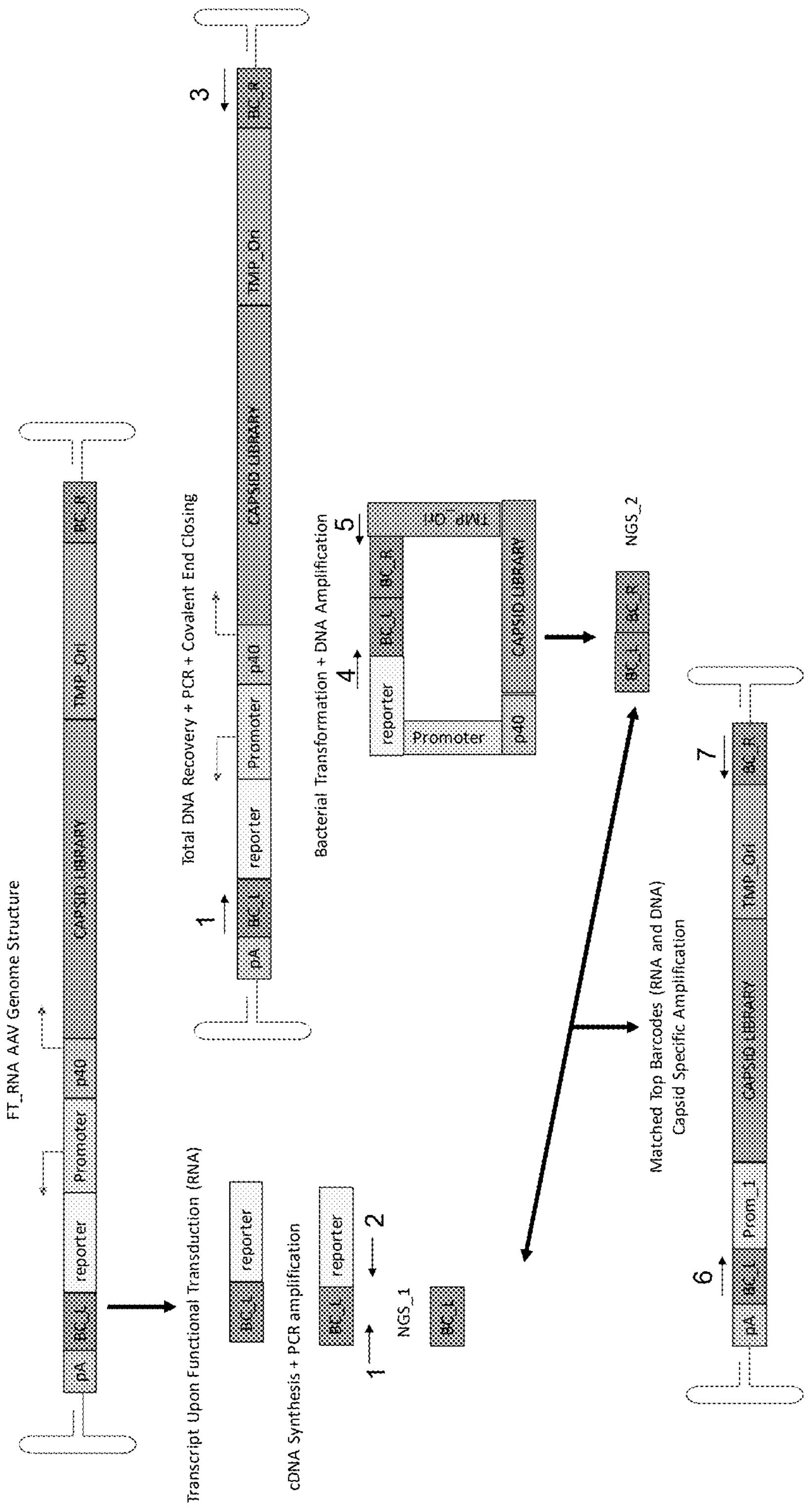
FIG. 4 is schematic representation of the functional transduction platform using barcodes. In this embodiment, the AAV genome comprises a genome comprising ITRs flanking a reporter gene (e.g. GFP) operably linked to a promoter, and a cap gene from a capsid library operably linked to a promoter (e.g. p40), an antibiotic resistance gene (e.g. trimethoprim (TMP)) and a bacterial origin of replication (Ori). There are two barcode regions that each contains at least one unique barcode: BC_L region which is fused to, or is part of, the reporter gene at the 3' end such that it is expressed in the same transcript, and BC_R region at the opposite end of the genome. Following transduction and sorting for cells expressing the reporter gene (e.g. GFP), both the DNA and RNA are extracted and cDNA is produced from the RNA. Using a primer specific for a conserved sequence in the BC_L region (primer 1) and a primer specific for the reporter gene (primer 2), the BC_L region is amplified and then sequenced to identify barcodes present in each of the genomes of the AAV that were able to functionally transduce cells. Primers specific for a conserved sequence in the BC_L region (primer 1) and primers specific for a conserved sequence in the BC_R region (primer 3) are used to amplify the whole genome from the extracted DNA before the resulting PCR product is ligated to form a plasmid, which is then transformed into bacteria to grow a plasmid library. The plasmid DNA is extracted and the BC_L and BC_R regions, which are adjacent one another, are amplified using primers 4 and 5, which are specific for regions in the reporter gene and TMP Ori. Sequencing is then performed on the resulting amplicons, which allows for identification of the barcode in BC_R that is present on the same genome as the barcode in BC_L identified from amplification and sequencing of the cDNA. Primers specific for each of the barcodes in the BC_L (primer 6) the BC_R (primer 7) are used to amplify the genome of AAV that were able to functionally transduce cells. The cap genes are then recovered from these amplicons and can be used to generate replication-incompetent AAV for a further round of screening or can be used for vectorization.

Following transduction and sorting for cells expressing the reporter gene, both the DNA and RNA are extracted and cDNA is produced from the RNA. The first barcode region is amplified from the cDNA, such as by using a primer specific for a known, conserved sequence in first barcode region and a primer specific for the reporter gene, and the amplicon is sequenced (such as using NGS as described above) to identify barcodes present in each of the genomes of the AAV that were able to functionally transduce cells. By comparing this sequencing data to sequencing data obtained before the selection process, those barcodes that have been enriched in the selection process can also be identified, as described above. At or near the same time, the genome is amplified from the extracted DNA, such as by using primers specific for a known, conserved sequence in the first barcode region and primers specific for a known, conserved sequence in the second barcode region. The resulting PCR product is circularised, such as by phosphorylation and ligation of the PCR produce ends, to form a plasmid, which is then transformed into bacteria to grow a plasmid library. The plasmid DNA is extracted and the first and second barcode regions, which are now adjacent one another, are amplified, such as by using primers specific for regions in the reporter gene and antibiotic resistance gene or origin of replication. Sequencing is then performed on the resulting amplicons, which allows for identification of the barcode in the second barcode region that is present on the same genome as the barcode in the first barcode region identified from amplification and sequencing of the cDNA. The genome of AAV that were able to functionally transduce cells is then amplified, such as by using primers specific for each of the identified barcodes in the first and second barcode regions. The cap genes are then recovered from these amplicons and can be used to generate replication-incompetent AAV for a further round of screening. The selection process can be repeated a further 1, 2, 3, 4, 5, 6, 7, 8, 9, 10, 15, 20, 25 or more times before any one or more cap genes recovered in the process are vectorised. FIG. 4 shows a schematic of a selection process using this type of functional transduction platform.

Nucleic Acid Molecules and Methods for Producing Replication-Incompetent AAV

The replication-incompetent AAV provided herein and used in the methods of the present disclosure are produced by packaging the AAV genomes broadly described above. Because the genomes lack a rep gene, this is provided in trans for packaging, along with Adenovirus helper functions or helper viruses.

Thus provided herein are nucleic acid molecules and methods for producing replication-incompetent AAV. The AAV are produced by introducing into a cell a first nucleic acid molecule comprising an AAV genome comprising two AAV ITRs flanking a reporter gene and a cap gene; a second nucleic acid molecule comprising a rep gene operably linked to a third promoter; and a third nucleic acid molecule comprising Adenovirus helper functions, or an helper virus; and culturing the cell under conditions suitable for packaging the genome, thereby producing replication-incompetent AAV. In some examples, the reporter gene and the cap gene are operably linked to a single promoter, and the reporter gene and the cap gene are separated by an internal ribosome binding site (IRES). In other examples, the reporter gene is operably linked to a first promoter and the cap gene is operably linked to a second promoter.

The reporter gene can be any that encodes a polypeptide or protein that can be directly detected using a suitable sorting process, or that can be indirectly-detected using a suitable sorting process, such as by using a labelled antibody that binds to the gene product. Examples of fluorescent agents include blue, cyan, green, yellow, orange, red, and far-red fluorescent protein. Examples of luminescent agents include e.g. luciferase proteins (such as firefly, *renilla, gaussia* luciferase). Examples of cell surface markers include molecules from the cluster of differentiation (CD), artificial epitopes or membrane-bound proteins from agents mentioned above such as fluorescent proteins. The reporter gene product can be truncated or a fusion protein. In a one embodiment, the reporter gene is a fluorescent protein, such as green fluorescent protein (GFP), including eGFP.

Other common fluorescent proteins such as other green and red fluorescent proteins (ZsGreen1, tdTomato, DsRed, AsRed, mStrawberry, mCherry, mOrange), yellow fluorescent proteins (YFP, mBanana, ZsYellow1), cyan fluorescent proteins (CFP, AmCyan1) or blue fluorescent proteins (BFP) or far-red fluorescent proteins (mKate2, HcRed1, mRaspberry, E2-Crimson, mPlum) may also be used. In addition, the reporter gene may encode fluorescent proteins with enhanced brightness such as eXFP, TagXFP or TurboXFP, wherein X may be any green, red, yellow, blue or far-red fluorescent protein as mentioned above.

An appropriate promoter for driving expression of the reporter gene and/or cap gene can be selected based on the configuration of the genome. As would be appreciated, the promoter that drives the expression of at least the reporter gene is one that functions in the host cells used for selection and under the conditions used for selection. Thus, where the configuration includes a single promoter, the promoter is one that functions in the host cells and under the conditions used for selection. Where the configuration includes two promoters, the promoter that drives expression of the reporter gene is one that functions in the host cells and under the conditions used for selection, and the promoter that drives expression of the cap gene may or may not be one that functions in the host cells and under the conditions used for selection. For example, and as described above, where selection is by direct amplification of the cap gene from DNA extracted from reporter-positive cells, or where barcodes downstream of the reporter gene are utilised so that selection can be based on reporter gene mRNA expression rather than cap mRNA expression, the promoter that drives expression of the cap gene does not need to be active in the host cells and/or under conditions used for selection.

Thus, in some examples, the promoter is ubiquitous and/or constitutive, e.g. the spleen focus forming virus (SFFV) promoter, the elongation factor-1 alpha promoter (EF-1$\alpha$), the short elongation factor-1 alpha promoter (EFS), Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the $\beta$-actin promoter, or the phosphoglycerol kinase (PGK) promoter, which can be of human or non-human origin. In other examples, the promoter is tissue specific. If the latter, then the promoter is selected based on the type of host cell that is being transduced in the selection methods. For example, where the methods are being used to select AAV that can functionally transduce hepatocytes, a liver-specific promoter may be used, such as, for example, the LSP promoter set forth in SEQ ID NO:6. Where the methods are being used to transduce cardiomyocytes, a cardiomyocyte-specific promoter such as cardiac troponin C (cTnC) may be used. In further examples, such as when the cap gene is under the control of a different promoter to the reporter gene, the promoter the drives expression of the cap gene is an AAV promoter, such as the p5, p19 or p40 promoter (such as one having a sequence set forth in SEQ ID NO:9).

The cap gene is typically from a cap library. Any AAV cap library can be used to source the cap genes, such as libraries based on shuffled DNA, error-prone PCR, or peptide display. Generally, the cap gene further contains a 3' UTR and/or a 5' UTR, such as a native AAV 3' UTR or 5' UTR as is known to those skilled in the art and routinely contained in AAV vectors.

Suitable IRESs to facilitate independent translation of the reporter gene and cap gene are well known in the art. Non-limiting examples include viral IRESs, such as those derived from Encephalomyocarditis virus, Foot and mouth disease virus, Rhinovirus, Hepatitis A virus, or Hepatitis C virus, and mammalian IRESs such as that derived from eukaryotic initiation factor 4G1.

In some embodiments, the reporter gene comprises a barcode region, such as at the 3' end of the gene. The barcode region contains at least one barcode. Typically, the barcode is a random sequence of at least 15, 16, 17, 18, 19, 20, 21, 22, 23, 24, 25, 26, 27, 28, 29, 30, 35, 40, 45, 50, 55, 60, 70, 80, 90 or more nucleotides. The barcode region may also include a conserved sequence at the 3' end of the region sufficient to design primers to. This conserved sequence is typically common to all barcode regions in a library, such that a single primer can be used to amplify all barcode regions in the library.

In particular embodiments, the first nucleic acid molecules contains a genome with ITRs flanking a reporter gene under the control of a first promoter and having a barcode region at the 3' end of the reporter gene, a cap gene from a library operably linked to a second promoter, a bacterial origin of replication, an antibiotic resistance gene and a second barcode region. The first and second barcode regions are at opposite ends of the genome and flank the reporter gene, the cap gene, the origin of replication and the antibiotic resistance gene. The first barcode region contains at least one first barcode, and the second barcode region contains at least one second barcode. Typically, the first and second barcodes are random sequences of at least 15, 16, 17, 18, 19, 20, 21, 22, 23, 24, 25, 26, 27, 28, 29, 30, 35, 40, 45, 50, 55, 60, 70, 80, 90 or more nucleotides. Each of the barcode regions may also include a conserved sequence to which oligonucleotides (or primers) can be designed. Where there is a plurality of nucleic acid sequences, the conserved sequence in the first barcode region is typically common to the plurality of first barcode regions, and the conserved sequence in the second barcode region is typically common to the plurality of second barcode regions.

AAV ITRs used in the nucleic acid molecules of the disclosure may have a wild-type sequence or may be altered, e.g., by the insertion, deletion or substitution of nucleotides. Additionally, AAV ITRs may be derived from any of several AAV serotypes, including without limitation, AAV1, AAV2, AAV3, AAV4, AAV5, AAV6, AAV7, AAV8, AAV9, AAV10, AAV11, AAV12 or AAV13. Such ITRs are well known in the art.

The AAV rep gene in the second nucleic acid molecule may have a wild-type nucleotide sequence or may be altered, e.g., by the insertion, deletion or substitution of nucleotides, provided it retains the ability effect AAV replication. Additionally, AAV rep may be derived from any of several AAV serotypes, including without limitation, AAV1, AAV2, AAV3, AAV4, AAV5, AAV6, AAV7, AAV8, AAV9, AAV10, AAV11, AAV12 or AAV13 and any variants thereof. In particular embodiments, the rep gene is from the same AAV serotype as the ITRs, and/or the same serotype as any AAV promoter used to drive expression of the cap gene in the first nucleic acid molecule.

As would be appreciated, a library of replication-incompetent AAV are produced when a plurality of the first, second and third nucleic acid molecules are introduced into a plurality of host cells. Thus, also provided are libraries of replication-incompetent AAV and pluralities of the first, second and third nucleic acid molecules (e.g., at least 10, $10^2$, $10^3$, $10^4$, $10^5$, $10^6$, $10^7$, $10^8$, $10^9$, $10^{10}$, $10^{11}$ or $10^{12}$ AAV or first, second and third nucleic acid molecules). In these embodiments, a plurality of cap genes having two or more different nucleic acid sequences is contained in the library or plurality. Generally, at least 80%, 81%, 82%, 83%, 84%, 85%, 86%, 87%, 88%, 89%, 90%, 91%, 92%, 93%, 94%, 95%, 96%, 97%, 98% or 99% of the first nucleic acid molecules, or the AAV, comprise a cap gene with a unique nucleic acid sequence relative to the other cap genes nucleic acid molecules or AAV. Similarly, when the reporter gene comprises a barcode, at least 80%, 81%, 82%, 83%, 84%, 85%, 86%, 87%, 88%, 89%, 90%, 91%, 92%, 93%, 94%, 95%, 96%, 97%, 98% or 99% of the first nucleic acid molecules or AAV comprise a barcode with a unique nucleic acid sequence relative to other barcodes. When the first nucleic acid molecule comprises a first barcode and a second barcode, at least 80%, 81%, 82%, 83%, 84%, 85%, 86%, 87%, 88%, 89%, 90%, 91%, 92%, 93%, 94%, 95%, 96%, 97%, 98% or 99% of the first nucleic acid molecules or AAV comprise a first barcode with a unique nucleic acid sequence relative to the other first barcodes, and a second barcode with a unique nucleic acid sequence relative to the other second barcodes.

Helper viruses and helper functions for AAV are known in the art. The helper functions may be provided by one or more helper plasmids or helper viruses comprising adenoviral helper genes. Non-limiting examples of the adenoviral helper genes include E1A, E16, E2A, E4 and VA, which can provide helper functions to AAV packaging. Helper viruses include, for example, viruses from the family Adenoviridae and the family Herpesviridae. Examples of helper viruses of AAV include, but are not limited to, SAdV-13 helper virus and SAdV-13-like helper virus described in US20110201088, helper vectors pHELP (Applied Viromics). A skilled artisan will appreciate that any helper virus or helper plasmid of AAV that can provide adequate helper function to AAV can be used herein.

Various types of cells can be used to package AAV. For example, packaging cell lines that can be used include, but are not limited to, HEK 293 cells, HeLa cells, and Vero cells, for example as disclosed in US20110201088.

Also provided are nucleic acid molecules for receiving cap genes from a library, and pluralities of these nucleic acid molecules (e.g., at least 10, $10^2$, $10^3$, $10^4$, $10^5$, $10^6$, $10^7$, $10^8$, $10^9$, $10^{10}$, $10^{11}$ or $10^{12}$). These nucleic acid molecules are essentially the same as the first nucleic acid molecules described above, although the lacking the cap gene. Accordingly, in one embodiment, the nucleic acid molecule comprises an AAV genome comprising two AAV ITRs flanking a reporter gene operably linked to a promoter, and an IRES. The genome typically contains one or more restriction enzyme sites upstream or downstream of the IRES, such that a cap gene can be inserted at the site(s) so that the cap gene and reporter gene are separated by the IRES but are operably linked to the same promoter. In another embodiment, the nucleic acid molecule comprises an AAV genome comprising two AAV ITRs flanking a reporter gene operably linked to a first promoter, wherein the reporter gene comprises a first barcode. The genome typically contains a second promoter that will drive expression of the cap gene once inserted. The genome may therefore include a second promoter and one or more restriction enzymes sites configured such that upon insertion of a cap gene at the one or more restrictions enzymes sites, the cap gene will be operably-linked to the second promoter. In further embodiments, the genome comprises a 3'UTR and/or a 5' UTR downstream or upstream, respectively, of the restrictions enzymes site(s) so that the UTR is positioned upstream or downstream of the cap gene when inserted. Where there is a plurality of nucleic acid molecules, at least two of the nucleic acid molecules comprises a first barcode with a unique nucleic acid sequence relative to other first barcodes in the plurality. Generally, at least 80%, 81%, 82%, 83%, 84%, 85%, 86%, 87%, 88%, 89%, 90%, 91%, 92%, 93%, 94%, 95%, 96%, 97%, 98% or 99% of the nucleic acid molecules in the plurality comprise a first barcode with a unique nucleic acid sequence relative to other first barcodes in the plurality.

In another embodiment, the nucleic acid molecule comprises an AAV genome comprising two AAV ITRs flanking a reporter gene operably linked to a first promoter, wherein the reporter gene comprises a barcode at the 3' end; a bacterial origin of replication; an antibiotic resistance gene;

and a second barcode, wherein the first and second barcodes are at opposite ends of the genome and flank the reporter gene, the origin of replication and the antibiotic resistance gene. The genome typically contains a second promoter that will drive expression of the cap gene once inserted. The genome may therefore include a second promoter and one or more restriction enzymes sites configured such that upon insertion of a cap gene at the one or more restrictions enzymes sites, the cap gene will be operably-linked to the second promoter. In further embodiments, a 3'UTR is downstream of the restriction enzymes sites.

The nucleic acid molecules can also include transcriptional enhancers, translational signals, and transcriptional and translational termination signals. Examples of transcriptional termination signals include, but are not limited to, polyadenylation signal sequences, such as bovine growth hormone (BGH) poly(A), SV40 late poly(A), rabbit beta-globin (RBG) poly(A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence. In other embodiments, introns are included in the nucleic acid molecules, such as between a promoter and an operably linked gene.

In particular embodiments, the nucleic acid molecules are plasmids.

AAV Vectors

Also contemplated are methods for producing AAV vectors using the cap genes identified according to methods described herein, and the resulting AAV vectors themselves. Methods for vectorizing a capsid protein are well known in the art and any suitable method can be employed for the purposes of the present disclosure. For example, the cap gene can be recovered (e.g. by PCR or digest with enzymes that cut upstream and downstream of cap) and cloned into a packaging construct containing rep. Typically, the cap gene is cloned downstream of rep so the rep p40 promoter can drive cap expression. This construct does not contain ITRs. This construct is then introduced into a packaging cell line with a second construct containing a transgene flanked by ITRs. Helper function or a helper virus are also introduced, and recombinant AAV comprising a capsid generated from capsid proteins expressed from the cap gene, and encapsidating a genome comprising the transgene flanked by the ITRs, is recovered from the supernatant of the packaging cell line. Various types of cells can be used as the packaging cell line. For example, packaging cell lines that can be used include, but are not limited to, HEK 293 cells, HeLa cells, and Vero cells, for example as disclosed in US20110201088. The helper functions may be provided by one or more helper plasmids or helper viruses comprising adenoviral helper genes. Non-limiting examples of the adenoviral helper genes include E1A, E16, E2A, E4 and VA, which can provide helper functions to AAV packaging. Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US20110201088, helper vectors pHELP (Applied Viromics). A skilled artisan will appreciate that any helper virus or helper plasmid of AAV that can provide adequate helper function to AAV can be used herein.

In some instances, rAAV virions are produced using a cell line that stably expresses some of the necessary components for AAV virion production. For example, a plasmid (or multiple plasmids) comprising the nucleic acid containing a cap gene identified as described herein and a rep gene, and a selectable marker, such as a neomycin resistance gene, can be integrated into the genome of a cell (the packaging cells). The packaging cell line can then be transfected with an AAV vector and a helper plasmid or transfected with an AAV vector and co-infected with a helper virus (e.g., adenovirus providing the helper functions). The advantages of this method are that the cells are selectable and are suitable for large-scale production of the recombinant AAV. As another non-limiting example, adenovirus or baculovirus rather than plasmids can be used to introduce the nucleic acid encoding the capsid polypeptide, and optionally the rep gene, into packaging cells. As yet another non-limiting example, the AAV vector is also stably integrated into the DNA of producer cells, and the helper functions can be provided by a wild-type adenovirus to produce the recombinant AAV.

As will be appreciated by a skilled artisan, any method suitable for purifying AAV can be used in the embodiments described herein to purify the recombinant AAV, and such methods are well known in the art. For example, the recombinant AAV can be isolated and purified from packaging cells and/or the supernatant of the packaging cells. In some embodiments, the AAV is purified by separation method using a CsCl gradient. In other embodiments, AAV is purified as described in US20020136710 using a solid support that includes a matrix to which an artificial receptor or receptor-like molecule that mediates AAV attachment is immobilized.

Compositions, Combinations and Kits

Also contemplated herein are compositions comprising any one or more of the replication-incompetent AAV, AAV vectors or nucleic acid molecules described above and herein; combinations comprising any one or more of the replication-incompetent AAV, AAV vectors or nucleic acid molecules described above and herein, and host cells comprising any one or more of the replication-incompetent AAV, AAV vectors or nucleic acid molecules described above and herein.

Also provided are kits, such as for use in the methods of the disclosure for producing replication-incompetent AAV and for selecting cap genes for vectorization. The kits therefore may include any one or more of the nucleic acid molecules described above and herein, optionally with instructions for use. Primers suitable for amplification of regions of the nucleic acid molecules may also be included in the kit, such as a primer specific for conserved sequences in one or more barcode regions, a primer specific for the second promoter (i.e. the promoter driving a cap gene), a primer specific for the reporter gene, and/or a primer specific for a 3'UTR.

In order that the invention may be readily understood and put into practical effect, particular preferred embodiments will now be described by way of the following non-limiting examples.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1. Materials and Methods

Plasmids and Libraries

Plasmids for functional transduction studies were constructed to contain AAV2 ITRs (SEQ ID NOs: 2 and 3) flanking eGFP (SEQ ID NO: 4) with a SV40 polyA sequence (SEQ ID NO: 5) under the control of the LSP promoter (SEQ ID NO: 6), EF1a short promoter (SEQ ID NO: 7) or SFFV promoter (SEQ ID NO: 8) and a cap gene under the control of the p40 promoter (SEQ ID NO: 9, representing a fragment of the rep gene containing the p40 promoter). Introns between the promoters and operably linked genes can be included, such as the wild-type AAV intron between the p40 promoter and the cap gene, and a SV40 intron (SEQ ID NO:10) between the eGFP gene and promoter driving it. Two unique restriction sites (SwaI/NsiI) flanking the cap gene facilitate the cloning of other cap genes from AAV libraries carrying these sites. An exemplary plasmid is FT-LSP-AAV2 (FIG. 5) having the sequence set forth in SEQ ID NO:1. This exemplary plasmid includes a cap gene from a library.

Figure 10:
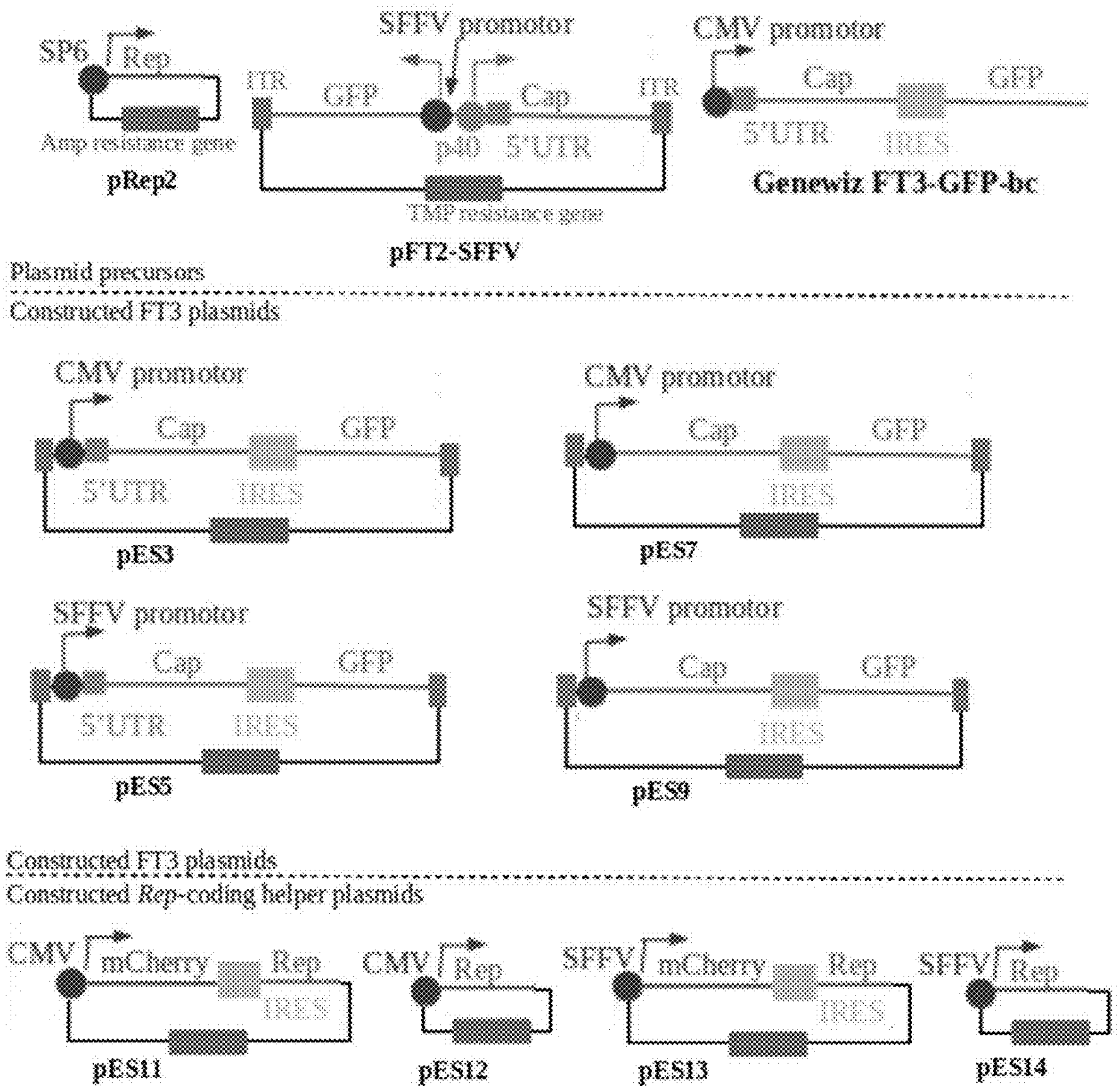
FIG. 10 is a schematic of the plasmids used for the FT3 platform.

The FT3-GFP-bc construct was designed in silico and ordered from Genewiz. The FT3-GFP-bc construct contained, from 5' to 3', a CMV enhancer and promoter (SEQ ID NOs:34 and 15, respectively), a 5' UTR (SEQ ID NO:35), a cap gene with unique SwaI/NsiI sites (see above) (Ico6; SEQ ID NO:33), an IRES of encephalomyocarditis virus (EMCV) (SEQ ID NO:16) and eGFP, and was cloned into a plasmid containing AAV2 ITRs (pSL388) using EcoRV. A TMP resistance gene, bcDHFR, was inserted into the plasmid to obtain pES3. pES3 was digested by Swa1 and BsaB1 to remove the cap 5'UTR, then religated to produce pES7. The CMV enhancer/promoter was replaced with the SFFV promoter through BsiW1 and Mlu1 digestion of pES3 and pES7, producing pES5 and pES9 (FIG. 10).

Other plasmids used in the studies included the FT2-SFFV plasmid, in which the cap gene is under the control of the p40 promoter and eGFP is under the control of the SFFV promoter; the vHTE plasmid, in which both the cap and eGFP genes are under the control of the SFFV promoter but are separated by the EMCV IRES; and the eHTE plasmid, in which both the cap and eGFP genes are under the control of the SFFV promoter but are separated by the eukaryotic initiation factor 4G1 (eIF4G1) IRES (SEQ ID NO:17). Schematic representations of these plasmids are provided in FIGS. 12 and 13.

A plasmid containing the rep gene from AAV2/2 (referred to as AAV2 for simplicity) with a polyA sequence (SEQ ID NO:11) and under the control of the endogenous p5 promoter (SEQ ID NO:12) was also produced and named p-Rep2-polyA. Other rep-containing plasmids included pES11, which contained mCherry (SEQ ID NO: 18) and rep, separated by the IRES of EMCV, under the control of the CMV promoter; pES12, which contained rep under the control of the CMV promoter; pES13, which contained mCherry and rep, separated by the EMCV IRES, under the control of the SFFV promoter; and pES14, which contained rep under the control of the CMV promoter (FIG. 10).

Functional transduction libraries were produced by inserting cap genes from capsid libraries into plasmids at the SwaI/NsiI sites. Library nucleic acid was amplified in competent bacteria cells and was purified using commercially available plasmid extraction kit and then packaged as essentially described below with supplementation of 7.5 μg/plate of the p-Rep2-polyA plasmid.

AAV Production

AAV Production with Purification by Caesium Chloride Gradient

AAV libraries were packaged on 60×15 cm tissue culture dishes containing 90-95% confluent HEK 293 cells (ATCC, catalogue no. CRL-1573). Briefly, 22.5 μg of the Adenovirus 5 helper plasmid and 15 μg of the AAV plasmid library were transfected in each of the 60 plates, by mixing the total 37.5 μg of DNA with 75 μg (ratio DNA:PEI 1:2) of polyethylenimine (PEI, MW 25000, Polysciences 23966-2) in a total volume of 500 μL of OptiMEM media (Life Technologies). 72 h post transfection cells were harvested and centrifuged at 3800 rpm for 15 min. From here media and cells were treated separately. The supernatant was re-spun and incubated 3 hours on ice with ¼ volume of 40% Polyethylene Glycol (PEG) 8000 (Fisher Scientific, BP2331-1KG). After incubation, the solution was centrifuged (3800 rpm, 4°) and PEG-pellet containing the AAV particles was resuspended in 20 mL of Cracking Buffer (10 mM Tris, pH-7.5, 0.15M NaCl, 10 mM MgCl2) over-night. On the other hand the cell pellet from the first spin was resuspended in 35 mL of Benzonase Buffer (50 mM Tris, pH 8.5, 2 mM CsCl2) and three cycles of freeze-thawing were carried out by submerging the suspension in dry ice/ethanol. After the 3rd thaw Benzonase (EMD Chemicals, Merck, 1.01695.0002) was added at a concentration of 200 U/mL and solution was incubated one hour at 37° C. Cell suspension was then centrifuged to discard cell debris. Supernatant was moved to a new 50 mL Falcon and ⅓₉th volume of 1M CaCl2) was added and kept on ice for one hour. The solution was then centrifuged again and supernatant was transferred to a new tube and incubated 3 hours on ice with ¼ volume of 40% PEG 8000 and spun at 3800 rpm 4° C. and pellet containing AAV particles was resuspended in 20 mL of Resuspension Buffer (50 mM Hepes, pH 7.4, 0.15M NaCl, 25 mM EDTA) over-night. Cesium Chloride (CsCl, Ultrapure optical grade, Life Technologies, 15507-023) gradient centrifugation was then carried out for the media and cell suspensions independently. Briefly, 12 mL of 1.3 g/mL CsCl in Dulbecco's Phosphate Buffered Saline (Sigma Aldrich, D8537) were added to Ultra-Clear Centrifuge Tube (Beckman Coulter, 344058). 5 mL of 1.5 g/mL CsCl in PBS were added then to the bottom of the tube to establish a clear interface. The 20 mL of the cell and media vector solutions were then added to the top of the gradient and both fractions were spun in a SW32 Ti Rotor at 25K (106,800 g) at 20° C. for 24 hours. Vector fractions laying in between the two distinct density solutions were then collected using a 10 mL syringe/18G needle. Both fractions were pulled together at this stage and a second ultracentrifugation in a CsCl solution (1.37 g/mL) was then carried out. 12 mL of the CsCl solution were added in a centrifuge tube (BeckmanCoulter, 331372) and spun at 38K in a SW41 Ti rotor (247,600 RCF) for 24 hours. 0.5 mL fractions were collected from the second spin and fractions with highest amounts of AAV DNA were determined by quantitative polymerase chain reaction (qPCR). The top six fractions were then pulled and dialyzed in order to eliminate the excess of CsCl. The AAV solution was loaded into a slide-a-lyzer dialysis cassette (10.000 MWCO, 3.0 mL capacity, Thermo Fisher, 87730) and two initial dialyses were carried out for 33 24 hours in 2 L of PBS at 4° C. A 3rd additional dialysis was then carried out in 5% Sorbitol in PBS for 3 hours at 4° C. AAV particles were then removed from the dialysis cassette and filtered through a 0.22 μm syringe filter (Merck Millipore, SLGP033RS). Finally, the 3 mL of vector solution were concentrated to 1 mL with a Amicon Ultra-15 Centrifugal Unit (NMWL of 100 kDa, Merck Millipore, UFC910024).

AAV Production with Purification by Iodixanol Gradient

Indicated AAV libraries and AAV preparations were packaged on 5×15 cm tissue culture dishes containing 90-95% confluent HEK 293 cells (ATCC, catalogue no. CRL-1573). Briefly, 22.5 μg of the Adenovirus 5 helper plasmid and 15 μg of the AAV plasmid library were transfected in each of the 5 plates, by mixing the total 37.5 μg of DNA with 75 μg (ratio DNA:PEI 1:2) of polyethylenimine (PEI, MW 25000, Polysciences 23966-2) in a total volume of 500 μl of OptiMEM media (Life Technologies) per plate. 72 h post transfection cells were harvested and centrifuged at 3800 rpm for 15 min. From here media and cells were treated separately. On one hand supernatant was re-spun and incubated 3 hours on ice with ¼ volume of 40% Polyethylene Glycol (PEG) 8000 (Fisher Scientific, BP2331-1KG). After incubation, the solution was centrifuged (3800 rpm, 4°) and PEG-pellet containing the AAV particles was resuspended in 2 mL of PBS Buffer (pH 8.0). Separately, cell pellet was resuspended in 3 mL of PBS buffer (pH 8.5) and cells were lysed using 3 freeze/thaw cycles by placing the solution at −80° C. (dry ice+ethanol) and back at 37° C. (water bath). The resuspended PEG pellet and the cell lysate were then mixed and incubated with Benzonase (200 U/mL) 1 h at 37° C. 10% sodium deoxycholate was added to a final concentration of 0.5% and subsequently ¼ volume of 5M NaCl to a final concentration of 1M. Solution was incubated for 30 minutes at 37° C. (water bath) and spun 30 minutes at 3800 rpm at 4° C. Virus supernatant was collected into a 5 mL Eppendorf tube.

The four solutions required for iodixanol gradient (15%, 25%, 40% and 60%) were prepared. The 15% solution was added to the bottom of the Beckman tube using a 10 mL syringe with a long 18-gauge metal cannula. Subsequent layers were added below the previous layer (25%->6 mL; 40%->5 mL; 60%->5 mL) by extending the syringe needle to the bottom of the Beckman tube and slowly injecting.

The recovered virus supernatant was then carefully added to the top of the gradient by slowly dripping the solution using a 5 mL pipette and avoiding disruption of the gradient layers. The remaining void of the Beckman tube was filled with balancing buffer and tubes were balanced within 0.01 g. The vector preparation(s) were centrifuged at 58.000 rpm in a Beckman Type 70Ti rotor for 2 hours and 10 minutes at 18° C. using a Beckman Coulter XPN ultracentrifuge set a 3 for acceleration and at 9 (slowest) for deceleration. After centrifugation, tubes were carefully removed and mounted on a ring stand with a utility clamp back to the tissue culture hood. Tube surface was cleaned with 70% ethanol and a 10 mL syringe with an 18-gauge needle was prepared for viral extraction upon accurate insertion approximately 1.5 mm below the interface between the 40% and 60% gradient buffer layers, with the bevel of the needle facing up. 3 to 5 mL of solution were then extracted, first with the bevelled needle opening facing upwards and then facing downward, avoiding the collection of the visible protein-rich band at the 25/40% interface.

The 3-5 mL virus preparation were then filtered with a 0.22 μm PES filter and mixed with Iodixanol Dialysis Buffer, to a total volume of 15 mL. Total volume was then moved to a 100K Amicon Ultra-4 Centrifuge Filter tube and centrifuged at 3800 rpm at 18° C. for 2-6 minutes to bring the volume down to desired volume, usually 200 to 500 μl. 15 mL of Iodixanol Dyalisis Buffer were then added and centrifuged again. This step was repeated two more times and final 200-500 μl of vector preparation were extracted from the Amicon Tube to a large cryovial tube and stored at 4° C. for short-term storage or at −80° C. for long-term storage.

Vector Titration qPCR was performed using standard protocols. Dilutions of 1/10 and 1/100 were used for media, and dilutions of 1/100 and 1/1000 were used for cell lysates. Primers used included SC010 and SC011 (targeting GFP). Cycle: 98° C. 2 min, 39 times 98° C. 5 s+60° C. 15 s, 65° C. 30 s, melting curve from 65° C. to 95° C. by adding 0.5° C. each 5 s. Titers were averaged on the 6 measures done for each sample (2 dilutions×3 replicates) and the lysate titer was added to the media titer to obtain total titer.

In Vitro Selection of Functional Transduction AAV Libraries (DNA Based)

Different concentrations of the packaged library were initially tested on the cell type of interest in order to determine the AAV library concentration that leads to 0.5-2.5% of GFP+ population 72 hours post-transduction. 8 hours post-transduction, the cells were washed with PBS and fresh media was added. Once the correct concentration was determined, the transduction process was scaled up to allow sufficient cell yield upon fluorescent activated cell sorting (FACS) to identify GFP positive cells.

Sorted cells were collected and pelleted upon centrifugation, resuspended in DNA extraction buffer containing Proteinase K and left over-night at 56° C. Total DNA was extracted following a Phenol/Chloroform/Isoamyl Alcohol protocol. Briefly, 200 μL of DNA was mixed with an equal volume of the phenol/chloroform/isoamyl alcohol solution and mixed vigorously for 1 minute before being spun at high speed for 5 minutes on a bench-top centrifuge. Approximately 180 μL of the top aqueous solution was then removed and placed in a new tube, avoiding any of the chloroform/isoamyl alcohol phase.

Ethanol precipitation was then performed. Briefly, sodium acetate was added to the DNA solution to a final concentration of 0.75 M to precipitate. The solution was mixed thoroughly before 2.5× volume of 100% ethanol was added and mixed. The solution was left at −80° C. for 30 min and then spun for 20 min in a 4° C. centrifuge at top speed. Supernatant was decanted carefully without disturbing the pellet, which was washed by adding 300 μL of 80% ethanol and vortexed 3 times. The solution was subsequently spin again for 15 min in a 4° C. centrifuge at top speed and the supernatant was carefully removed. The DNA pellet was air dried for 1-2 minutes at room temperature, and residual ethanol was removed with a pipette. The DNA was then re-suspended with the appropriate volume of water.

100 ng of purified DNA was then used to PCR recover the enriched capsids using Q5 polymerase, Cap-Rescue F primer (SEQ ID NO:13) and Cap-Rescue R primer (SEQ ID NO:14) and the following thermocycler conditions: 1) 30 sec-98° C., 2) 10 sec-98° C., 3) 60° C.-10 sec, 4) 72° C.-1.10 min, 5) 2×35 times, 6) 72° C.-5 min. The PCR product was then excised with Zymoclean Gel DNA Recovery Kit (Zymogen Cat #D4001T) and cloned into the recipient plasmid upon Gibson Assembly.

Library Gibson Assembly (GA) and Library Restriction Cloning

GA reactions were performed by mixing an equal volume of 2× Gibson Assembly Master Mix (NEB Cat #E2611 L) with 1 pmoL of PCR amplified and DpnI treated receptor plasmid (pWK4) and 1 pmol of the recovered capsids, at 50° C. for 30 min. DNA was ethanol precipitated and electroporated into SS320 electro-competent *E. coli* (Lucigen Cat #60512-2). The total number of transformants was calculated by preparing and plating five 10-fold serial dilutions of the electroporated bacteria. The pool of transformants was grown overnight in 250 mL Luria-Bertani media supplemented with trimethoprim (10 μg/mL). Total plasmids were purified with an EndoFree Maxiprep Kit (QIAGEN Cat #12362) and subsequently digested overnight with SwaI and NsiI. 1.4 μg of insert was ligated at 16° C. with T4 DNA ligase (NEB Cat #M0202) for 16 hours into 1 μg of a replication-competent AAV2-based plasmid platform or into 1 μg of a functional transduction AAV2-based plasmid platform (e.g. FT LSP AAV2, described above). Ligation reactions were concentrated by using ethanol precipitation, electroporated into SS320 electro-competent bacteria and grown as described above. Total plasmids were purified with an EndoFree Maxiprep Kit (QIAGEN Cat #12362).

Dilution and Cross-Packaging Studies

Primers VG660 and VG661 were designed for mutagenesis of the Ico6 gene. These primers bind to the region surrounding the mutation site and include the mutation (wild-type codon 588: AGC; mutated codon: TGA). The primers were used to PCR amplify Ico6 while introducing the mutation. NEBuilder was used to reconstitute a circular plasmid out of the PCR product. The mutated cap gene, called Ico6 stop, was then cloned into a pES5 (also called vHTE-SFFV) backbone. The same overall method was also used to generate Cap2_Y567*.

Transfection was performed using standard polyethlenimine protocols. 1:1 mixes of Cap2 and Cap2_Y567* in the RC, FT and eHTE platforms at plasmid to cell ratios of 25000, 10000, 5000, 1000 and 500 transgene plasmids/cell were used for transfection of twelve 15 cm dishes of HEK293T cells. 1:1 mixes of Cap6 and Cap6 S588* in the vHTE platform at plasmid to cell ratios of 25000, 8000, 5000, 1000 and 500 transgene plasmids/cell were used for transfection of twelve 15 cm dishes of HEK293T cells. Vector production and titration were performed as described above except for the quantities of vector plasmids transfected. For NGS (next generation sequencing) of cap genes present in capsids, 1 μL of cell lysate was mixed with 1 μL of media. Capsids were opened by addition of 9 μL alkaline digestion buffer (25 mM NaOH, 0.2 mM EDTA), incubation 10 min at 99° C., then 9 μL neutralization buffer (40 mM Tris-Hcl, pH=5.0, 0.05% Tween20) were added. 2 μL of the obtained solution were used as a template for PCR amplification of a 133 bp region of cap gene in which is located the mutation site, using primers VG619 and VG620 for vHTE (Ico6) cross-packaging analysis and VG0896 and VG0897 were used to analyse the crospackaging of Cap2 in the RC, FT and eHTE platforms. PCR products were purified using Zymo research's Zymoclean Gel DNA Recovery Kit protocol and 1 μg was sent to Genewiz SZ NGS laboratory for NGS.

RNA Extraction and Reverse Transcription (RT)

RNA was extracted from pelleted cells following Zymoclean's direct-zol RNA microprep protocol. To further purify RNA, 3 μg of RNA were incubated 3 h at 37° C. with 4 units of NEB's DnaseI #M03003 L and NEB's DNaseI buffer #B0303S 10× (20 μL total). DNase was heat-inactivated 15 min at 70° C. Random hexamers 10× and dNTP (to a final concentration of 1 mM) were added to the RNA solution 5 min at 65° C. in order to anneal primers to RNA, then the solution was kept on ice and split in two samples for RT (incubation 10 min 53° C. than 10 min 80° C.). Sample RT+: for 20 μL, add SSIV buffer 5×, 2 μL DTT, 2 μL Dnase inhibitor and 2 μL superscript RT. Sample RT−: for 10 μL, add SSIV buffer 5×, 1 μL DTT, 1 μL Dnase inhibitor and 1 μL superscript RT. 1/16th volume of *E. coli* RnaseH was added and the solution was incubated 20 min at 37° C. Primer annealing, RT and RNA digestion were performed with Invitrogen's SuperScript IV reagents.

Helper-Free Transgene Expression

HEK293T cells were transfected with $2.5\times10^4$ vector plasmids per cell, without helper plasmid. After 72 h incubation, around 3 million cells are harvested and centrifuged for 20 min at 3800 g, then the supernatant was discarded. RNA extraction and RT were performed as described above. qPCR was performed for both RT+ and RT− samples (the latter being a negative control for RNA purification and RT) with 3 dilutions (1:10, 1,100 and 1:1000), and with water as negative control. Two sets of primers were used: VG760 and VG761 target the cap transcripts whereas VG693 and VG694 target human β actin, a housekeeping gene used as a reference. qPCR cycle: 98° C. 2 min, 39 times 98° C. 5 s+60° C. 15 s, 65° C. 30 s, melting curve from 65° C. to 95° C. by adding 0.5° C. each 5 s. Relative expression levels (written R) were computed as following: $R=2^{Ct(ref)-Ct(sample)}$, where Ct(sample) is a number corresponding to the number of amplification cycles after which sample fluorescence starts to increase strongly, and computed automatically by the qPCR software; and Ct(ref) is the same number but for the cognate reference sample (where β actin is amplified).

Capsid Recovery (RNA Based Selection Studies)

RNA was extracted from transduced cells and RT was performed as described above. Cap cDNA is PCR-amplified using primers VG688 and VG689 (for AAV1, 5 or 6) or VG732 (for AAV2, 3, 7, 8, 9 or 10); primer annealing temperature between 64 and 65° C.). pWK4-rna was PCR-opened with primers VG690 and VG691 (primer annealing temperature between 58 and 62° C.). Both amplicons were gel extracted and open pWK4-rna was digested by DpnI to eliminate residual non-open plasmid. Cap cDNA and DpnI-digested open pWK4-rna were ligated by NEBuilder to build a circular pWK4-rna plasmid containing the desired Cap. This plasmid can be used for further cloning, for example excising the recovered capsids with SwaI/NsiI and ligating them into any of the herein described selection platforms RC, FT, FT2, FT3 (HTE).

Example 2. Packaging Efficiency of Functional Transduction Plasmid

Figure 6:
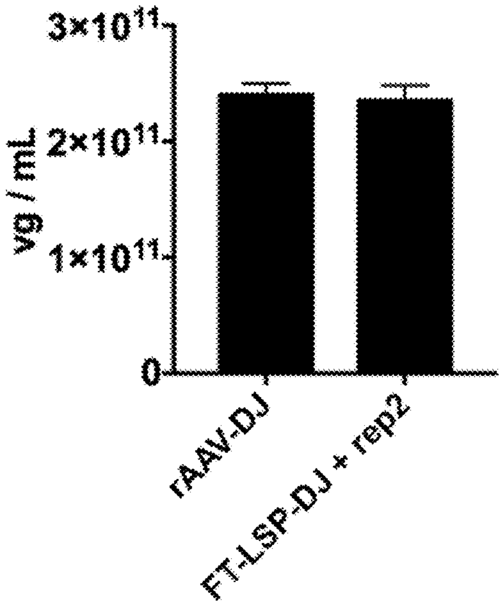
FIG. 6 shows the packaging efficiency of the functional transduction construct containing ITRs flanking the GFP reporter gene and the AAV-DJ cap gene under the control of the p40 promoter (FT-LSP-DJ) following transfection into HEK293T cells. Since FT-LSP-DJ doesn't contain AAV Rep gene, plasmid encoding Rep was provided in trans during vector packaging (indicated as "+rep2"). Canonical packaging construct encoding Rep2 and cap DJ was used as a control (rAAVDJ). The number of vector genomes (vg) per mL is shown.

In order to test the packaging efficiency of the functional transduction construct, the cap sequence of AAV-DJ was cloned into the plasmid as a proxy of a complex capsid library and its packaging efficiency tested by providing the rep gene on a separated plasmid in trans. HEK293T cells were co-transfected with the Functional Transduction construct containing the ITRs, GFP under the control of Liver Specific Promoter (LSP) and AVV-DJ cap (ITR-LSP-GFP-DJ-ITR), the rep plasmid (pRep2-PolyA) and the plasmid providing the Adenovirus helper functions (pAd5). Constructs for rAAV-DJ were also transfected for comparison. No difference in titre between the functional transduction platform construct and the canonical recombinant AAV-DJ was observed (FIG. 6).

Figure 7:
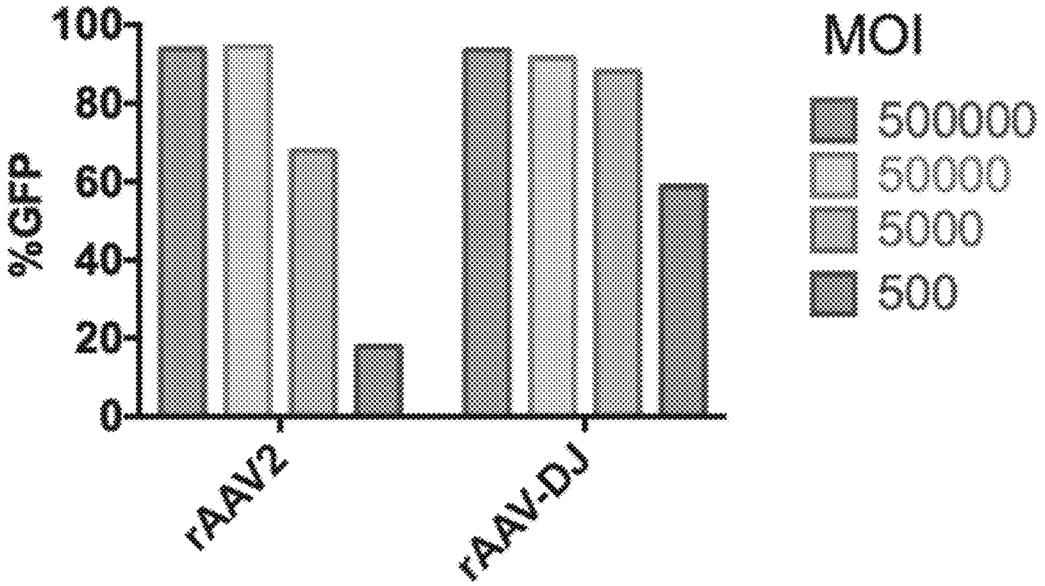
FIG. 7 shows the transduction efficiency of rAAV2 and rAAV-DJ (each containing a GFP reporter gene) in HuH7 cells at different multiplicities of infections (MOIs). The percentage of cells that were GFP positive is shown.

Example 3. Comparison of Function Transduction Platform and Replication-Competent Platform AAV-DJ is a synthetic serotype identified through a process of iterative selection of an AAV library via DNA-family shuffling. Synthetic (also termed "bioengineered") capsids and vectors have been modified by, for example, shuffling or rational designs, so as to alter one or properties of the capsid or vector, e.g. tropism, transduction efficiency, etc. AAV-DJ is very efficient at functionally transducing HuH-7 cells, as well as many other cell lines (Grimm et al. *J Virol.* 2008, 82(12):5887-911). AAV2 vectors functionally transduce HuH-7 efficiently at high MOIs, although at lower titres AAV-DJ outperforms AAV2 (FIG. 7). These two AAV vectors were therefore used to test the ability of the functional transduction platform to more efficiently select vectors with strong functional transduction.

Cap genes from wild-type AAV2 and AAV-DJ were cloned into the canonical platform based on replication-competent virions (RC-AAV2 and RC-AAV-DJ) and the functional transduction platform (FT-AAV2 and FT-AAV-DJ). The four constructs were then packaged independently and the respective AAV2 and AAV-DJ were combined equimolarly based on qPCR titre data to form the RT (AAV2+AAV-DJ) and FT (AAV2+AAV-DJ) mini-libraries. Once the two 'mini' libraries were generated, selection of each "mini" library was performed on Huh7 cells so as to determine which platform allowed for faster (i.e. within less rounds) selection of AAV-DJ (FIG. 8A).

The functional transduction selection was first optimised by transducing HuH-7 cells with different MOIs of FT-Li-AAV2/FT-Li-AAV-DJ. The fact that this system encodes for a transduction marker provides a convenient way to test various doses of the library and a way to choose the dose that gives an optimal balance between stringency and practicability or, in other words, low but sufficient percentage of GFP to allow for sorting sufficient number of cells to perform PCR capsid recovery. It was found that for the tested mini-library, a MOI of 50 for the FT-Li-AAV2/FT-Li-AAV-DJ gave 2.6% of GFP positive cells 72 hours after transduction. In order to be able to compare the platforms, HuH7 cells were infected at the same MOI with the replication competent RC-Li-AAV2/RC-Li-AAV-DJ library and the virus was allowed to replicate by providing Adenovirus 5.

In order to facilitate tracking of the selection process, a capsid region was chosen that was unique to each of the capsids but was flanked by homologous sequences, which allowed PCR amplification using a single pair of oligonucleotides. This 206 bp region served as a barcode and enabled tracking of the selection process using high-throughput next generation sequencing (NGS). This region was PCR amplified from each library mix before selection (initial mix) and after the first round of selection and their composition studied after Illumina NGS, using the differences in DNA sequences to identify reads originating from AAV2 and AAV-DJ.

As shown in FIG. 8B, after just one round of selection, the population shifted towards AAV-DJ in the functional transduction library (AAV2: 44.73 compared with AAV-DJ: 55.27) and remained stable and even shifted a little towards AAV2 (AAV2: 53.67 compared with AAV-DJ: 46.33) in the replication competent library.

This data supports the hypothesis that when the selective pressure is based on the ability to functionally transduce target cells, and as expected based on their transduction profiles, AAV-DJ is more readily selected than AAV2. In the context of the replication-competent selection platform, it is possible that AAV2 could replicate more efficiently than AAV-DJ in HuH-7 cells. The replication competent platform contains ITRs and Rep from AAV2, and thus the RC-AAV2 construct contains the same elements as wtAAV2 (ITR2-Rep2-Capt-ITR2), while the DJ capsid is a synthetic capsid and this not fully compatible with ITR2 and Rep2 elements. This could bias the replication competent selection towards AAV2.

Example 4. Functional Transduction Selection on CD34+ Cells

Selection of AAV using the functional transduction platform was then performed using human hematopoietic stem cells (CD34+) and T cells. An AAV shuffled library was generated that included the majority of the wild-type AAV serotypes (AAV1-12), with the cap genes being cloned into the functional transduction platform harbouring the Spleen Focus Forming Virus (SFFV) promoter (FT-SFFV-Lib-1/12).

The main aim of this study was to validate the functional transduction selection strategy on primary cells and to select for novel variants with improved transduction potential for CD34+ and T-cells when compared to AAV6. Replication-competent selection is not possible in this setting, as a suitable adenoviral helper that would infect T-cell and support AAV replication could not be identified. Because the functional transduction platform does not rely on the helper functions of an adenovirus, the platform provided the means to perform library selection process on human T-cells.

To perform selection on human CD34+ cells, human CD34+ cells isolated from mobilized peripheral blood were transduced with different volumes (effectively different MOIs) of the shuffled library, FT-SFFV-Lib-1/12, in order to determine the right amount of the library that would translate into low but sufficient percentage of GFP+ cells, allowing fluorescent activating cell sorting (FACS) and posterior DNA recovery. It was found that transduction of 2 million CD34+ cells resulting in 1×105 vector genomes per cell was an optimal starting point, since this was the lowest dose of the library that resulted in detectable GFP signal.

Following sorting of the GFP+ population by FACS, the total DNA was recovered as described above. The cap region was recovered by PCR amplification and cloned back into the FT-SFFV backbone in order to proceed with the second round of selection. In parallel, sequences of twenty individual clones were obtained their amino acid sequence analysed and compared to AAV6. Interestingly, 18 out of the 20 analysed clones harboured the region implicated in the attachment of AAV6 to cellular receptor, which is mediated by AAV6's Arg576, Lys493, Lys459 and Lys531 (Xie et al. *Virology.* 2011, 420(1):10-9). This suggests a vital role for these amino acids in the ability of selected clones to transduce CD34+ cells, and confirmed that, as expected, the library screening process was selecting for AAV6-like characteristics.

The second round of selection was then performed with AAV generated with the cap amplicons from the first round of selection. Surprisingly, when the cells were transduced at MOIs of $1\times10^5$ and $1\times10^4$ vector genomes/cell, significant cell death within 24 hours after transduction was observed. AAV toxicity has been reported when transducing other types of stem cells (Brown et al. *Hum Gene Ther.* 2017, 28(6):450-463). It is possible that the preselected library was already very efficient at transducing CD34+ cells and thus the MOIs used were too high, leading to toxicity. Based on this assumption, the library dose was reduced to $1\times10^3$ vgs/cell and in this case, even though the cell viability was still reduced to 55%, GFP+ sorting of the population could be performed and capsids recovered. Interestingly, this MOI was 100 times lower than the one required during the previous round to obtain a similar percentage of GFP+ cells, suggesting an enrichment of the library in vectors with higher fitness for CD34+ cells.

Following the second round of selection and recovery of capsid sequences by PCR, 40 random AAV clones were sequenced. Sequence analysis confirmed that all the sequenced clones but one (AAV-CD20) harboured the previously mentioned four amino acids associated with AAV6 cellular attachment. No further selection in the more variable 5' cap region was observed. A neutral role for that region was therefore postulated. On this assumption, the seven top-candidates, based on common features (what features), were vectorized. The AAV-CD20 variant was also vectorized. The selected cap variants were used to generate AAV packaging constructs, which in turn were used to package an scAAV cassette expressing eGFP under the control of CAG promoter (scAAV-CAG-eGFP). All vectors were titred and used to test their transduction efficiency on CD34+ cells using AAV6 as a reference/control (as described below in Example 7).

Example 5. Functional Transduction Selection on T Cells

Library selection on a mixed population of primary human pre-activated T-cells isolated from PBMCs was performed. The overall selection process was identical to the one described for CD34+ cells with the exception that during the FACS sorting step, T-cells were separated into CD4+ and CD8+ populations using anti-CD4 and anti-CD8 antibodies. This ability to identify specific cell types in the functional transduction selection process is an advantageous aspect of the method.

After two rounds of selection on T cells, 28 variants (14 from the CD4+ and 14 from the CD8+ population) were sequenced. Analysis of the sequences confirmed that, similar to what was observed for clones identified during selection on CD34+ cells, all clones harboured the four key amino acids implicated in AAV6 cellular attachment.

Example 6. Sequence Analysis of AAV Variants

In order to perform a more detailed analysis of the AAV variants selected on CD34+ and T-cells, ReX, a computational tool published in 2016 and which reveals the patterns of recombination of the shuffled clones (Huang et al. *Biotechniques.* 2016, 60(2):91-4) was employed. Briefly, the software aligns the input shuffled sequence with the parental serotypes and depicts the most-likely parental donor for each nucleotide. It was observed that the highest pressure for CD34+ and T cell transduction was on the middle to the 3' region of the capsid sequence, where only two parental serotypes contributed to the shuffling: AAV1 and AAV6. More variation was observed on the 5' region of the selected clones, suggesting less selective pressure at this zone.

AAV1 and AAV6 differ only in six amino acids, and thus are highly homologous at the DNA level. Accordingly, a high level of shuffling between those serotypes is expected. Interestingly, only one of those amino acid changes (AAV1-E531K AAV6) correlates with one of the four essential amino acids that provide AAV6 the capacity to bind heparin sulfate proteoglycan in addition to the common binding ability that AAV1 and AAV6 share for sialic acid (Huang et al. *J Virol.* 2016, 90(11):5219-5230). Even though the 3' end consists of AAV1/AAV6 shuffled regions, all of the isolated variants harboured AAV6's K531, suggesting a key role on this amino acid for CD34+ and T-cell transduction, since AAV6 (with only 6 amino acid differences) is significantly more efficient than AAV1 at transducing these cell types.

Two quantitative measures have been described when analysing shuffled variants. Levenshtein Distance and the Effective Mutation provide an insight into the similarity between the synthetic variant selected and parental serotypes used to generate the library. Levenshtein distance measures the number of differences (in this case nucleotides) between shuffled variants and parental serotypes. The shortest Levenshtein distance is known as the Effective Mutation, and it reflects the minimum point mutations required to revert a mutant to its closest parent. As seen in Table 2, AAV6 was the closest variant to the majority of the selected clones, indicating that the selection process favoured AAV6-like features: not surprising given the high efficiency of AAV6 to functionally transduce CD34+ and T cells.

TABLE 2

Measurement of Levenshtein Distance and Effective mutation

| | AAV1 | AAV2 | AAV3b | AAV4 | AAV5 | AAV6 | AAV7 | AAV8 | AAV9 | AAV10 | AAV11 | AAV12 |
|---|---|---|---|---|---|---|---|---|---|---|---|---|
| CD34_1 | 102 | 468 | 451 | 808 | 912 | 84 | 362 | 379 | 484 | 348 | 761 | 805 |
| CD34_20 | 305 | 255 | 430 | 842 | 925 | 318 | 390 | 392 | 492 | 389 | 802 | 843 |
| CD34_10 | 108 | 444 | 439 | 809 | 916 | 103 | 387 | 386 | 479 | 397 | 773 | 799 |
| CD34_15 | 90 | 478 | 472 | 825 | 929 | 78 | 399 | 418 | 500 | 403 | 792 | 831 |
| CD34_16 | 130 | 477 | 468 | 818 | 937 | 109 | 381 | 411 | 477 | 377 | 777 | 820 |
| CD34_18 | 103 | 450 | 462 | 807 | 934 | 84 | 407 | 414 | 515 | 399 | 778 | 810 |
| CD34_23 | 232 | 440 | 418 | 795 | 920 | 235 | 429 | 351 | 435 | 391 | 796 | 808 |
| CD34_12 | 110 | 463 | 455 | 821 | 922 | 90 | 395 | 367 | 496 | 368 | 790 | 825 |
| CD34_13 | 158 | 456 | 445 | 805 | 925 | 142 | 388 | 378 | 474 | 381 | 782 | 787 |
| TC01 | 120 | 449 | 416 | 808 | 931 | 104 | 386 | 403 | 489 | 381 | 779 | 821 |
| TC02 | 130 | 450 | 405 | 803 | 915 | 124 | 383 | 407 | 464 | 393 | 785 | 805 |
| TC03 | 155 | 435 | 422 | 820 | 930 | 140 | 433 | 451 | 496 | 439 | 817 | 819 |
| TC04 | 166 | 402 | 456 | 840 | 929 | 134 | 424 | 434 | 512 | 430 | 802 | 822 |
| TC09 | 129 | 450 | 464 | 818 | 918 | 107 | 359 | 412 | 485 | 388 | 798 | 828 |
| TC16 | 107 | 435 | 466 | 812 | 909 | 90 | 373 | 401 | 495 | 384 | 776 | 794 |
| TC24 | 47 | 474 | 456 | 825 | 920 | 69 | 358 | 389 | 492 | 378 | 773 | 813 |
| TC26 | 129 | 424 | 396 | 824 | 922 | 110 | 393 | 415 | 476 | 405 | 792 | 818 |
| TC33 | 49 | 470 | 462 | 824 | 921 | 48 | 384 | 399 | 491 | 391 | 779 | 822 |
| TC34 | 138 | 430 | 459 | 820 | 928 | 121 | 395 | 420 | 502 | 406 | 781 | 815 |
| TC36 | 112 | 469 | 453 | 801 | 935 | 103 | 375 | 392 | 484 | 374 | 777 | 813 |

Figure 9:
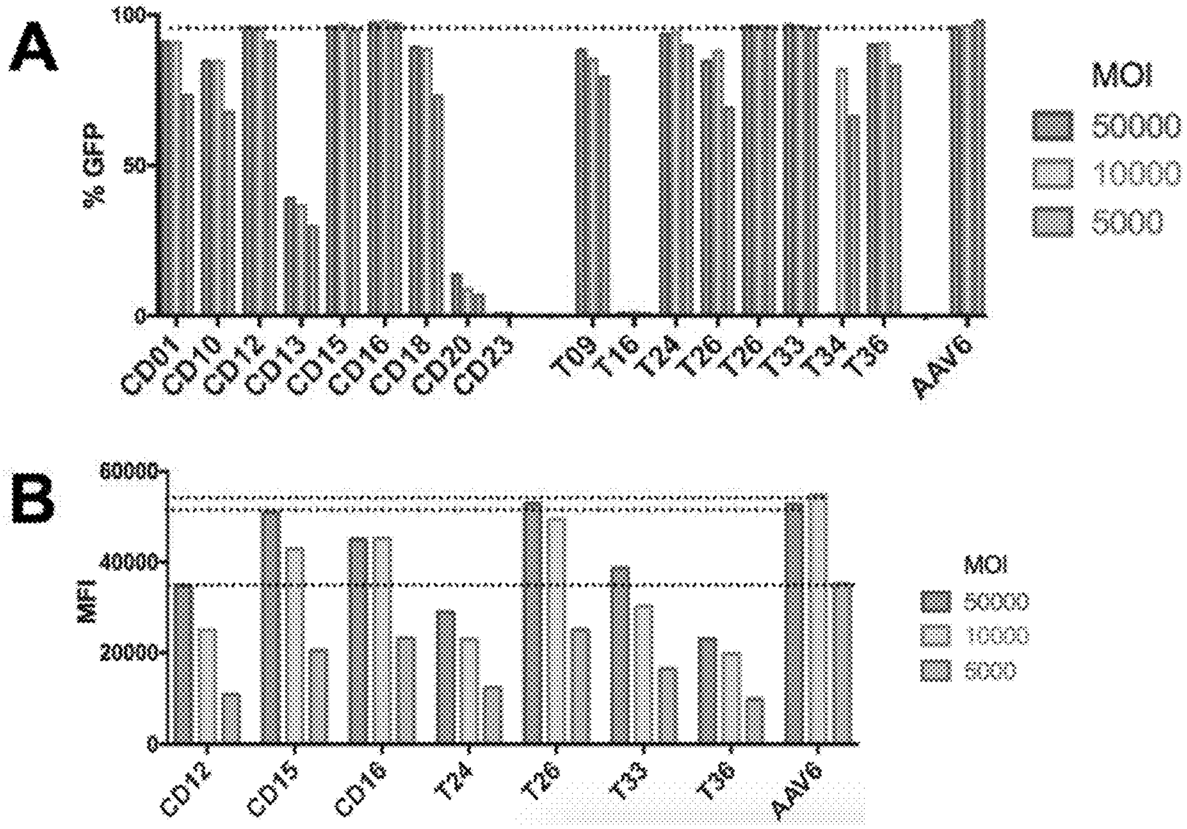
FIG. 9 presents the results of transduction of CD34+ cells with different AAV vectors at various MOIs. (A) The percentage of GFP positive cells following transduction. (B) The mean fluorescence intensity (MFI) of the GFP signal.

Example 7. Transduction Assessment of Selected Vectors in CD34+ Cells and T Cells Due to the similarity between vectors selected using CD34+ cells and T-cells, all vectors were subsequently tested on both cell types. To do so, the same transgene (scAAV-CAG-eGFP) was packaged into the isolated variants and AAV6 (as a positive control) and their transduction performance on CD34+ cells and T cells was assessed. Although the MOI's used in this instance were too high and led to signal saturation, making it difficult to accurately compare the tested vectors, it was nonetheless observed that some of the vectors appeared to achieve levels of transduction equivalent to AAV6 (FIG. 9A, showing the results of transduction of CD34+ cells). Comparing the mean fluorescent intensity (MFI) of the GFP signal for the vectors AAVCD12, AAVCD15, AAVCD16, AAVT24, AAVT26, AAVT33 and AAVT36 with AAV6, the newly identified vectors had lower MFIs than that observed for AAV6, suggesting that none of the isolated variants was more efficient at functionally transducing CD34+ than the parental AAV6, although some were comparable (FIG. 9B).

The newly isolated vectors were then tested on pre-activated T cells from four different donors at two different MOIs: $1\times10^5$ and $1\times10^4$ vgs/cell. Some of the vectors displayed similar but not superior transduction compared to AAV6 (data not shown).

One of the key features of any vector, besides the ability to transduce a determined cell type, is its packaging yield in terms of viral titre, a key characteristic that enables vector manufacturing and thus translational development. The packaging efficiency of the AAV vectors was assessed and compared with AAV6, which is known to give relatively low vector yields. To do so, independent crude productions of 5 dishes for each vector were prepared before the vectors were titered and the total vector genome yield assessed (final volume=1 mL). Most of the vectors, with the exception of AAVT08, showed yields similar to AAV6 (data now shown).

Example 8. Preparation and Assessment of FT3 Plasmids

The functional transduction (FT) plasmids and vectors utilized in Examples 2-7 have two promoters, where the cap gene is under the control of the p40 promoter and eGFP is under the control of the SFFV promoter. These vectors can be used for functional transduction selection in which the capsid is recovered from the vector genome, i.e. the DNA, as described in Examples 1-7. In an alternative, capsid could be recovered from cap mRNA rather than from the DNA in instances where the promoter driving expression of the cap gene is functional in the host cells used for selection and under the conditions used for selection.

Capsid recovery from cap mRNA rather than DNA may be desirable. When cap genes are directly amplified from the DNA of reporter protein-positive cells, there is a possibility that the recovered cap gene is from a virion that attached to the cell but did not enter, or from a virion that entered but did not lead to transgene expression in instances where a cell was transduced by several vectors. Selecting or amplifying all cap genes present in functionally transduced cells may therefore be biased because inefficient capsids can be selected through this bystander effect. However, while recovery of capsids from cap mRNA in transduced cells would address this issue, this is not possible when p40 is inactive in target cells.

To address this, a further alternative selection platform that facilitates selection on the basis of expression at the RNA level was developed. The FT3 platform, also referred to herein as the High Targeted Expression (HTE) platform, utilizes a single promoter that is active in the host cells used for selection and under the conditions used for selection to drive expression of both the cap and reporter genes in a single transcript. The genes are separated by an IRES so that translation is independent.

Plasmids for this FT3 platform (i.e. FT3 plasmids) were produced as described in Example 1 and as shown in FIG. 10, and assessed in various studies.

Vector Production

All combinations of FT3 plasmids and rep-containing helper plasmids shown in FIG. 10 were tested for their ability to yield high vector titers. FT3 vectors were produced by transfection of these plasmids in HEK293T cells and a plasmid coding the Adenovirus5 proteins VA, E4 and E2A. Three days after transfection, vectors were harvested and titrated.

Figure 5:
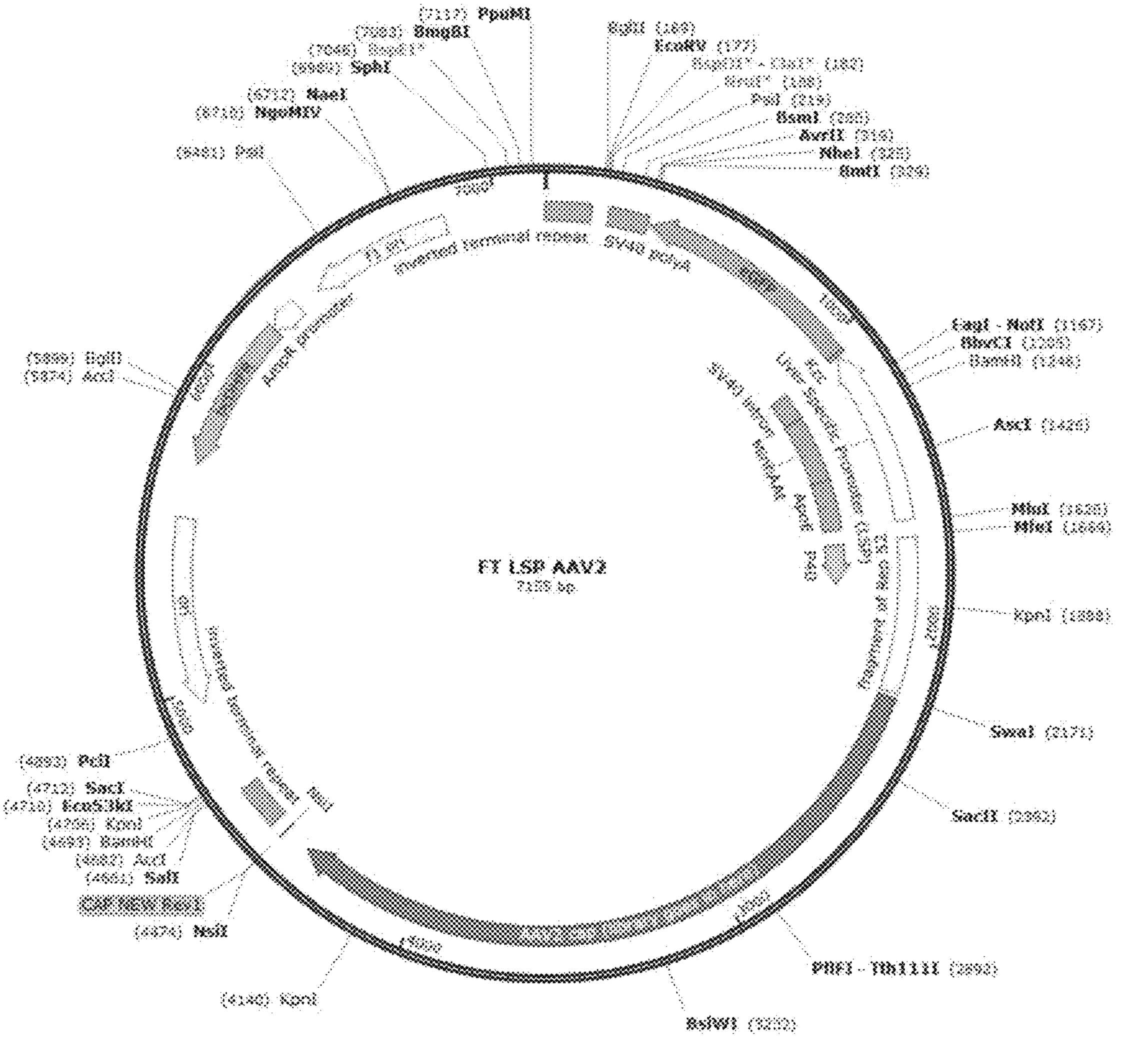
FIG. 5 is a map of the FT LSP AAV2 plasmid.

It was observed that the FT3 plasmids could be packaged with similar efficiency to the already tested and validated dual-promoter functional transduction plasmids (e.g. FT and FT2 plasmids, where FT plasmids are exemplified in Example 1 and FIG. 5; and FT2 plasmids are the same as FT plasmids but have one or more barcodes, or an insertion site for one or more barcodes, downstream of the GFP gene). The best helper plasmid for pES3 and pES5 appeared to be pRep2, whereas the best helper plasmid for pES9 appeared to be pES14 for pES9. These combinations were used in subsequent studies.

Helper-Free Transgene Expression

The main advantage of the FT3 platform is that cap is placed under a constitutive promoter (e.g. CMV or SFFV), whereas in the dual-promoter constructs utilized in Examples 2-7, it is under the p40 promoter, which is thought to be expressed only in the presence of Rep proteins. Vector transduction is performed in absence of helpers, thus without Rep proteins, it is expected that selection platforms such as FT2 that utilise dual promoters wouldn't allow cap expression in transduced cells, unlike FT3. FT3 should thus enable selection of capsids competent for functional transduction with limited bias, because the cap genes coding for these capsids should be expressed in transduced cells.

To test if FT3 plasmids can express their cap gene in the absence of helper plasmids, HEK293T cells were transfected with pES3-Ico6, pES5-Ico6 or pFT2-SFFV-Ico6, with and without helper plasmids (or with pRep2 and pAd5 for positive controls). Three days later, transfected cells were harvested and capsid-coding mRNA (later designated as Cap mRNA) were titrated by RT-qPCR.

Figure 11:
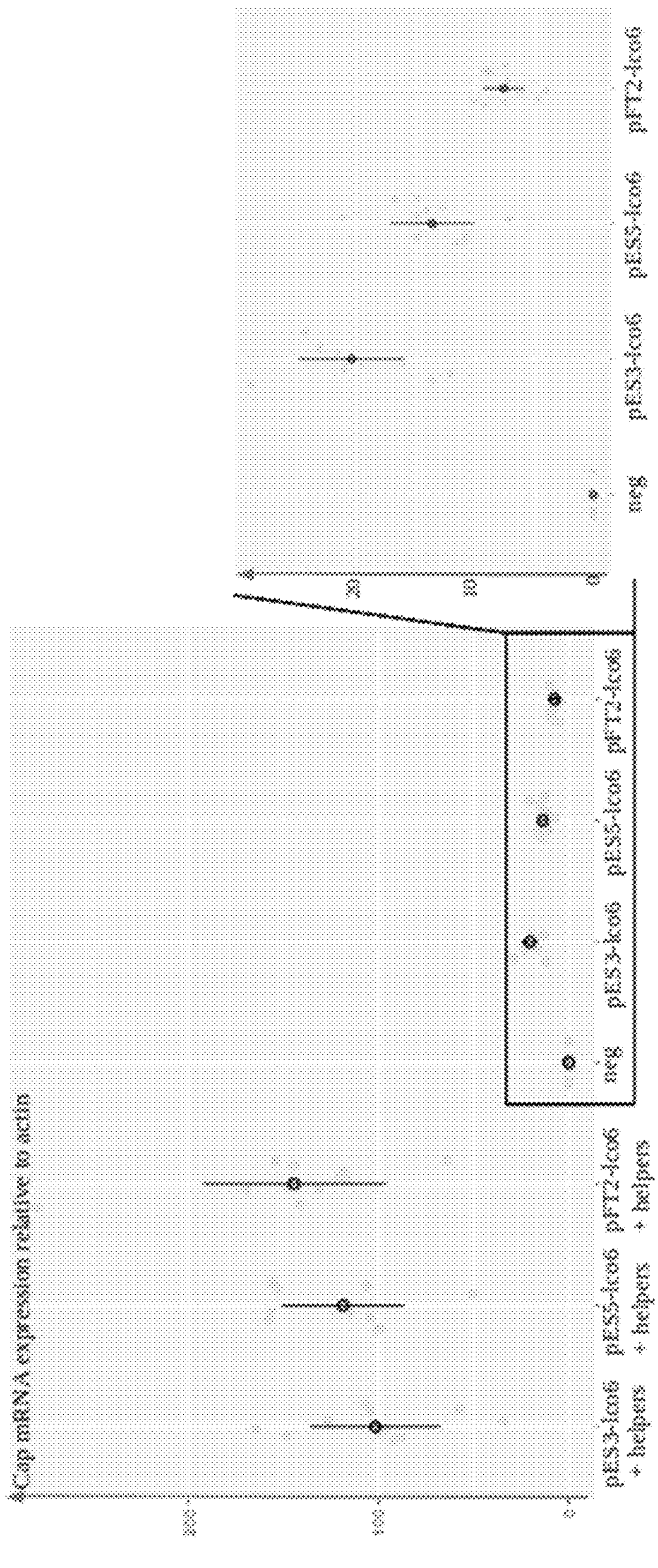
FIG. 11 shows cap expression after transfection of FT2 and FT3 plasmids, with or without helper plasmids. RNA was extracted from cells transfected 3 days earlier with plasmids, without or with (as positive controls) helper plasmids. RT-qPCR was performed, each one with 3 dilutions of cDNA for qPCR: 1/10, 1/100, 1/1000. A relative expression level of cap mRNA normalized on human β actin mRNA levels was computed for each dilution. Error bars: standard deviation. Neg: non-transfected cells.

As expected, the FT3 plasmids were able to induce higher cap mRNA expression in absence of helper plasmid than FT2 (FIG. 11). FT3 vectors are expected to have similar properties: therefore this experiment suggests that the FT3 platform may be useful for capsid selection for functional transduction using expressed cap mRNAs.

Unexpectedly, the dual promoter FT2 plasmid was able to express cap in absence of helper plasmids. Although the p40 promoter has been reported to require the Rep protein for expression (McCarthy et al. (1991) J. Virol, 65: 2936-2945), it is possible that the p40 promoter can activate in absence of Rep protein in cancer-derived cell lines. As demonstrated below, p40 activity driving either capsid genes or reporter genes or both has also been identified in HuH-7 cells (see FIG. 17, FT RNA), as well as HepG2 cells, HeLa cells and primary human retinal explants (data not shown).

Example 9. Functional Transduction with FT3 Vectors

Vectors derived from pFT2, pES3, pES5 and pES9 (see FIG. 10) with AAV2 cap were produced and purified by iodixanol gradient ultracentrifugation and used to transduce HuH7 cells of two different lineages. Three days after transduction, cap mRNA was detected and quantified.

It was observed that FT3 vectors were able to functionally transduce cells, as indicated by expression of their cap gene. Cap mRNA expression from FT3 CMV was 4 to 10 times higher than from FT3 SFFV at equal MOI for transductions in cells from the first HuH7 lineage, although this was not replicated in cells from the second HuH7 lineage (data not shown). Interestingly, and line with the results observed using the FT2 plasmids, relatively high p40-driven cap mRNA expression was observed in cells transduced by FT2 vectors, despite the lack of Rep protein (data now shown).

Example 10. Comparison of Different Selection Platforms

Figure 12:
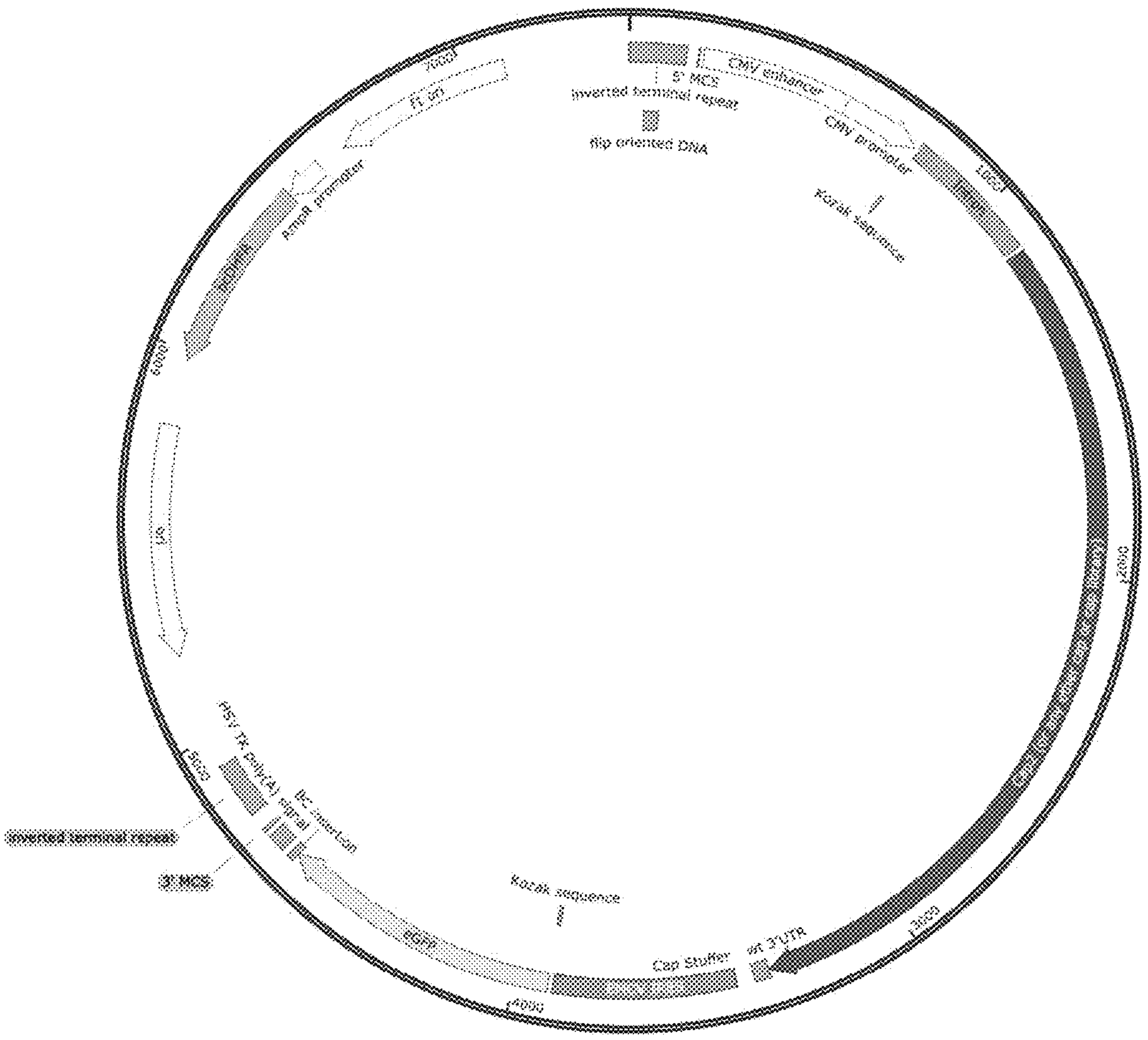
FIG. 12 provide maps of the HTE plasmids used in the studies (A) vHTE. (B) eHTE.
Figure 12:
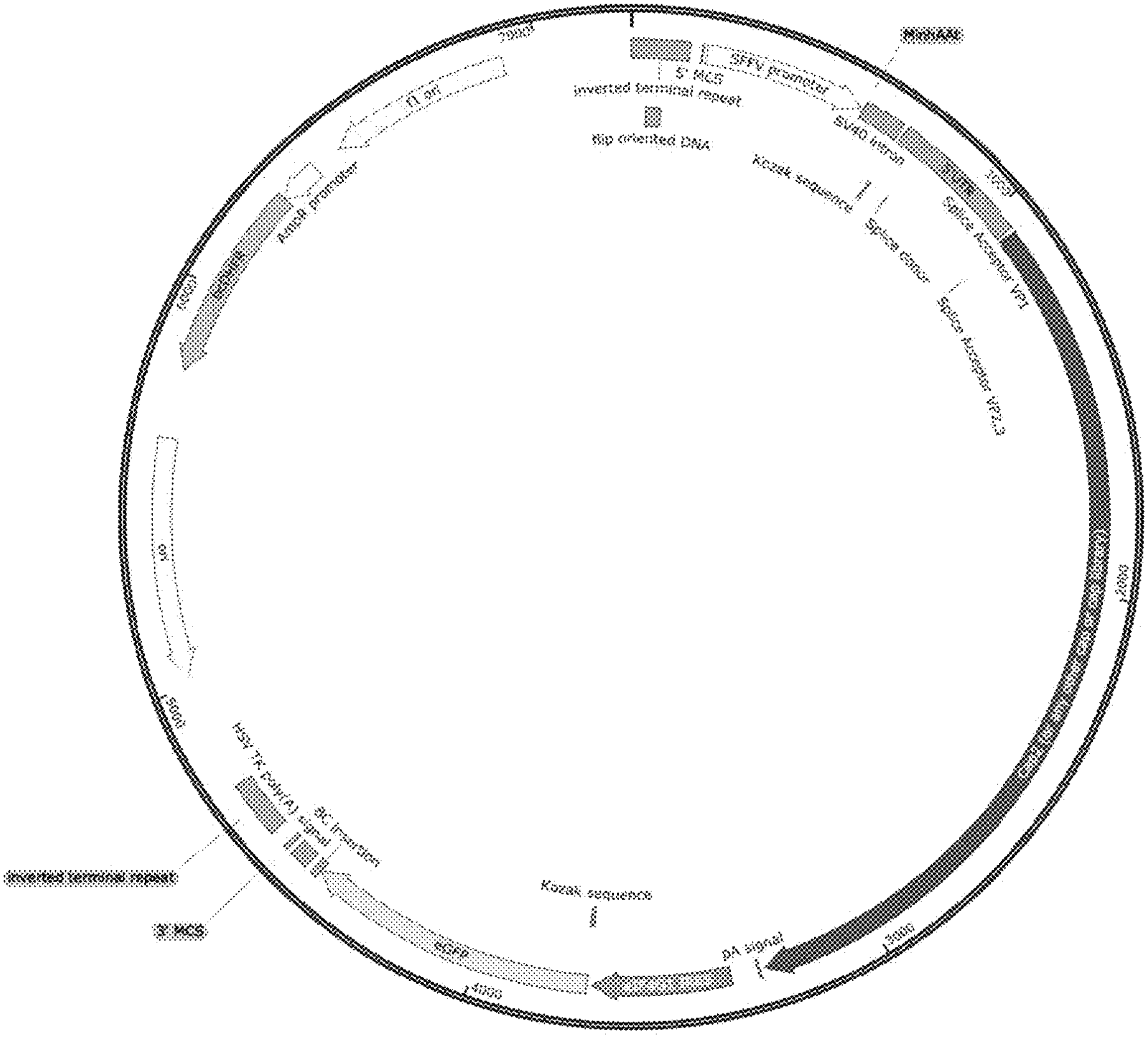
Figure 13:
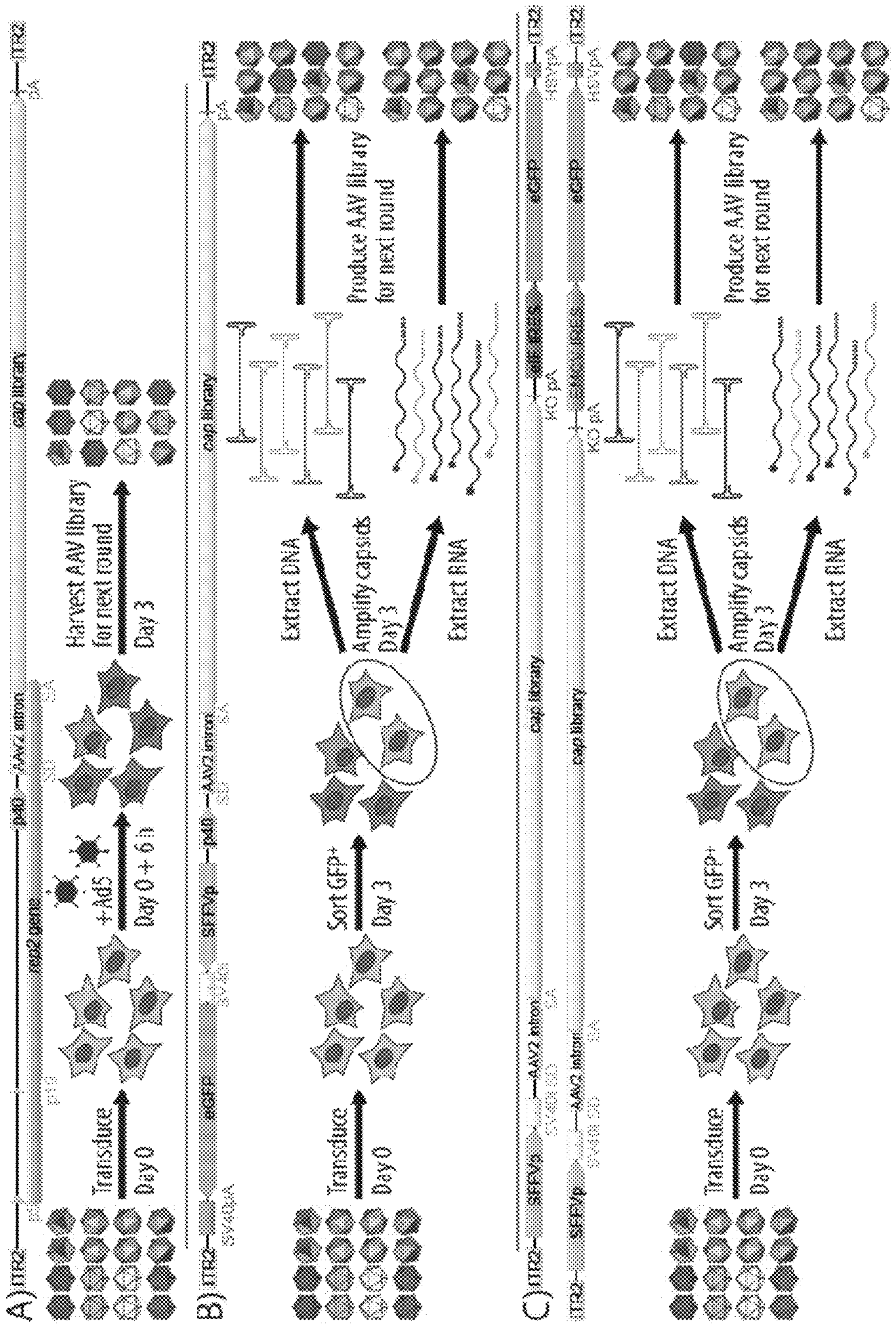
FIG. 13 is a schematic of the genetic architecture and selection methods for the various platforms. (A) Replication competent (RC) selection platform. (B) Functional Transduction (FT) selection platform. (C) High Targeted Expression (HTE; top: eHTE; bottom: vHTE) selection platform.

A series of studies were performed to compare the standard replication competent (RC) platform with two platforms based on functional transduction: FT (i.e. dual promoter platform) and FT3 (or HTE; i.e. single promoter platform). FIGS. 12 and 13 are schematics of the HTE plasmids and three different platforms used in these studies. For the HTE platform, two variations were included, one utilising the EMC virus-derived IRES (vHTE, sometimes referred to as FT3(-SFFV) and/or pES5, above) and one utilising an IRES from eukaryotic initiation factor 4G1 (eHTE).

Vector Production

Figure 14:
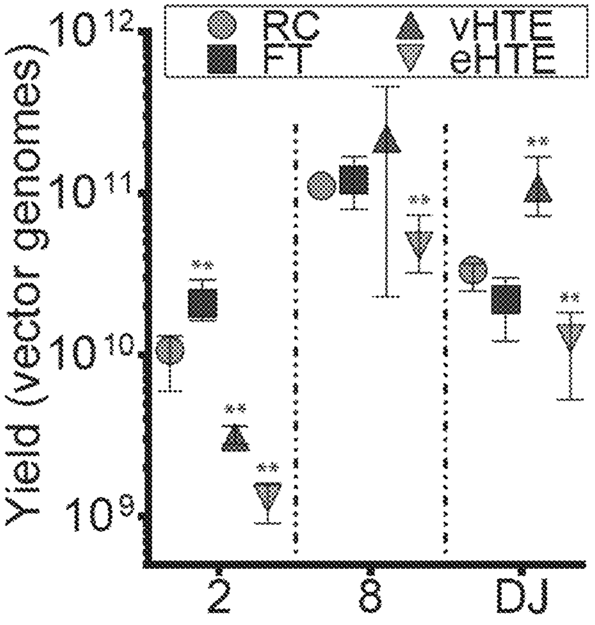
FIG. 14 shows the AAV yield when capsids from AAV2, 8 & DJ in the RC, FT and HTE (vHTE and eHTE) platforms. Vectors were produced by transfection of the RC, FT or HTE plasmids and the pAd5 plasmid in HEK293T cells. Plasmids containing rep were also transfected with the FT and HTE plasmids (rep already being provided in the RC plasmids). Crude lysates were titered using qPCR three days after transfection. Mann-Whitney comparison was performed to determine if the differences between FT, vHTE and eHTE were significantly different from the current benchmark, RC;  (p: 0.01>>0.001).

RC, FT and HTE plasmids containing AAV2, AAV8 or AAV-DJ cap genes were tested for their ability to yield high vector titers. Vectors were produced by transfection of the RC, FT or HTE plasmids and the pAd5 plasmid in HEK293T cells. Six plates of cells were transfected and the crude lysates were titered using qPCR three days after transfection. As shown in FIG. 14, titres varied between capsids and platforms, but all platforms were able to produce usable amounts of vectors. Generally speaking, RC and FT platforms produced higher yields than HTE-coded capsids.

Western blots were performed to confirm that AAV-DJ VP1, 2, 3 and the AAV2 Rep protein ratios remain in a wild-type like state in all three platforms. While the expression strength seemed to vary between the constructs, the ratios of expression appeared to be very stable (data not shown).

Cross Packaging

Cross packaging studies were performed to determine whether the FT and HTE platforms were able to faithfully package the correct genome to the same extent as the well characterised RC platform. The selection platforms were produced by transfecting cells with a dilution series of a 1:1 mix of plasmids carrying Cap2/Cap2_Y576* (RC, FT, eHTE) or Cap6/Cap6_S588* (vHTE). Both constructs can theoretically be packaged, but only non-mutated Cap2 and Cap6 can produce vectors, meaning detection of the N576*/S588* sequence inside an intact capsid is the rate of cross-packaging.

Over the course of the dilution, yields from RC and FT platforms remained stably high, whereas yields from the eHTE platform started lower and dropped more noticeably (FIG. 15C). It was also found that the packaging of the correct genome was heavily dependent on the amount of plasmid used for transfection at the production stage. Using 25,000 library plasmids, it was found that ~30% of AAV capsids in the FT platform actually packaged a genome containing a stop codon. In RC, vHTE and eHTE platforms, the cross-packaging was observed to be 22, 26 and 14% at the same condition, respectively. This percentage dropped to only 1-4 when the amount of library plasmids was reduced 500-fold (FIG. 15D).

This study demonstrates that the degree of cross-packaging using the synthetic FT and HTE platforms is essentially the same as the 'wild-type' AAV2-like RC platform, indicating that these synthetic platforms mimic the natural virus 'skill' of reliably packaging its own genome and thereby allowing directed evolution when they are produced under the correct conditions.

Assessment of the Capacity of Platforms to Select for Functional Capsids

Figure 16:
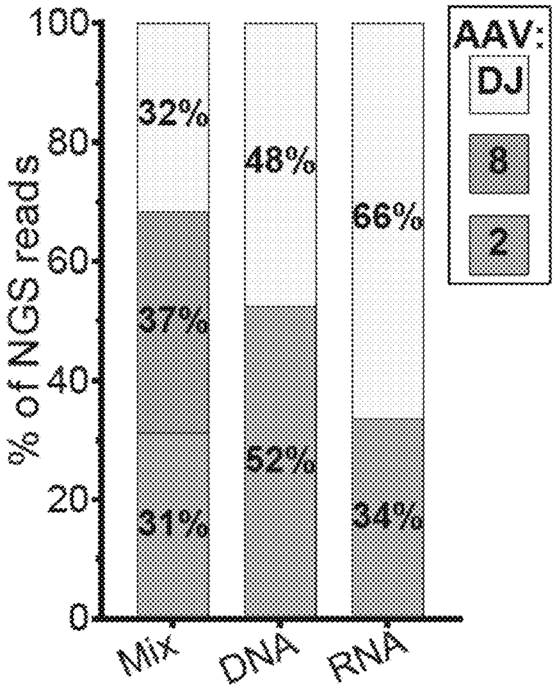
FIG. 16 shows the physical and functional transduction of selected AAV2, AAV8 and AAV-DJ vectors. Barcode NGS was used to determine which vector enters HuH-7 cells most efficiently (DNA) and which expresses its transgene most efficiently (RNA).

Huh7 cells were first transduced with AAV2, AAV8 and AAV DJ vectors, and barcode NGS was used to determine which vector entered HuH-7 cells best (DNA) and which expressed its transgene most efficiently (RNA). As shown in FIG. 16, AAV2 vectors entered cells most efficiently while AAV-DJ vectors were better at expressing their transgene.

A 'mini-library' selection using a mix of AAV2, 8 and DJ cap genes in all three selection platforms was then performed on HuH-7 cells. Selections were performed by Ad5-induced replication (for the RC platform), or by DNA and RNA extraction from transduced cells and subsequent analysis of capsid variants recovered from those (for the FT and HTE platforms). Capsid composition in the mini-library was determined by NGS using amplicon sequencing from capsids that were amplified using primers that bind in common regions between the three capsid genes, yet have several nucleotide differences between those primer binding regions, therefore serving as an internal barcode for this type of analysis.

As determined in the preliminary study using AAV2, AAV8 and AAV-DJ vectors, HuH-7 cells are best transduced by AAV DJ and worst transduced by AAV8. Therefore, selection for functional transduction was determined by 1) elimination of AAV8, and 2) enrichment of AAV-DJ.

Figure 17:
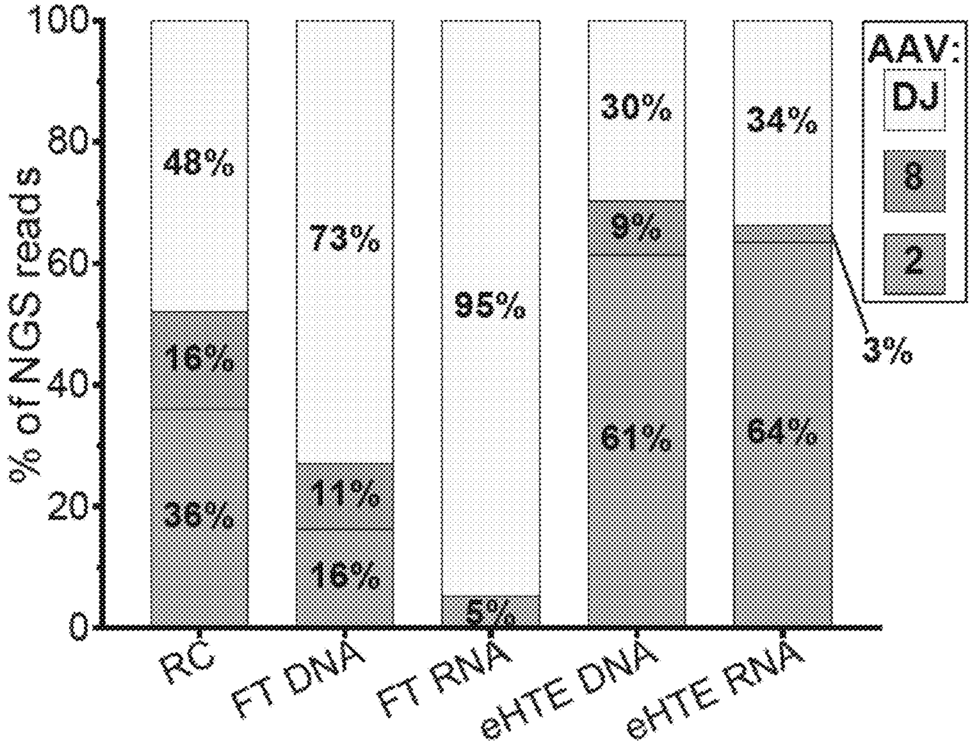
FIG. 17 shows the results of selection of a "mini library" using a mix of AAV2, AAV8 and AAV-DJ cap genes in all RC, FT and HTE selection platforms. Capsid composition in the mini-library was determined by NGS on a common region of all three capsids after one round of selection. The percentage of AAV2, AAV8 and AAV-DJ cap genes in the virions from the RC platform, and the DNA and RNA extracted from transduced cells in the FT and HTE platforms, was determined.

As shown in FIG. 17, the RC platform reduced the contribution of AAV8 sequences and enriched for AAV-DJ sequences, however, AAV2 is still relatively abundant, which can also be said for AAV8, keeping in mind how poorly it enters cells as a recombinant vector (FIG. 16). Recovering capsids from FT-DNA isolated from sorted GFP-positive HuH-7 cells, a great reduction of AAV8 sequences and an enrichment of AAV-DJ sequences was observed. Recovering capsids from RNA/cDNA, these ratios are even more evident with AAV8 fully diminished and AAV-DJ contributing 95% of all variants after one round of selection. Finally, HTE strongly selected against AAV8, however, AAV2 sequences packaged with the HTE platform also appeared to have entered the cells efficiently and contributed to 61% of reads. Consequently, the contribution to RNA from those cells was also high, although AAV-DJ increased its contribution more noticeably (from 30% DNA to 34% RNA) than AAV2 (64% RNA) showing that selection using RNA still favours the better expressing AAV-DJ.

Thus, generally speaking, recovery from RNA proved to be more stringent than DNA and the FT platform was more powerful at selecting against AAV8 and for AAV-DJ capsids.

DISCUSSION

Figure 8:
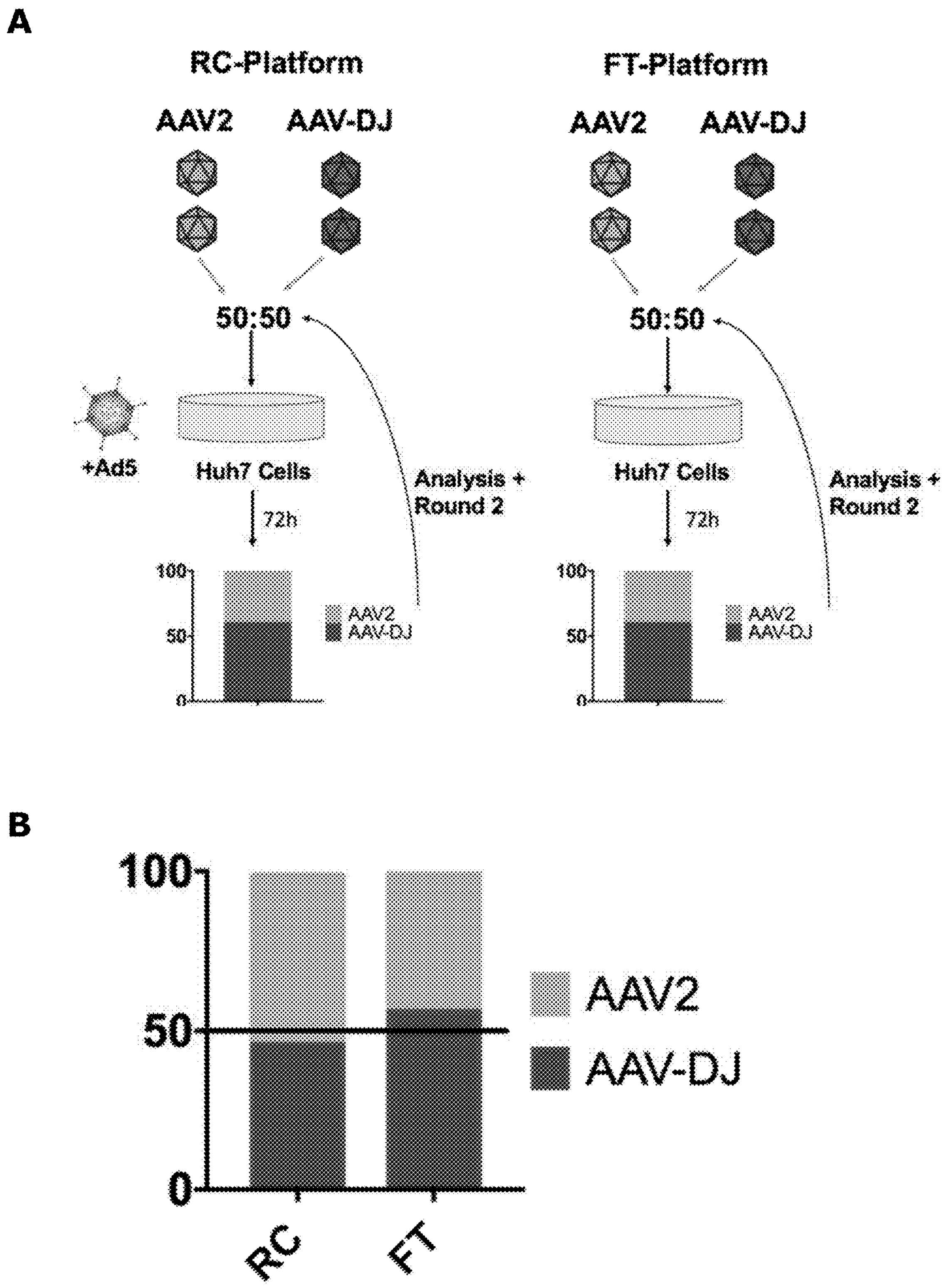
FIG. 8 represents a study that compares the efficiency of selection using a replication-competent platform and a functional transduction platform. (A) A schematic of the study protocol comparing selection using a replication-competent (RC) platform and a functional transduction (FT) platform, wherein each platform includes "mini" libraries containing only 2 capsid variants: cap2 or capDJ. Specifically, cap genes from wild-type AAV2 and AAV-DJ were cloned into traditional constructs based on replication-competent virions (RC-AAV2 and RC-DJ) and the functional transduction platform constructs (FT-AAV2 and FT-DJ). The four constructs were then packaged independently and the respective AAV2 and DJ were combined equimolarly based on qPCR titre data to form the RC and FT mini-libraries. Selection of each mini library was then performed on HuH7 cells so as to determine which platform allowed for faster selection of AAV-DJ. (B) The percentage of AAV2 or AAV-DJ in the population after one round of screening using the RC or FT platform.
Figure 15:
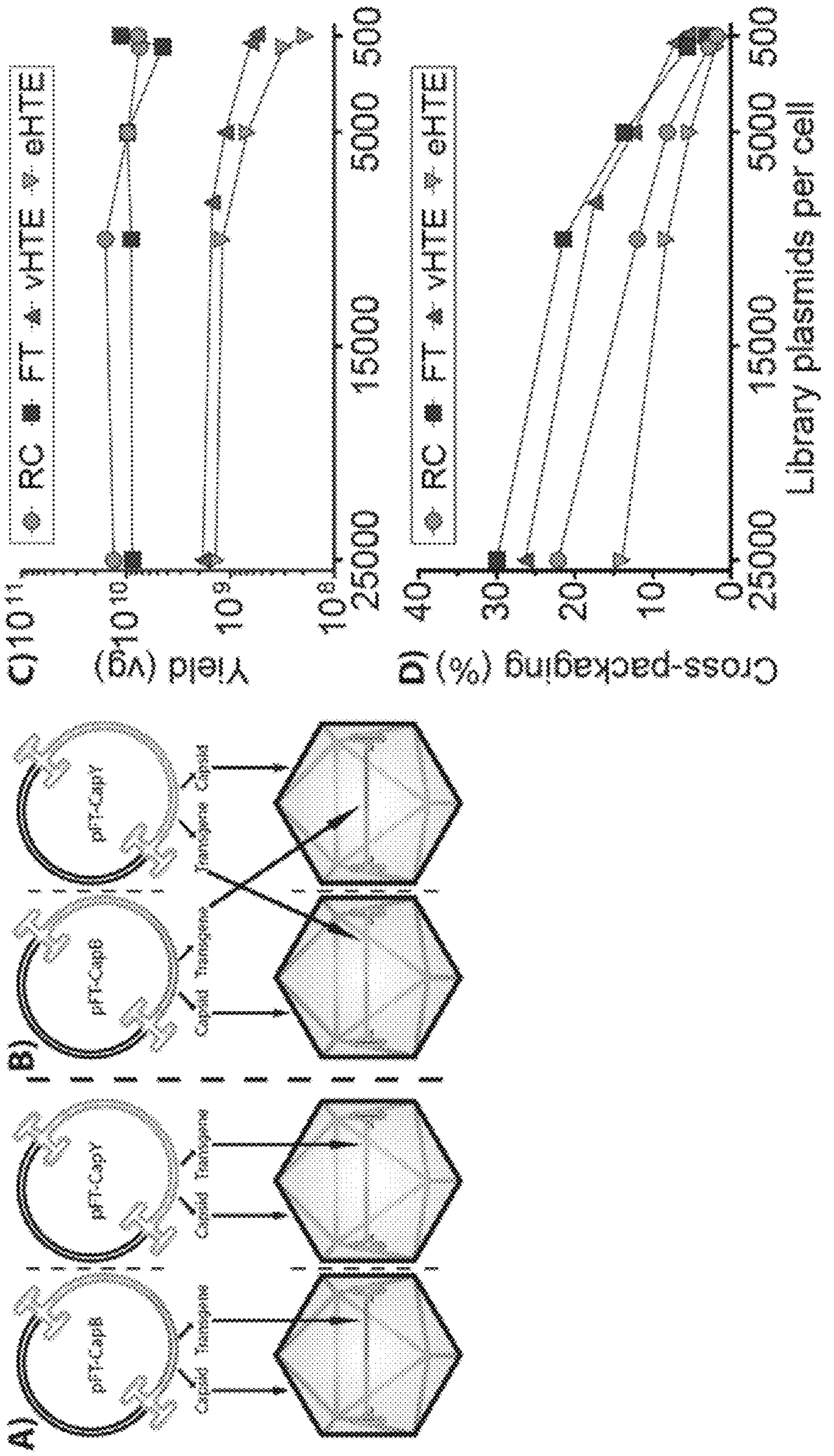
FIG. 15 is a schematic and graphical representation of a cross-packaging study using the RT, FT, vHTE and eHTE plasmids. (A) Schematic of high-fidelity packaging and (B) cross-packaging. (C) AAV production with a dilution series of a 1:1 mix of library with Cap2 and Cap2_Y576* (RC, FT, eHTE) or Cap6 and Cap6_S588* (vHTE). While both construct can theoretically be packaged, only Cap2 or Cap6 can produce vectors, meaning detection of the N576*/S588* sequence inside an intact capsid is the rate of cross-packaging. AAV yields are shown. (D) Levels of cross-packaging detected in the individual platforms using the above dilution series.

Novel selection platforms that allow for screening large AAV libraries based on the ability of individual variants to functionally transduce (i.e. express the transgene in) the target cells were developed. These offer an alternative to the commonly used replication-competent screening approach, where the overall pressure is put on viral—not vector—performance, since the variants have to carry out a complete lytic viral cycle as part of the selection process. This requirement of replication-competent platforms could bias the selection output towards viruses that are better at replicating their genomes, as suggested by the selection comparison of a minimal library consisting of AAV2 and AAV-DJ in the various platforms (FIGS. 8 and 15). This, of course, may lead to identification of suboptimal vector candidates, as replication ability is not relevant to AAV vectors used in gene therapy, which lack both the rep and cap genes and are unable to replicate. Thus, the functional transduction platforms provided here can be used to select capsid that are efficient at expressing their transgene in host cells. Furthermore, the novel platforms are also an improvement over previously reported approaches where investigators used the genetic architecture of a replication competent design (ITR-Rep-Cap-ITR) to produce a library that was then used to transduce cells without helper viruses. Those AAV will not replicate (depleting the replicative bias) but need to be recovered by PCR from the bulk of unlabelled and often not functionally transduced cells, leading to another bias which is the selection for non-expressing 'passenger' AAVs. Any of the herein described designs of the FT1,2,3 (HTE) platforms circumvents that issue.

Another important key benefit of the functional transduction approach is the ability to take advantage of FACS for identifying and sorting out cell subtypes within a heterogeneous population, as performed in Example 5 with the sorting of CD4+ and CD8+ T cell populations. This platform is particularly useful when performing selection in complex samples containing multiple cell types. During FACS, various cells can be stained using antibodies and cell populations of interest can be selected, or tissues can be sorted into various cell types and the library isolated from each type. Library selection can therefore be performed in multiple cell types separately and simultaneously (i.e. in parallel). This is important and differentiates the platform from regular replication competent library selection. In replication-competent systems, when working with multiple cells types containing the target cells in addition to other cells, there is no control as to the specific cells in which selection occurs: the library will potentially infect all cells, as will Ad5, and any virus that comes out will be harvested, regardless of whether it was from the target cells or other cells.

This ability to select cells in a complex population may be particularly useful when working with iPSC-derived cells (e.g. neurons, cardiomyocytes, etc.). These populations are contaminated with undifferentiated cells, which are easier to infect with Ad5 (and presumably the library too) so the selection could occur more efficiently in the undifferentiated cells, which are not the target cells. Using the functional transduction platform, antibodies specific for the differentiated cells can be used to select that population for analysis of transgene expression, and AAV nucleic acid from only those cells can be isolated for further selection rounds. Somewhat similarly, the ability to sort the target cells may be important when working with CD34+ cells, where it is of importance to gene edit the primitive CD34+/CD133+/CD90+ population, since it is that subpopulation of CD34+ that has been shown to engraft and repopulate the patient following autologous transplant (Diez et al. *EMBO Mol Med.* 2017, 9(11):1574-1588).

The invention claimed is:

1. A method for identifying an AAV cap gene suitable for vectorization, comprising:

a) transducing host cells with a library of replication-incompetent AAV, wherein the replication-incompetent AAV comprise a genome comprising two AAV ITRs flanking a reporter gene and a cap gene;

b) selecting one or more host cells in which expression of the reporter gene is detected;

c) isolating RNA and optionally DNA from the one or more host cells from b);

d) detecting reporter gene mRNA; and e) recovering one or more cap genes from the RNA or the DNA, or from cDNA produced from the RNA, thereby identifying one or more AAV cap genes suitable for vectorization.

2. The method of claim 1, wherein the reporter gene and the cap gene are operably linked to a single promoter, and wherein the reporter gene and the cap gene are separated by an internal ribosome binding site (IRES).

3. The method of claim 1, wherein the reporter gene is operably linked to a first promoter and the cap gene is operably linked to a second promoter.

4. The method of claim 2, wherein the single promoter is a ubiquitous and/or constitutive promoter.

5. The method of claim 3, wherein the first promoter is a ubiquitous and/or constitutive promoter.

6. The method of claim 3, wherein the second promoter is an AAV promoter.

7. The method of claim 1, wherein the cap gene comprises a 3' UTR and/or a 5' UTR.

8. The method of claim 7, wherein the reporter gene comprises a barcode.

9. The method of claim 8, wherein the barcode is at the 3' end of the reporter gene.

10. The method of claim 8, wherein d) further comprises converting the RNA to cDNA; amplifying and sequencing the barcode in the cDNA to identify one or more enriched barcodes; and identifying DNA that contains one of the enriched barcodes; and e) comprises recovering the one or more cap genes from the DNA identified as containing one of enriched barcodes.

11. The method of claim 3, wherein the reporter gene comprises a first barcode at the 3' end of the reporter gene, and the genome further comprises, between the two ITRs, a bacterial origin of replication, an antibiotic resistance gene, and a second barcode, wherein the first and second barcodes are at opposite ends of the genome and flank the reporter gene, the cap gene, the origin of replication and the antibiotic resistance gene.

12. The method of claim 11, wherein the cap gene comprises a 3' UTR.

13. The method of claim 11, wherein d) further comprises:

1) converting the RNA to cDNA;

2) amplifying and sequencing the first barcode in the cDNA to identify one or more enriched first barcodes;

amplifying one or more genomes from the DNA using primers specific for the first and second barcodes then circularizing the one or more resulting amplicons to produce one or more plasmids, wherein the first and second barcodes are adjacent each other in the one or more plasmids, and transforming the one or more plasmids into bacteria; and amplifying and sequencing the first and second barcodes from the one or more plasmids; and 3) identifying DNA that contains an enriched first barcode identified in 2); and e) comprises recovering the one or more cap genes from DNA identified as containing an enriched first barcode.

14. The method of claim 3, wherein the genome comprises an intron between the first promoter and the reporter gene and/or between the second promoter and the cap gene.

15. The method of claim 2, wherein the genome comprises an intron between the single promoter and the reporter gene or the single promoter and the cap gene.

16. The method of claim 1, wherein:

the genome comprises a poly adenylation sequence; and/or recovering the one or more cap genes comprises amplification of the one or more cap genes.

17. The method of claim 1, wherein when a plurality of cap genes are recovered in e), further comprising f) producing a plurality of replication-incompetent AAV as defined in a) with the plurality of cap genes.

18. The method of claim 17, further comprising repeating a)-f) one or more times.

19. The method of claim 1, wherein b) comprises selecting a subpopulation of host cells in which expression of a detectable marker is detected, such that the one or more host cells selected in b) are a subpopulation of the host cells in a).

20. The method of claim 1, further comprising producing one or more AAV vectors using the one or more cap genes identified for vectorization.

* * * * *

SEQUENCE LISTING

```
<160> NUMBER OF SEQ ID NOS: 38

<210> SEQ ID NO 1
<211> LENGTH: 7155
<212> TYPE: DNA
<213> ORGANISM: Artificial Sequence
<220> FEATURE:
<223> OTHER INFORMATION: FT LSP AAV2
<220> FEATURE:
<221> NAME/KEY: misc_feature
<222> LOCATION: (2184)..(2184)
<223> OTHER INFORMATION: n is a, c, g, or t
<220> FEATURE:
<221> NAME/KEY: misc_feature
<222> LOCATION: (2187)..(2188)
<223> OTHER INFORMATION: n is a, c, g, or t

<400> SEQUENCE: 1

ttggccactc cctctctgcg cgctcgctcg ctcactgagg ccgggcgacc aaaggtcgcc      60

cgacgcccgg gctttgcccg ggcggcctca gtgagcgagc gagcgcgcag agagggagtg     120

gccaactcca tcactagggg ttcctggagg ggtggagtcg tgacgtaaag atctgatatc     180

atcgatcgcg atgcaggcaa acttgtttat tgcagcttat aatggttaca aataaagcaa     240

tagcatcaca aatttcacaa ataaagcatt tttttcactg cattctagtt gtggtttgtc     300

caaactcatc aatgtatccc tagggctagc ctttacttgt acagctcgtc catgccgaga     360

gtgatcccgg cggcggtcac gaactccagc aggaccatgt gatcgcgctt ctcgttgggg     420

tctttgctca gggcggactg ggtgctcagg tagtggttgt cgggcagcag cacggggccg     480

tcgccgatgg gggtgttctg ctggtagtgg tcggcgagct gcacgctgcc gtcctcgatg     540
```

-continued

```
ttgtggcgga tcttgaagtt caccttgatg ccgttcttct gcttgtcggc catgatatag    600
acgttgtggc tgttgtagtt gtactccagc ttgtgcccca ggatgttgcc gtcctccttg    660
aagtcgatgc ccttcagctc gatgcggttc accagggtgt cgccctcgaa cttcacctcg    720
gcgcgggtct tgtagttgcc gtcgtccttg aagaagatgg tgcgctcctg gacgtagcct    780
tcgggcatgg cggacttgaa gaagtcgtgc tgcttcatgt ggtcggggta gcggctgaag    840
cactgcacgc cgtaggtcag ggtggtcacg agggtgggcc agggcacggg cagcttgccg    900
gtggtgcaga tgaacttcag ggtcagcttg ccgtaggtgg catcgccctc gccctcgccg    960
gacacgctga acttgtggcc gtttacgtcg ccgtccagct cgaccaggat gggcaccacc   1020
ccggtgaaca gctcctcgcc cttgctcacc atggtggcgg cgaattctct agatcagttc   1080
caaaggttgg aatctaaaag agagaaacaa ttagaatcag tagtttaaca cattatacac   1140
ttaaaaattt tatatttacc ttagagcggc cgccactgtc ccaggtcagt ggtggtgcct   1200
gaagctgagg agacagggcc ctgtcctcgt ccgtatttaa gcagtggatc cagaggggca   1260
acgggggagg ctgctggtga atattaacca aggtcacccc agttatcgga ggagcaaaca   1320
ggggctaagt ccactggctg ggatctgagt cgcccgccta cgctgcccgg acgctttgcc   1380
tgggcagtgt acagcttcca ctgcacttac cgaaaggagt cattggcgcg ccctctcaca   1440
ctacctaaac cacgccagga caacctctgc tcctctccac cgaaattcca aggggtcgag   1500
tggatgttgg aggtggcatg ggcccagaga ggtctctgac ctctgcccca gctccaaggt   1560
cagcaggcag ggagggctgt gtgtttgctg tttgctgctt gcaatgtttg cccattttag   1620
gctgcagacg cgtagtccct cgcatcgcct gcgctccctc cgcagtttca attgtaaggt   1680
caccaagcag gaagtcaaag actttttccg gtgggcaaag gatcacgtgg ttgaggtgga   1740
gcatgaattc tacgtcaaaa agggtggagc caagaaaaga cccgccccca gtgacgcaga   1800
tataagtgag cccaaacggg tgcgcgagtc agttgcgcag ccatcgacgt cagacgcgga   1860
agcttcgatc aactacgcag acaggtacca aaacaaatgt tctcgtcacg tgggcatgaa   1920
tctgatgctg tttccctgca gacaatgcga gagaatgaat cagaattcaa atatctgctt   1980
cactcacgga cagaaagact gtttagagtg ctttcccgtg tcagaatctc aacccgtttc   2040
tgtcgtcaaa aaggcgtatc agaaactgtg ctacattcat catatcatgg gaaaggtgcc   2100
agacgcttgc actgcctgcg atctggtcaa tgtggatttg gatgactgca tctttgaaca   2160
ataaatgatt taaatcaggt atgnctnncg atggttatct tccagattgg ctcgaggaca   2220
ctctctctga aggaataaga cagtggtgga agctcaaacc tggcccacca ccaccaaagc   2280
ccgcagagcg gcataaggac gacagcaggg gtcttgtgct tcctgggtac aagtacctcg   2340
gacccttcaa cggactcgac aagggagagc cggtcaacga ggcagacgcc gcggccctcg   2400
agcacgacaa agcctacgac cggcagctcg acagcggaga caacccgtac ctcaagtaca   2460
accacgccga cgcggagttt caggagcgcc ttaaagaaga tacgtctttt gggggcaacc   2520
tcggacgagc agtcttccag gcgaaaaaga gggttcttga acctctgggc ctggttgagg   2580
aacctgttaa gacggctccg ggaaaaaaga ggccggtaga gcactctcct gtggagccag   2640
actcctcctc gggaaccgga aaggcgggcc agcagcctgc aagaaaaaga ttgaattttg   2700
gtcagactgg agacgcagac tcagtacctg acccccagcc tctcggacag ccaccagcag   2760
ccccctctgg tctgggaact aatacgatgg ctacaggcag tggcgcacca atggcagaca   2820
ataacgaggg cgccgacgga gtgggtaatt cctcgggaaa ttggcattgc gattccacat   2880
```

-continued

```
ggatgggcga cagagtcatc accaccagca cccgaacctg ggccctgccc acctacaaca   2940
accacctcta caaacaaatt tccagccaat caggagcctc gaacgacaat cactactttg   3000
gctacagcac cccttggggg tattttgact tcaacagatt ccactgccac ttttcaccac   3060
gtgactggca aagactcatc aacaacaact ggggattccg acccaagaga ctcaacttca   3120
agctctttaa cattcaagtc aaagaggtca cgcagaatga cggtacgacg acgattgcca   3180
ataaccttac cagcacggtt caggtgttta ctgactcgga gtaccagctc ccgtacgtcc   3240
tcggctcggc gcatcaagga tgcctcccgc cgttcccagc agacgtcttc atggtgccac   3300
agtatggata cctcaccctg aacaacggga gtcaggcagt aggacgctct tcattttact   3360
gcctggagta ctttccttct cagatgctgc gtaccggaaa caactttacc ttcagctaca   3420
cttttgagga cgttcctttc cacagcagct acgctcacag ccagagtctg gaccgtctca   3480
tgaatcctct catcgaccag tacctgtatt acttgagcag aacaaacact ccaagtggaa   3540
ccaccacgca gtcaaggctt cagttttctc aggccggagc gagtgacatt cgggaccagt   3600
ctaggaactg gcttcctgga ccctgttacc gccagcagcg agtatcaaag acatctgcgg   3660
ataacaacaa cagtgaatac tcgtggactg gagctaccaa gtaccacctc aatggcagag   3720
actctctggt gaatccgggc ccggccatgg caagccacaa ggacgatgaa gaaaagtttt   3780
ttcctcagag cggggttctc atctttggga agcaaggctc agagaaaaca aatgtggaca   3840
ttgaaaaggt catgattaca gacgaagagg aaatcaggac aaccaatccc gtggctacgg   3900
agcagtatgg ttctgtatct accaacctcc agagaggcaa cagacaagca gctaccgcag   3960
atgtcaacac acaaggcgtt cttccaggca tggtctggca ggacagagat gtgtaccttc   4020
aggggcccat ctgggcaaag attccacaca cggacggaca ttttcacccc tctcccctca   4080
tgggtggatt cggacttaaa caccctcctc cacagattct catcaagaac accccggtac   4140
ctgcgaatcc ttcgaccacc ttcagtgcgg caaagtttgc ttccttcatc acacagtact   4200
ccacgggaca ggtcagcgtg gagatcgagt gggagctgca gaaggaaaac agcaaacgct   4260
ggaatcccga aattcagtac acttccaact acaacaagtc tgttaatgtg gactttactg   4320
tggacactaa tggcgtgtat tcagagcctc gccccattgg caccagatac ctgactcgta   4380
atctgtaatt gcctgttaat caataaaccg tttaattcgt ttcagttgaa ctttggtctc   4440
tgcgtatttc tttcttatct agtttccata tgcatagatg tagataagta gcatggcggg   4500
ttaatcatta actacaagga acccctagtg atggagttgg ccactccctc tctgcgcgct   4560
cgctcgctca ctgaggccgc ccgggcaaag cccgggcgtc gggcgacctt tggtcgcccg   4620
gcctcagtga gcgagcgagc gcgcagagag ggagtggcca aagcgcgcag ctgcctgcag   4680
gtcgactcta gaggatcccc gggtaccgag ctcgaattcg cattaatgaa tcggccaacg   4740
cgcggggaga ggcggtttgc gtattgggcg ctcttccgct tcctcgctca ctgactcgct   4800
gcgctcggtc gttcggctgc ggcgagcggt atcagctcac tcaaaggcgg taatacggtt   4860
atccacagaa tcaggggata acgcaggaaa gaacatgtga gcaaaaggcc agcaaaaggc   4920
caggaaccgt aaaaaggccg cgttgctggc gtttttccat aggctccgcc cccctgacga   4980
gcatcacaaa aatcgacgct caagtcagag gtggcgaaac ccgacaggac tataaagata   5040
ccaggcgttt ccccctggaa gctccctcgt gcgctctcct gttccgaccc tgccgcttac   5100
cggatacctg tccgcctttc tcccttcggg aagcgtggcg ctttctcata gctcacgctg   5160
taggtatctc agttcggtgt aggtcgttcg ctccaagctg ggctgtgtgc acgaaccccc   5220
cgttcagccc gaccgctgcg ccttatccgg taactatcgt cttgagtcca acccggtaag   5280
```

```
acacgactta tcgccactgg cagcagccac tggtaacagg attagcagag cgaggtatgt   5340

aggcggtgct acagagttct tgaagtggtg gcctaactac ggctacacta gaagaacagt   5400

atttggtatc tgcgctctgc tgaagccagt taccttcgga aaaagagttg gtagctcttg   5460

atccggcaaa caaaccaccg ctggtagcgg tggttttttt gtttgcaagc agcagattac   5520

gcgcagaaaa aaaggatctc aagaagatcc tttgatcttt tctacggggt ctgacgctca   5580

gtggaacgaa aactcacgtt aagggatttt ggtcatgaga ttatcaaaaa ggatcttcac   5640

ctagatcctt ttaaattaaa aatgaagttt taaatcaatc taaagtatat atgagtaaac   5700

ttggtctgac agattactgc tgtttttcgt acacgtgata gtaataggtg tacggattct   5760

tttcgtcggt cagacctttc tcaacgaaga cttctttcca gttggtcata tccatttctg   5820

gaaaaaaagt atcgccctca aaggcgtgat ggattttagt gatgtagagt ttgtctacat   5880

acggcagaaa caggtcgtag atctgtgcac caccgaaaat aaagatttct tcctcatttt   5940

tgcacagttc aaacacttct tcaacactgt gcgcgacttc gcaaccttcc acgtggtagc   6000

cttcgttacg ggtcacaata atgttacggc gaccaggcag cgggcgacca atagcctcgt   6060

agtttttacg gcccatgatc agcggatggc ccatggtggt ctttttaaca tactgcagct   6120

cactcggcag acgccaaggt aagttgttat ctttaccgat aacacggttc tcgtccatcg   6180

caaccataaa cgaaacgatc atactcttcc tttttcaata ttattgaagc atttatcagg   6240

gttattgtct catgagcgga tacatatttg aatgtattta gaaaaataaa caaatagggg   6300

ttccgcgcac atttccccga aaagtgccac ctgatgcggt gtgaaatacc gcacagatgc   6360

gtaaggagaa aataccgcat caggaaattg taagcgttaa tattttgtta aaattcgcgt   6420

taaatttttg ttaaatcagc tcatttttta accaataggc cgaaatcggc aaaatccctt   6480

ataaatcaaa agaatagacc gagatagggt tgagtgttgt tccagtttgg aacaagagtc   6540

cactattaaa gaacgtggac tccaacgtca aagggcgaaa aaccgtctat cagggcgatg   6600

gcccactacg tgaaccatca ccctaatcaa gttttttggg gtcgaggtgc cgtaaagcac   6660

taaatcggaa ccctaaaggg agcccccgat ttagagcttg acggggaaag ccggcgaacg   6720

tggcgagaaa ggaagggaag aaagcgaaag gagcgggcgc tagggcgctg gcaagtgtag   6780

cggtcacgct gcgcgtaacc accacacccg ccgcgcttaa tgcgccgcta cagggcgcgt   6840

ccattcgcca ttcaggctgc gcaactgttg ggaagggcga tcggtgcggg cctcttcgct   6900

attacgccag ctggcgaaag ggggatgtgc tgcaaggcga ttaagttggg taacgccagg   6960

gttttcccag tcacgacgaa gcttgcatgc ctgcaggcag ctgcgcgctc gaacttcatg   7020

cctgccgacc ttccccaggt cacgatccgg acggcgggtg agttcacatt ttarcagccg   7080

gacgtgcara ctccgctggt ggtctaacgt cggttaggtc ccttgaatca cgggacatat   7140

gttggtgttg gaggt                                                    7155
```

<210> SEQ ID NO 2
<211> LENGTH: 145
<212> TYPE: DNA
<213> ORGANISM: Adeno-associated virus

<400> SEQUENCE: 2

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcct                                          145
```

<210> SEQ ID NO 3
<211> LENGTH: 145
<212> TYPE: DNA
<213> ORGANISM: Adeno-associated virus

<400> SEQUENCE: 3
aggaacccct agtgatggag ttggccactc cctctctgcg cgctcgctcg ctcactgagg 60
ccgcccgggc aaagcccggg cgtcgggcga cctttggtcg cccggcctca gtgagcgagc 120
gagcgcgcag agagggagtg gccaa 145

<210> SEQ ID NO 4
<211> LENGTH: 720
<212> TYPE: DNA
<213> ORGANISM: Artificial Sequence
<220> FEATURE:
<223> OTHER INFORMATION: eGFP

<400> SEQUENCE: 4
ttacttgtac agctcgtcca tgccgagagt gatcccggcg gcggtcacga actccagcag 60
gaccatgtga tcgcgcttct cgttggggtc tttgctcagg gcggactggg tgctcaggta 120
gtggttgtcg ggcagcagca cggggccgtc gccgatgggg gtgttctgct ggtagtggtc 180
ggcgagctgc acgctgccgt cctcgatgtt gtggcggatc ttgaagttca ccttgatgcc 240
gttcttctgc ttgtcggcca tgatatagac gttgtggctg ttgtagttgt actccagctt 300
gtgccccagg atgttgccgt cctccttgaa gtcgatgccc ttcagctcga tgcggttcac 360
cagggtgtcg ccctcgaact tcacctcggc gcgggtcttg tagttgccgt cgtccttgaa 420
gaagatggtg cgctcctgga cgtagccttc gggcatggcg gacttgaaga agtcgtgctg 480
cttcatgtgg tcggggtagc ggctgaagca ctgcacgccg taggtcaggg tggtcacgag 540
ggtgggccag ggcacgggca gcttgccggt ggtgcagatg aacttcaggg tcagcttgcc 600
gtaggtggca tcgccctcgc cctcgccgga cacgctgaac ttgtggccgt ttacgtcgcc 660
gtccagctcg accaggatgg gcaccacccc ggtgaacagc tcctcgccct tgctcaccat 720

<210> SEQ ID NO 5
<211> LENGTH: 125
<212> TYPE: DNA
<213> ORGANISM: Simian virus 40

<400> SEQUENCE: 5
aacttgttta ttgcagctta taatggttac aaataaagca atagcatcac aaatttcaca 60
aataaagcat ttttttcact gcattctagt tgtggtttgt ccaaactcat caatgtatcc 120
ctagg 125

<210> SEQ ID NO 6
<211> LENGTH: 560
<212> TYPE: DNA
<213> ORGANISM: Artificial Sequence
<220> FEATURE:
<223> OTHER INFORMATION: LSP promoter

<400> SEQUENCE: 6
gaattctcta gatcagttcc aaaggttgga atctaaaaga gagaaacaat tagaatcagt 60
agtttaacac attatacact taaaaatttt atatttacct tagagcggcc gccactgtcc 120
caggtcagtg gtggtgcctg aagctgagga gacagggccc tgtcctcgtc cgtatttaag 180
cagtggatcc agaggggcaa cgggggaggc tgctggtgaa tattaaccaa ggtcacccca 240
gttatcggag gagcaaacag gggctaagtc cactggctgg gatctgagtc gcccgcctac 300
gctgcccgga cgctttgcct gggcagtgta cagcttccac tgcacttacc gaaaggagtc 360
attggcgcgc cctctcacac tacctaaacc acgccaggac aacctctgct cctctccacc 420
gaaattccaa ggggtcgagt ggatgttgga ggtggcatgg gcccagagag gtctctgacc 480
tctgccccag ctccaaggtc agcaggcagg gagggctgtg tgtttgctgt ttgctgcttg 540
caatgtttgc ccattttagg 560

<210> SEQ ID NO 7
<211> LENGTH: 212
<212> TYPE: DNA
<213> ORGANISM: Homo sapiens

<400> SEQUENCE: 7
gggcagagcg cacatcgccc acagtccccg agaagttggg gggaggggtc ggcaattgaa 60
ccggtgccta gagaaggtgg cgcggggtaa actgggaaag tgatgtcgtg tactggctcc 120
gcctttttcc cgagggtggg ggagaaccgt atataagtgc agtagtcgcc gtgaacgttc 180
tttttcgcaa cgggtttgcc gccagaacac ag 212

<210> SEQ ID NO 8
<211> LENGTH: 402
<212> TYPE: DNA
<213> ORGANISM: Spleen focus-forming virus

<400> SEQUENCE: 8
cgactcagtc tgtcggagga ctggcgcgcc gagtgagggg ttgtgagctc ttttatagag 60
ctcgggaagc agaagcgcgc gaacagaagc gagaagcagg ctgattggtt aattcaaata 120
aggcgcaggg tcatttcagg tccttggggg agcctggaaa catctgatgg gtcttaagaa 180
actgctgagg gttgggccat atctggggac catctgttct tggcctcggg ccggggccga 240
aactgcggtg accatctgtt cttggccccg ggccggggcc gaaactgctc accgcagata 300
tcctgtttgg cccaacgtta gctattttca tgtacccgcc cttgatctga acttctctat 360
tcttggtttg gtatttttcc atgccttgca aaatggcgtt ac 402

<210> SEQ ID NO 9
<211> LENGTH: 489
<212> TYPE: DNA
<213> ORGANISM: Adeno-associated virus

<400> SEQUENCE: 9
aaggtcacca agcaggaagt caaagacttt ttccggtggg caaaggatca cgtggttgag 60
gtggagcatg aattctacgt caaaaagggt ggagccaaga aaagacccgc ccccagtgac 120
gcagatataa gtgagcccaa acgggtgcgc gagtcagttg cgcagccatc gacgtcagac 180
gcggaagctt cgatcaacta cgcagacagg taccaaaaca aatgttctcg tcacgtgggc 240
atgaatctga tgctgtttcc ctgcagacaa tgcgagagaa tgaatcagaa ttcaaatatc 300
tgcttcactc acggacagaa agactgttta gagtgctttc ccgtgtcaga atctcaaccc 360
gtttctgtcg tcaaaaaggc gtatcagaaa ctgtgctaca ttcatcatat catgggaaag 420
gtgccagacg cttgcactgc ctgcgatctg gtcaatgtgg atttggatga ctgcatcttt 480
gaacaataa 489

<210> SEQ ID NO 10

<211> LENGTH: 104
<212> TYPE: DNA
<213> ORGANISM: Simian virus 40

<400> SEQUENCE: 10
gaattctcta gatcagttcc aaaggttgga atctaaaaga gagaaacaat tagaatcagt 60
agtttaacac attatacact taaaaatttt atatttacct taga 104

<210> SEQ ID NO 11
<211> LENGTH: 1932
<212> TYPE: DNA
<213> ORGANISM: Adeno-associated virus

<400> SEQUENCE: 11
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggccct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtatttaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
cactctctct ga 1932

<210> SEQ ID NO 12
<211> LENGTH: 34
<212> TYPE: DNA
<213> ORGANISM: Adeno-associated virus

<400> SEQUENCE: 12
attttgaagc gggaggtttg aacgcgcagc cgcc 34

<210> SEQ ID NO 13
<211> LENGTH: 45
<212> TYPE: DNA
<213> ORGANISM: Artificial Sequence
<220> FEATURE:
<223> OTHER INFORMATION: Cap rescue F

<400> SEQUENCE: 13
ccctgcagac aatgcgagag aatgaatcag aattcaaata tctgc 45

<210> SEQ ID NO 14
<211> LENGTH: 33
<212> TYPE: DNA
<213> ORGANISM: Artificial Sequence
<220> FEATURE:
<223> OTHER INFORMATION: Cap rescue R

<400> SEQUENCE: 14
atgcatatgg aaactagata agaaagaaat acg 33

<210> SEQ ID NO 15
<211> LENGTH: 204
<212> TYPE: DNA
<213> ORGANISM: Cytomegalovirus

<400> SEQUENCE: 15
gtgatgcggt tttggcagta catcaatggg cgtggatagc ggtttgactc acggggattt 60
ccaagtctcc accccattga cgtcaatggg agtttgtttt ggcaccaaaa tcaacgggac 120
tttccaaaat gtcgtaacaa ctccgcccca ttgacgcaaa tgggcggtag gcgtgtacgg 180
tgggaggtct atataagcag agct 204

<210> SEQ ID NO 16
<211> LENGTH: 463
<212> TYPE: DNA
<213> ORGANISM: Encephalomyocarditis virus

<400> SEQUENCE: 16
gagggcccgg aaacctggcc ctgtcttctt gacgagcatt cctaggggtc tttcccctct 60
cgccaaagga atgcaaggtc tgttgaatgt cgtgaaggaa gcagttcctc tggaagcttc 120
ttgaagacaa acaacgtctg tagcgaccct ttgcaggcag cggaaccccc cacctggcga 180
caggtgcctc tgcggccaaa agccacgtgt ataagataca cctgcaaagg cggcacaacc 240
ccagtgccac gttgtgagtt ggatagttgt ggaaagagtc aaatggctct cctcaagcgt 300
attcaacaag gggctgaagg atgcccagaa ggtaccccat tgtatgggat ctgatctggg 360
gcctcggtgc acatgcttta catgtgttta gtcgaggtta aaaaaacgtc taggcccccc 420
gaaccacggg gacgtggttt tcctttgaaa aacacgatga taa 463

<210> SEQ ID NO 17
<211> LENGTH: 344
<212> TYPE: DNA
<213> ORGANISM: Homo sapiens

<400> SEQUENCE: 17
tagatggggg tcctgggccc cagggtgtgc agccactgac ttggggactg ctggtggggt 60
agggatgagg gagggagggg cattgtgatg tacagggctg ctctgtgaga tcaagggtct 120
cttaagggtg ggagctgggg cagggactac gagagcagcc agatgggctg aaagtggaac 180
tcaaggggtt tctggcacct acctacctgc ttcccgctgg ggggtgggga gttggcccag 240
agtcttaaga ttggggcagg gtggagaggt gggctcttcc tgcttcccac tcatcttata 300
gctttctttc cccagatccg aattcgagat ccaaaccaag gagg 344

<210> SEQ ID NO 18
<211> LENGTH: 711
<212> TYPE: DNA
<213> ORGANISM: Artificial Sequence
<220> FEATURE:
<223> OTHER INFORMATION: mCherry

<400> SEQUENCE: 18
atggtgagca agggcgagga ggataacatg gccatcatca aggagttcat gcgcttcaag 60
gtgcacatgg agggctccgt gaacggccac gagttcgaga tcgagggcga gggcgagggc 120
cgcccctacg agggcaccca gaccgccaag ctgaaggtga ccaagggtgg ccccctgccc 180
ttcgcctggg acatcctgtc ccctcagttc atgtacggct ccaaggccta cgtgaagcac 240
cccgccgaca tccccgacta cttgaagctg tccttccccg agggcttcaa gtgggagcgc 300
gtgatgaact tcgaggacgg cggcgtggtg accgtgaccc aggactcctc cctgcaggac 360
ggcgagttca tctacaaggt gaagctgcgc ggcaccaact tcccctccga cggccccgta 420
atgcagaaga agaccatggg ctgggaggcc tcctccgagc ggatgtaccc cgaggacggc 480
gccctgaagg gcgagatcaa gcagaggctg aagctgaagg acggcggcca ctacgacgct 540
gaggtcaaga ccacctacaa ggccaagaag cccgtgcagc tgcccggcgc ctacaacgtc 600
aacatcaagt tggacatcac ctcccacaac gaggactaca ccatcgtgga acagtacgaa 660
cgcgccgagg gccgccactc caccggcggc atggacgagc tgtacaagta g 711

<210> SEQ ID NO 19
<211> LENGTH: 20
<212> TYPE: DNA
<213> ORGANISM: Artificial Sequence
<220> FEATURE:
<223> OTHER INFORMATION: SC010 primer

<400> SEQUENCE: 19
ttctcgttgg ggtctttgct 20

<210> SEQ ID NO 20
<211> LENGTH: 20
<212> TYPE: DNA
<213> ORGANISM: Artificial Sequence
<220> FEATURE:
<223> OTHER INFORMATION: SC011 primer

<400> SEQUENCE: 20
tcaagatccg ccacaacatc 20

<210> SEQ ID NO 21
<211> LENGTH: 18
<212> TYPE: DNA
<213> ORGANISM: Artificial Sequence
<220> FEATURE:
<223> OTHER INFORMATION: VG619 primer

<400> SEQUENCE: 21
gccactaacc ctgtggcc 18

<210> SEQ ID NO 22
<211> LENGTH: 20
<212> TYPE: DNA
<213> ORGANISM: Artificial Sequence
<220> FEATURE:
<223> OTHER INFORMATION: VG620 primer

<400> SEQUENCE: 22
cgtctctgtc ttgccacacc 20

<210> SEQ ID NO 23
<211> LENGTH: 26
<212> TYPE: DNA
<213> ORGANISM: Artificial Sequence
<220> FEATURE:
<223> OTHER INFORMATION: VG660 primer

<400> SEQUENCE: 23
agagcagctg aacagaccct gcgacc 26

<210> SEQ ID NO 24
<211> LENGTH: 26
<212> TYPE: DNA
<213> ORGANISM: Artificial Sequence
<220> FEATURE:
<223> OTHER INFORMATION: VG661 primer

<400> SEQUENCE: 24
ggtctgttca gctgctctgg aggttg 26

<210> SEQ ID NO 25
<211> LENGTH: 22
<212> TYPE: DNA
<213> ORGANISM: Artificial Sequence
<220> FEATURE:
<223> OTHER INFORMATION: VG688 primer

<400> SEQUENCE: 25
ctgatgctgt ttccctgcag ac 22

<210> SEQ ID NO 26
<211> LENGTH: 35
<212> TYPE: DNA
<213> ORGANISM: Artificial Sequence
<220> FEATURE:
<223> OTHER INFORMATION: VG689 primer

<400> SEQUENCE: 26
ttaaacggtt tattgattaa caggcaatta caggg 35

<210> SEQ ID NO 27
<211> LENGTH: 34
<212> TYPE: DNA
<213> ORGANISM: Artificial Sequence
<220> FEATURE:
<223> OTHER INFORMATION: VG732 primer

<400> SEQUENCE: 27
cggtttattg attaacaggc aattacagat tacg 34

<210> SEQ ID NO 28
<211> LENGTH: 37
<212> TYPE: DNA
<213> ORGANISM: Artificial Sequence
<220> FEATURE:
<223> OTHER INFORMATION: VG690 primer

<400> SEQUENCE: 28
ctgtaattgc ctgttaatca ataaaccgtt taattcg 37

<210> SEQ ID NO 29
<211> LENGTH: 22
<212> TYPE: DNA
<213> ORGANISM: Artificial Sequence
<220> FEATURE:
<223> OTHER INFORMATION: VG691 primer

<400> SEQUENCE: 29
cgcattgtct gcagggaaac ag 22

<210> SEQ ID NO 30
<211> LENGTH: 15
<212> TYPE: DNA
<213> ORGANISM: Artificial Sequence
<220> FEATURE:
<223> OTHER INFORMATION: VG693 primer

<400> SEQUENCE: 30
cacacccgcc gccag 15

<210> SEQ ID NO 31
<211> LENGTH: 17
<212> TYPE: DNA
<213> ORGANISM: Artificial Sequence
<220> FEATURE:
<223> OTHER INFORMATION: VG694 primer

<400> SEQUENCE: 31
atgcccacca tcacgcc 17

<210> SEQ ID NO 32
<211> LENGTH: 25
<212> TYPE: DNA
<213> ORGANISM: Artificial Sequence
<220> FEATURE:
<223> OTHER INFORMATION: VG760 primer

<400> SEQUENCE: 32
agacgaagag gaaatcagga caacc 25

<210> SEQ ID NO 33
<211> LENGTH: 19
<212> TYPE: DNA
<213> ORGANISM: Artificial Sequence
<220> FEATURE:
<223> OTHER INFORMATION: VG761 primer

<400> SEQUENCE: 33
ccatgcctgg aagaacgcc 19

<210> SEQ ID NO 34
<211> LENGTH: 2211

<212> TYPE: DNA
<213> ORGANISM: Adeno-associated virus

<400> SEQUENCE: 34
atggctgccg atggttatct tccagattgg ctcgaggaca acctctctga aggcattcgc 60
gagtggtggg acttgaaacc tggagccccg aaacccaaag ccaaccagca aaagcaggac 120
gacggccggg gtcttgtgct tcctggttac aagtacctcg gacccttcaa cggactcgac 180
aagggggagc ccgtcaacgc ggcggacgca gcggccctcg agcacgacaa ggcctacgac 240
cagcagctca aggcgggtga caacccgtac ctccggtaca accacgccga cgccgagttt 300
caggagcgtc tgcaagaaga tacgtctttt gggggcaacc tcgggcgagc agtcttccag 360
gccaagaaga gggttctcga accttttggt ctggttgagg aaggcgctaa gacggctcct 420
ggaaagaagc gtccggtaga gcagtctcca caggagccag actcctcctc gggcatcggc 480
aagacaggcc agcagcccgc taaaaagaga ctcaattttg gtcagactgg cgactcagag 540
tcagtccccg accctcaacc tctcggagaa cctccagcaa cccccgctgc tgtgggacct 600
actacaatgg cttcaggcgg tggcgcacca atggcagaca ataacgaagg cgccgacgga 660
gtgggtaatg cctcgggaaa ttggcattgc gattccacat ggctgggcga cagagtcatc 720
accaccagca cccgaacctg ggccctgccc acctacaaca accacctcta caagcaaatc 780
tccagtgctt caacgggagc cagcaacgac aaccactact tcggctacag caccccctgg 840
gggtattttg acttcaacag attccactgc cacttctcac cacgtgactg gcagcgactc 900
atcaacaaca actggggatt ccggcccaag agactcaact tcaagctctt caacatccaa 960
gtcaaggagg tcacgacgaa tgatggcgtc acgaccatcg ccaataacct taccagcacg 1020
gttcaagtgt tttcggactc ggagtaccag ctcccgtacg tcctcggctc tgcgcaccag 1080
ggctgcctcc ctccgttccc ggcggacgtc ttcatgattc cgcagtacgg ctacctgacg 1140
ctgaacaacg gcagccaggc cgtgggacgc tcatcctttt actgcctgga atacttccct 1200
tcgcagatgc tgagaacggg caacaacttt accttcagct acacctttga ggacgtgcct 1260
ttccacagca gctacgctca cagccagagc ctggaccggc tgatgaatcc tctcatcgac 1320
cagtacctgt actacctgaa cagaactcaa aatcagtccg gaagtgccca aaacaaggac 1380
ttgctgttta gccgtgggtc tcctgctggc atgtctgttc agcccaaaaa ctggctacct 1440
ggaccctgtt accggcagca gcgcgtttca aagacaaaaa cagacaacaa caacagcaac 1500
tttacctgga ctggtgcttc aaaatataac ctcaatggcc gtgaatctat catcaatcct 1560
ggcactgcta tggcctcaca caaagacgac aaagacaagt tctttcccat gagcggtgtc 1620
atgatttttg gcaaagagag cgccggagct tcaaacactg cattggacaa tgtcatgatt 1680
accgacgaag aggaaattaa agccactaac cctgtggcca cggagagatt tgggactgtg 1740
gcagtcaacc tccagagcag cagcacagac cctgcgaccg gagatgtcca tgttatggga 1800
gccttacctg gcatggtgtg gcaagacaga gacgtgtacc tgcagggtcc catttgggcc 1860
aagattcctc acacggatgg acactttcac ccgtctccgc tgatgggcgg ctttggactg 1920
aaacacccgc ctcctcagat cctcatcaaa aacacgcctg tacctgcgaa tcctccggcg 1980
gagttcagcg ctacaaagtt tgcttcattc atcacccagt actccactgg acaggtcagc 2040
gtggagattg agtgggagct gcagaaggaa aacagcaagc gctggaatcc cgaggtgcag 2100
tacacatcca actacgcaaa atctgccaat gtggacttta ctgtggacaa caatggactt 2160
tatactgagc ctcgccccat tggcacccgt tacctcaccc gtcccctgta a 2211

-continued

```
<210> SEQ ID NO 35
<211> LENGTH: 380
<212> TYPE: DNA
<213> ORGANISM: Cytomegalovirus

<400> SEQUENCE: 35

gacattgatt attgactagt tattaatagt aatcaattac ggggtcatta gttcatagcc      60

catatatgga gttccgcgtt acataactta cggtaaatgg cccgcctggc tgaccgccca     120

acgacccccg cccattgacg tcaataatga cgtatgttcc catagtaacg ccaataggga     180

ctttccattg acgtcaatgg gtggagtatt tacggtaaac tgcccacttg gcagtacatc     240

aagtgtatca tatgccaagt acgcccccta ttgacgtcaa tgacggtaaa tggcccgcct     300

ggcattatgc ccagtacatg accttatggg actttcctac ttggcagtac atctacgtat     360

tagtcatcgc tattaccatg                                                 380


<210> SEQ ID NO 36
<211> LENGTH: 139
<212> TYPE: DNA
<213> ORGANISM: Adeno-associated virus

<400> SEQUENCE: 36

aggggtggag tcgtgacgtg aattacgtca tagggttagg gaggtcctgt attagaggtc      60

acgtgagtgt tttgcgacat tttgcgacac catgtggtca cgctgggtat ttaagcccga     120

gtgagcacgc agggtctcc                                                  139


<210> SEQ ID NO 37
<211> LENGTH: 21
<212> TYPE: DNA
<213> ORGANISM: Artificial Sequence
<220> FEATURE:
<223> OTHER INFORMATION: VG0896_crosspack_f

<400> SEQUENCE: 37

tttgggaagc aaggctcaga g                                                21


<210> SEQ ID NO 38
<211> LENGTH: 21
<212> TYPE: DNA
<213> ORGANISM: Artificial Sequence
<220> FEATURE:
<223> OTHER INFORMATION: VG0897_crosspack_r

<400> SEQUENCE: 38

gcttgtctgt tgcctctctg g                                                21
```